US008476047B2

(12) United States Patent
Burlew et al.

(10) Patent No.: US 8,476,047 B2
(45) **Date of Patent: *Jul. 2, 2013**

(54) EXTRACTION SOLVENTS DERIVED FROM OIL FOR ALCOHOL REMOVAL IN EXTRACTIVE FERMENTATION

(71) Applicants: Keith H. Burlew, Middletown, DE (US); Robert Dicosimo, Chadds Ford, PA (US); Michael Charles Grady, Oaklyn, NJ (US)

(72) Inventors: Keith H. Burlew, Middletown, DE (US); Robert Dicosimo, Chadds Ford, PA (US); Michael Charles Grady, Oaklyn, NJ (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,254

(22) Filed: Dec. 3, 2012

(65) Prior Publication Data

US 2013/0089900 A1 Apr. 11, 2013

Related U.S. Application Data

(63) Continuation of application No. 13/162,643, filed on Jun. 17, 2011.

(60) Provisional application No. 61/440,034, filed on Feb. 7, 2011, provisional application No. 61/379,546, filed on Sep. 2, 2010, provisional application No. 61/368,429, filed on Jul. 28, 2010, provisional application No. 61/368,444, filed on Jul. 28, 2010, provisional application No. 61/368,436, filed on Jul. 28, 2010, provisional application No. 61/368,451, filed on Jul. 28, 2010, provisional application No. 61/356,290, filed on Jun. 18, 2010.

(51) Int. Cl.
*C12P 7/02* (2006.01)
*C12P 7/16* (2006.01)

(52) U.S. Cl.
USPC .......................................... 435/155; 435/160

(58) Field of Classification Search
None
See application file for complete search history.

(56) References Cited

U.S. PATENT DOCUMENTS

| | | | |
|---|---|---|---|
| 6,646,146 | B1 | 11/2003 | Sinnema et al. |
| 7,851,188 | B2 | 12/2010 | Donaldson et al. |
| 7,932,063 | B2 | 4/2011 | Dunson et al. |
| 2007/0077635 | A1 | 4/2007 | Brunner et al. |
| 2008/0182308 | A1 | 7/2008 | Donaldson et al. |
| 2009/0163376 | A1 | 6/2009 | Li et al. |
| 2009/0171129 | A1 | 7/2009 | Evanko et al. |
| 2009/0269823 | A1 | 10/2009 | Bramucci et al. |
| 2009/0305363 | A1 | 12/2009 | Anthony et al. |
| 2009/0305370 | A1 | 12/2009 | Grady et al. |
| 2010/0081154 | A1 | 4/2010 | Flint et al. |
| 2010/0124773 | A1 | 5/2010 | Yang |
| 2011/0124060 | A1 | 5/2011 | Anthony et al. |
| 2011/0244536 | A1 | 10/2011 | Nagarajan et al. |
| 2011/0312044 | A1 | 12/2011 | Anton et al. |
| 2011/0312053 | A1 | 12/2011 | Burlew et al. |
| 2012/0015416 | A1 | 1/2012 | Anthony et al. |
| 2012/0156738 | A1 | 6/2012 | Anton et al. |
| 2012/0164302 | A1 | 6/2012 | Roesch et al. |

FOREIGN PATENT DOCUMENTS

| | | |
|---|---|---|
| GB | 2146638 | 4/1985 |
| JP | 1986192291 | 8/1986 |
| WO | WO2009149270 | 12/2009 |
| WO | WO2010049491 | 5/2010 |
| WO | WO2011063402 | 5/2011 |

OTHER PUBLICATIONS

Ban et al., Whole cell biocatalyst for biodiesel fuel production utilizing *Rhizopus oryzae* cells immobilized within biomass support particles, Biochem. Eng. J. 8:39-43, 2001.
Barros et al., Integration of Enzyme Catalysis in an Extraction Fermentation Process, Studies in Organic Chemistry 29, 1986.
Bellion et al., Microb. Growth C1 Compd., [Int. Symp.], 7th (1993), 415 32, Editor(s): Murrell, J. Collin; Kelly, Don P. Publisher: Intercept, Andover, UK.
Bligh et al., A Rapid Method of Total Lipid Extraction and Purification, Can J Biochem Physiol 37:911-917, 1959.
Gupta et al., Bacterial lipases: an overview of production, purification and biochemical properties, Appl Microbiol Biotechnol 64:763-781, 2004.
Horton et al., Engineering hybrid genes without the use of restriction enzymes: gene splicing by overlap extension, Gene, 77:61-68, 1989.
Kim et al., Extractive Recovery of Products from Fermentation Broths, Biotechnol Bioprocess Eng 4:1-11, 1999.
Kohlhase et al., Catalytic Effects in the Ammonolysis of Vegetable Oils, The Journal of the American Oil Chemists' Society 48:265-270, 1971.
Lynd et al., Microbial Cellulose Utilization: Fundamentals of Biotechnology, Microbiology and Molecular Biology Reviews 66:506-577, 2002.

(Continued)

*Primary Examiner* — Nashaat Nashed
(74) *Attorney, Agent, or Firm* — Christine M. Lhulier

(57) ABSTRACT

In an alcohol fermentation process, oil derived from biomass is hydrolyzed into an extractant available for in situ removal of a product alcohol such as butanol from a fermentation broth. The glycerides in the oil can be catalytically (e.g., enzymatically) hydrolyzed into free fatty acids, which form a fermentation product extractant having a partition coefficient for a product alcohol greater than a partition coefficient of the oil of the biomass for the product alcohol. Oil derived from a feedstock of an alcohol fermentation process can be hydrolyzed by contacting the feedstock including the oil with one or more enzymes whereby at least a portion of the oil is hydrolyzed into free fatty acids forming a fermentation product extractant, or the oil can be separated from the feedstock prior to the feedstock being fed to a fermentation vessel, and the separated oil can be contacted with the enzymes to form the fermentation product extractant. The fermentation product extractant can be contacted with a fermentation broth for in situ removal of a product alcohol.

13 Claims, 9 Drawing Sheets

OTHER PUBLICATIONS

Ma et al., Plasmid construction by homologous recombination in yeast, Gene, 58:201-216, 1987.
Malinowski, Two-phase partitioning bioreactors in fermentation technology, Biotechnology Advances 19:525-538, 2001.
Methods in Yeast Genetics, 2005, Cold Spring Harbor Laboratory Press, Cold Spring Harbor, NY, pp. 201-202.
Oliveira et al., Production and Extractive Biocatalysis of Ethanol Using Microencapsulated Yeast Cells and Lipase System, J Chem Technol Biotechnol 52:219-225, 1991.
Oliveira et al., Immobilization of *Saccharomyces cerevisiae* Cells and *Rhizomucor miehi* Lipase for the Production and Extractive . . . , Bioprocess Eng 16:349-353, 1997.
Oliveira et al., Improvement of Alcoholic Fermentations by Simultaneous Extraction and Enzymatic Esterification of Ethanol, J Mol Catal B: Enzym 5:29-33, 1998.
Oliveira et al., Effect of extraction and Enzymatic Esterification of Ethanol on Glucose Consumption by Two *Saccharomyces* . . . , J Chem Technol Biotechnol 76:285-290, 2001.
Oudshoorn et al., Assessment of Options for Selective 1-Butanol Recovery from Aqueous Solution, Industrial and Engineering Chemistry Research 48:7325-7336, 2009.
Roe et al., Fatty Acid Amides. IV. Reaction of Fats With Ammonia and Amines, The Journal of the American Oil Chemists' Society 29:18-22, 1952.
Roffler, Steve Ronald: Extractive fermentation—lactic acid and acetone/butanol production, 1986, pp. 1-289, PhD. Dissertation in Chemical Engineering, UC Berkeley.
Sulter et al., Proliferation and metabolic significance of peroxisomes in *Candida boidinii* during growth on D-alanine or oleic acid . . . , Arch Microbiol 153:485-489, 1990.
Yoo et al., Enzymatic Synthesis of Sugar Fatty Acid Esters, Journal of industrial Engineering Chemistry 13:1-5, 2007.
International Search Report and Written Opinion dated Oct. 14, 2011, International Application No. PCT/US2011/040806.
U.S. Appl. No. 13/193,147, filed Jul. 28, 2011.
U.S. Appl. No. 61/440,034, filed Feb. 7, 2011.

EXTRACTION SOLVENTS DERIVED FROM OIL FOR ALCOHOL REMOVAL IN EXTRACTIVE FERMENTATION

This application claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; U.S. patent application Ser. No. 13/160,766, filed on Jun. 15, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates the production of fermentative alcohols such as butanol, and in particular to extraction solvents for extractive fermentation and processes for converting oil derived from biomass into the extraction solvents.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical with a variety of applications including use as a fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In order to be technically and economically viable, liquid-liquid extraction calls for good contact between the extractant and the fermentation broth for efficient mass transfer of the product alcohol into the extractant; good phase separation of the extractant from the fermentation broth (during and/or after fermentation); efficient recovery and recycle of the extractant; minimal degradation of the ability of the extractant to extract the product alcohol (e.g., by preventing the lowering of the partition coefficient for the product alcohol into the extractant); and minimal contamination of the extractant by lipids that lower the partition coefficient over a long-term operation.

The partition coefficient of the extractant can be degraded over time with each recycle, for example, by the build-up of lipids present in the biomass that is fed to the fermentation vessel as feedstock of hydrolysable starch. As an example, a liquefied corn mash loaded to a fermentation vessel at 30 wt % dry corn solids can result in a fermentation broth that contains about 1.2 wt % corn oil during conversion of glucose to butanol by simultaneous saccharification and fermentation (SSF) (with saccharification of the liquefied mash occurring during fermentation by the addition of glucoamylase to produce glucose). The dissolution of the corn oil lipids in oleyl alcohol (OA) serving as an extractant during ISPR can result in build-up of lipid concentration with each OA recycle, decreasing the partition coefficient for the product alcohol in OA as the lipid concentration in OA increases with each recycle of OA.

In addition, the presence of the undissolved solids during extractive fermentation can negatively affect the efficiency of alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the extractant used in extractive fermentation with lipid have included biomass wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ which contains a majority of the lipids present in ground whole grain such as corn, resulting in corn that has a higher starch (endosperm) content. Dry fractionation does not separate the germ and fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in co-pending, commonly owned U.S. Provisional Application Ser. No. 61/356,290, filed Jun. 18, 2010. However, it would be advantageous if the degradation of the partition coefficient of the extractant can be reduced even without fractionation or removal of undissolved solids. Thus, there is a continuing need to develop more efficient methods and systems for producing product alcohols, such as butanol, through extractive fermentation in which the degradation of the partition coefficient of the extractant is reduced.

Moreover, the extractant (e.g., oleyl alcohol) is typically added to the fermentation process, rather than produced at a step in the process and therefore, the extractant is a raw material expense. Since extractant can be lost by adsorption on non-fermentable solids and/or diluted by lipids introduced into the fermentation process, the economics of an alcohol production process can be affected by the efficiency of the extractant recovery and recycle. Thus, there exists a continuing need for alternative extractants for ISPR that can result in a more economical process by reducing capital and/or operating costs.

BRIEF SUMMARY OF THE INVENTION

The present invention satisfies the above needs by providing methods for producing product alcohols such as butanol, in which the lipids in a biomass are converted into an extractant that can be used in ISPR, and in which the amount of lipids that are fed to the fermentation vessel with the feedstock and/or upon extractant recycle, are decreased. The present invention offers a solution to the degradation of the ability of the extractant to extract a product alcohol (e.g., butanol) by preventing the lowering of the partition coefficient for the product alcohol into the extractant. The application offers a solution to the contamination of the extractant by triglycerides that lower the partition coefficient of the extractant for a product alcohol. The present invention provides further related advantages as will be made apparent by the description of the embodiments that follow.

Catalytic (e.g., enzymatic) hydrolysis of lipids derived from biomass into fatty acids can decrease the rate of undesirable build-up of lipids in the ISPR extractant. The fatty acids can be obtained from hydrolysis of lipids found in the biomass which supplies the fermentable carbon for fermentation. Fatty acids would not be expected to decrease the partition coefficient of the product alcohol such as a butanol into the extractant phase as much as the lipids, as the partition coefficient for butanol from water to fatty acids has been determined to be significantly greater than the partition coefficient for butanol from water to fatty acid esters or triglycerides. Moreover, the fatty acids can be used as an ISPR extractant which can be produced at a step in the alcohol production process and can be used in place of, or in addition to, a supplied, exogenous ISPR extractant that is not produced in the process (such as, but not limited to, oleyl alcohol or oleic acid), thereby reducing the raw material expense for the ISPR extractant.

In one embodiment, the present invention is directed to a method comprising contacting biomass comprising water, fermentable carbon source, and oil with one or more catalyst whereby at least a portion of the oil is hydrolyzed by one or more catalyst to form an extractant, wherein the fermentable carbon source and the oil are both derived from the biomass. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase.

In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids and fatty amides. In a further embodiment, a partition coefficient of the extractant for the product alcohol may be greater than a partition coefficient of the oil of the biomass for the product alcohol.

The method of the present invention may further comprise the step of inactivating the catalyst after at least a portion of the oil is hydrolyzed. In another embodiment, the method may further comprise the step of separating the oil from the biomass prior to hydrolysis by one or more catalyst. The claimed method may also further comprise the steps of contacting the biomass with a fermentation broth in a fermentation vessel; fermenting the carbon source of the biomass to produce a product alcohol; and removing in situ the product alcohol from the fermentation broth by contacting the broth with the extractant. The product alcohol may be butanol.

In another embodiment, the present invention is directed to a method for producing an alcohol comprising (a) providing biomass comprising water, fermentable carbon source, and oil; (b) liquefying the biomass to produce a liquefied biomass; (c) contacting the liquefied biomass with one or more catalysts whereby at least a portion of the oil is hydrolyzed to form an extractant; (d) contacting the liquefied biomass with a saccharification enzyme capable of converting oligosaccharides into fermentable sugar; (e) contacting the liquefied biomass with a fermentation broth in a fermentation vessel; (f) fermenting the carbon source of the liquefied biomass to produce a product alcohol; (g) removing in situ the product alcohol from the fermentation broth by contacting the broth with the extractant; and optionally steps (c) and (d) occur concurrently. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase. In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids or fatty amides. In a further embodiment, a partition coefficient of the extractant for the product alcohol may be greater than a partition coefficient of the oil of the biomass for the product alcohol. The method of the present invention may further comprise the step of inactivating the catalyst after at least a portion of the oil is hydrolyzed. The product alcohol may be butanol.

The present invention is also directed to a composition comprising a recombinant microorganism capable of producing an alcohol; fermentable carbon source; one or more catalysts capable of hydrolyzing glycerides into fatty acids; oil comprising glycerides; and fatty acids. The one or more catalysts may be selected from esterase, lipase, phospholipase, and lysophospholipase, and the oil may be corn, tallow, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha and vegetable oil blends. In a further embodiment, the fermentable carbon source and the oil are derived from biomass. The biomass may comprise corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. The composition may further comprise a saccharification enzyme and/or undissolved solids. The composition may also comprise at least one or more of monoglycerides, diglycerides, triglycerides, glycerol, monosaccharides, oligosaccharides, or alcohol. In addition, the alcohol may be butanol.

In some embodiments, a method of removing oil derived from biomass from a fermentation process includes contacting an aqueous biomass feedstream with a catalyst. The feedstream includes water, fermentable carbon and an amount of oil, and the fermentable carbon and the oil are both derived from the biomass. At least a portion of the oil is hydrolyzed according to methods described in the present invention into fatty acids to form a catalyst-treated biomass feedstream including the fatty acids.

In some embodiments, a method of producing an extractant for in situ removal of a product alcohol includes providing biomass which includes sugar and oil, the oil having an amount of triglycerides, and contacting the oil with a composition including one or more enzymes capable of hydrolyzing the triglycerides into fatty acids. The triglycerides in the oil are hydrolyzed to form a fermentation product extractant having a partition coefficient for the product alcohol greater than a partition coefficient of the oil of the biomass for the product alcohol.

In some embodiments, a method for producing butanol includes (a) providing biomass having starch and oil, the oil including an amount of glycerides; (b) liquefying the biomass to produce a liquefied biomass, the liquefied biomass including oligosaccharides hydrolyzed from the starch; (c) contacting the biomass of step (a) or the liquefied biomass of step (b) with a composition having one or more enzymes capable of converting the glycerides into free fatty acids whereby the free fatty acids form a fermentation product extractant; (d) contacting the liquefied biomass with a saccharification enzyme capable of converting oligosaccharides into fermentable sugar including monomeric glucose; (e) contacting the liquefied biomass with a biocatalyst capable of converting the fermentable sugar to butanol whereby a fermentation product comprising butanol is produced; and (f) contacting the fermentation product with the fermentation product extractant whereby the butanol is separated from the fermentation product, the fermentation product extractant having a partition coefficient for the butanol greater than a partition coefficient of the oil of the biomass for the butanol.

In some embodiments, a method includes, at a step during a process to produce a product alcohol from a feedstock, contacting the product alcohol with an extractant comprising free fatty acids obtained from enzymatic hydrolysis of a native oil wherein the oil comprises glycerides. The extractant has a partition coefficient for the product alcohol greater than a partition coefficient of the native oil for the product alcohol.

In some embodiments, the process to produce a product alcohol from a feedstock includes (a) liquefying the feedstock to create a feedstock slurry; (b) centrifuging the feedstock slurry of (a) to produce a centrifuge product including (i) an aqueous layer comprising sugar, (ii) a plant-derived oil layer, and (iii) a solids layer; (c) feeding the aqueous layer of (b) to a fermentation vessel; and (d) fermenting the sugar of the aqueous layer to produce the product alcohol.

In some embodiments, the process to produce a product alcohol from a feedstock further includes adding the extractant to the fermentation vessel to form a two-phase mixture comprising an aqueous phase and a product alcohol-containing organic phase.

In some embodiments, the native oil is a plant-derived oil, and in some embodiments, the process to produce a product alcohol from a feedstock further includes obtaining the plant-derived oil from the plant-derived oil layer; and converting the plant-derived oil into the extractant by contacting the oil with one or more enzymes that hydrolyze the glycerides into free fatty acids.

In some embodiments, the process to produce a product alcohol from a feedstock further includes inactivating the one or more enzymes after at least a portion of the glycerides have been hydrolyzed into free fatty acids.

In some embodiments, the process to produce a product alcohol from a feedstock further includes feeding the plant-derived oil to the fermentation vessel prior to the step of converting the plant-derived oil into the extractant.

In some embodiments, the process to produce a product alcohol from a feedstock further includes adding a second extractant to the fermentation vessel to form a two-phase mixture comprising an aqueous phase and a product alcohol-containing organic phase.

In some embodiments, the plant-derived oil is converted to the extractant after the step of adding a second extractant.

In some embodiments, a method of removing oil derived from biomass from a fermentation process, includes (a) providing a fermentation broth comprising a product alcohol and oil derived from biomass, the oil including glycerides; (b) contacting the fermentation broth with a first extractant to form a two-phase mixture comprising an aqueous phase and an organic phase, wherein the product alcohol and the oil partition into the organic phase to form a product alcohol-containing organic phase; (c) separating the product alcohol-containing organic phase from the aqueous phase; (d) separating the product alcohol from the organic phase to produce a lean organic phase; and (e) contacting the lean organic phase with a composition comprising one or more catalysts capable of hydrolyzing the glycerides into free fatty acids to produce a second extractant comprising at least a portion of the first extractant and free fatty acids.

In some embodiments, the method further includes repeating step (b) by contacting the fermentation broth with the second extractant of step (e).

In some embodiments, an in situ fermentation extractant-forming composition includes (a) mash formed from biomass and including water, starch and oil, (b) a catalyst capable of hydrolyzing at least a portion of the triglycerides into free fatty acids, and (c) free fatty acids. The starch and the oil are both derived from the biomass, and the oil includes an amount of triglycerides.

In some embodiments, a fermentation broth includes (a) a recombinant microorganism capable of producing butanol, (b) oligosaccharides, (c) a catalyst for hydrolyzing glycerides into free fatty acids, (d) glycerides, and (e) free fatty acids.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a liquefied biomass is contacted with a catalyst for lipid hydrolysis before fermentation.

FIG. 2 schematically illustrates an exemplary method and system of the present invention, in which a liquefied and saccharified biomass is contacted with a catalyst for lipid hydrolysis before fermentation.

FIG. 3 schematically illustrates an exemplary method and system of the present invention, in which lipids in a biomass feedstream are contacted with a catalyst for lipid hydrolysis before or during liquefaction.

FIG. 4 schematically illustrates an exemplary method and system of the present invention, in which undissolved solids and lipids are removed from a liquefied biomass before fermentation, and in which the removed lipids are hydrolyzed into free fatty acids using a catalyst, and the free fatty acids are supplied to the fermentation vessel.

FIG. 5 schematically illustrates an exemplary method and system of the present invention, in which lipids derived from native oil are hydrolyzed into free fatty acids using a catalyst, and the free fatty acids are supplied to the fermentation vessel.

FIG. 6 schematically illustrates an exemplary method and system of the present invention, in which biomass lipids present in a first extractant exiting a fermentation vessel are converted into free fatty acids that are supplied to a fermentation vessel as a second extractant.

DETAILED DESCRIPTION OF THE INVENTION

Figure 1:
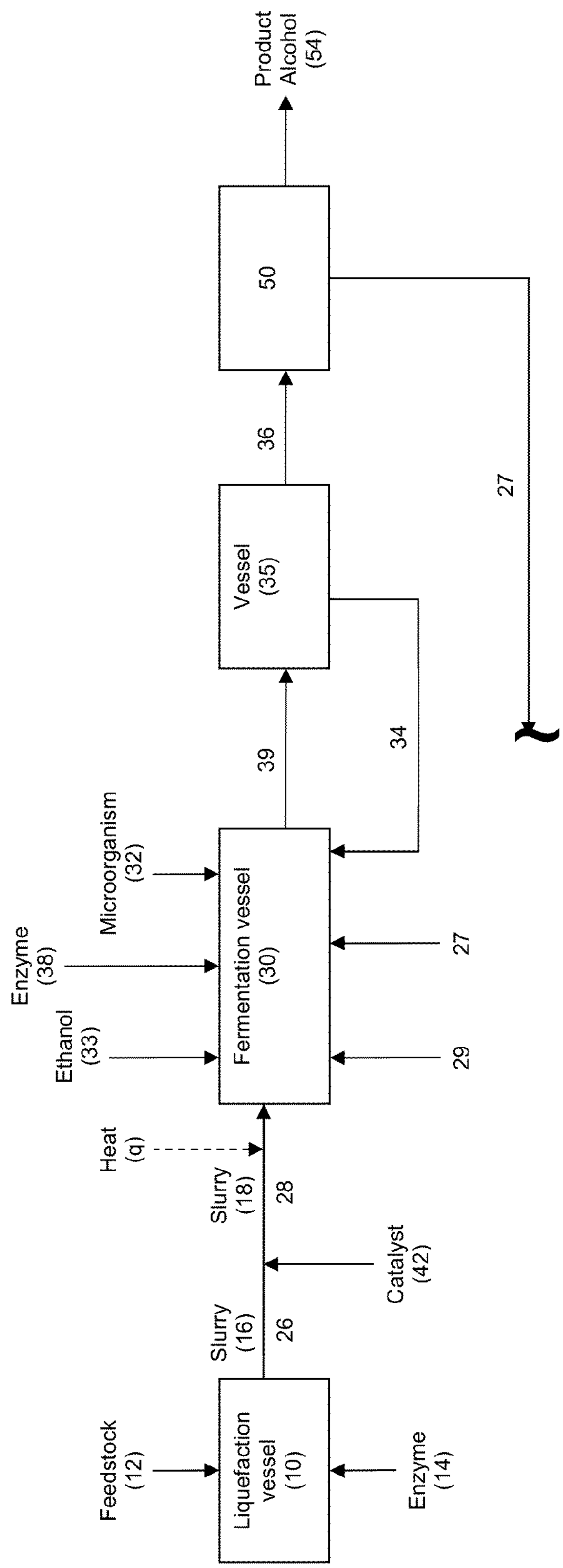

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, cane, barley, cellulosic material, lignocellulosic material, or mixtures thereof.

"Fermentation broth" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol, and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butanol ester in either the organic or aqueous phase.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COON in which a carbon atom is bonded to an oxygen atom by a double bond to make a carbonyl group (—C═O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention provides extractants obtained by catalytic hydrolysis of oil glycerides derived from biomass and methods of producing the extractants. In particular, the glycerides in biomass oil can be catalytically hydrolyzed into fatty acids using a catalyst such as an enzyme. The fatty acids can serve as extractants for in situ removal of a product alcohol such as butanol from a fermentation broth. Thus, the present invention also provides methods for producing a product alcohol such as butanol through extractive fermentation using the extractants that were produced from the biomass oil. The present invention also provides methods for catalytically hydrolyzing the oil present in a feedstock slurry into fatty acids prior to fermentation, whereby the oil is converted to fatty acids and the degradation of the partition coefficient of the ISPR extractant over time that is attributable to the presence of the oil in the fermentation vessel can be reduced. Moreover, the fatty acids obtained by hydrolysis of the feedstock oil can serve as an ISPR extractant having a partition coefficient for a fermentative alcohol greater than a partition coefficient of the feedstock oil for the fermentative alcohol. The feedstock oil can be separated from the feedstock slurry prior to hydrolysis and used as an ISPR extractant, or the oil can be hydrolyzed into fatty acids while in the feedstock slurry. Further, fatty acids as ISPR extractant can be used in place of or in addition to a conventional exogenous extractant, such as oleyl alcohol or oleic acid, thereby reducing the raw material expense associated with the exogenous extractant.

The present invention will be described with reference to the Figures. FIG. 1 illustrates an exemplary process flow diagram for production of fermentative alcohol according to an embodiment of the present invention. As shown, a feedstock 12 can be introduced to an inlet in a liquefaction vessel 10 and liquefied to produce a feedstock slurry 16. Feedstock 12 contains hydrolysable starch that supplies a fermentable carbon source (e.g., fermentable sugar such as glucose), and can be a biomass such as, but not limited to, rye, wheat, corn, cane, barley, cellulosic material, lignocellulosic material, or mixtures thereof, or can otherwise be derived from a biomass. In some embodiments, feedstock 12 can be one or more components of a fractionated biomass and in other embodiments, feedstock 12 can be a milled, unfractionated biomass. In some embodiments, feedstock 12 can be corn such as dry milled, unfractionated corn kernels, and the undissolved solids can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides fatty acids having a high oleic acid content for contacting with a fermentation broth. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations.

The process of liquefying feedstock 12 involves hydrolysis of starch in feedstock 12 into sugars including, for example, dextrins and oligosaccharides, and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to fatty acids.

Feedstock slurry 16 produced from liquefying feedstock 12 includes sugar, oil 26, and undissolved solids derived from the biomass from which feedstock 12 was formed. In some embodiments, the oil is in an amount of about 0 wt % to at least about 2 wt % of the fermentation broth composition. In some embodiments, the oil is in an amount of at least about 0.5 wt % of the feedstock. Feedstock slurry 16 can be discharged from an outlet of liquefaction vessel 10. In some embodiments, feedstock 12 is corn or corn kernels and therefore, feedstock slurry 16 is a corn mash slurry.

A catalyst 42 can be added to feedstock slurry 16. Catalyst 42 is capable of hydrolyzing glycerides in oil 26 to free fatty acids (FFA) 28. For example, when feedstock 12 is corn, then oil 26 is the feedstock's constituent corn oil, and the free fatty acids 28 are corn oil fatty acids (COFA). Thus, after introduction of catalyst 42 to feedstock slurry 16, at least a portion of the glycerides in oil 26 are hydrolyzed to FFA 28, resulting in a feedstock slurry 18 having FFA 28 and catalyst 42. The resulting acid/oil composition from hydrolyzing oil 26 is typically at least about 17 wt % FFA. In some embodiments, the resulting acid/oil composition from hydrolyzing oil 26 is at least about 20 wt % FFA, at least about 25 wt % FFA, at least about 30 wt % FFA, at least about 35 wt % FFA, at least about 40 wt % FFA, at least about 45 wt % FFA, at least about 50 wt % FFA, at least about 55 wt % FFA, at least about 60 wt % FFA, at least about 65 wt % FFA, at least about 70 wt % FFA, at least about 75 wt % FFA, at least about 80 wt % FFA, at least about 85 wt % FFA, at least about 90 wt % FFA, at least about 95 wt % FFA, or at least about 99 wt % FFA. In some embodiments, the concentration of the fatty acid (such as carboxylic acid) in the fermentation vessel exceeds the solubility limit in the aqueous phase and results in the production a two-phase fermentation mixture comprising an organic phase and an aqueous phase. In some embodiments, the concentration of carboxylic acid (or fatty acid) in the fermentation broth is typically not greater than about 0.8 g/L and is limited by the solubility of the carboxylic acid (or fatty acid) in the broth.

In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus pumilus, Bacillus strearothermophilus, Bacillus subtilis, Brochothrix thermosohata, Candida cylindracea* (*Candida rugosa*), *Candida paralipolytica, Candida Antarctica* lipase A, *Candida antartica* lipase B, *Candida emobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. thermoidea, *Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei*, and *Yarrowia lipolytica*. In a further preferred aspect, the lipase is selected from the group consisting of *Thermomcyces lanuginosus* lipase, *Aspergillus* sp. lipase, *Aspergillus niger lipase, Aspergillus tubingensis* lipase, *Candida antartica* lipase B, *Pseudomonas* sp. lipase, *Penicillium roqueforti* lipase, *Penicillium camembertii* lipase, *Mucor javanicus* lipase, *Burkholderia cepacia* lipase, *Alcaligenes* sp. lipase, *Candida rugosa* lipase, *Candida parapsilosis* lipase, *Candida deformans* lipase, lipases A and B from *Geotrichum candidum, Neurospora crassa* lipase, *Nectria haematococca* lipase, *Fusarium heterosporum* lipase *Rhizopus delemar* lipase, *Rhizomucor miehei* lipase, *Rhizopus arrhizus* lipase, and *Rhizopus oryzae* lipase. Suitable commercial lipase preparations suitable as enzyme catalyst 42 include, but are not limited to Lipolase® 100 L, Lipex® 100L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* available from SigmaAldrich.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term "phospholipase" encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase A1 or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof. The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase A1 (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and 1-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

After at least a portion of the glycerides are hydrolyzed, in some embodiments, catalyst 42 can be inactivated. Any method known in the art can be used to render catalyst 42 inactive. For example, in some embodiments, catalyst 42 can be inactivated by the application of heat, by adjusting the pH of the reaction mass to a pH where catalyst 42 is irreversibly inactivated, and/or by adding a chemical or biochemical species capable of selectively inactivating the catalyst activity. As shown, for example, in the embodiment of FIG. 1, heat q is applied to feedstock slurry 18, whereby catalyst 42 becomes inactive. The application of heat q can be applied to feedstock slurry 18 before feedstock slurry 18 is fed to a fermentation vessel 30. Heat-treated feedstock slurry 18 (with inactive catalyst 42) is then introduced into a fermentation vessel 30 along with a microorganism 32 to be included in a fermentation broth held in fermentation vessel 30. Alternatively, feedstock slurry 18 can be fed to fermentation vessel 30 and subjected to heat q while in the fermentation vessel, before fermentation vessel inoculation of microorganism 32. For example, in some embodiments, catalyst inactivation treatment can be achieved by heating feedstock slurry 18 with heat q to temperature of at least about 75° C. for at least about 5 minutes, at least about 75° C. for at least about 10 minutes, at least about 75° C. for at least about 15 minutes, at least about 80° C. for at least about 5 minutes, at least about 80° C. for at least about 10 minutes, at least about 80° C. for at least about 15 minutes, at least about 85° C. for at least about 5 minutes, at least about 85° C. for at least about 10 minutes, or at least about 85° C. for at least about 15 minutes. In some embodiments, after being subject to heat q, feedstock slurry 18 is cooled to an appropriate temperature for fermentation prior to introduction to fermentation vessel 30 (or prior to fermentation vessel inoculation in the case that the application of heat q is conducted in the fermentation vessel). For example, in some embodiments, the temperature of feedstock slurry 18 is about 30° C. prior to contacting with a fermentation broth.

Inactivation of catalyst 42 is preferred when it is desirable to prevent catalyst 42 from esterifying alcohol with fatty acids 28 in the fermentation vessel. In some embodiments, production of an alcohol ester by esterification of product alcohol in a fermentation medium with an organic acid (e.g., fatty acid) and a catalyst (e.g., lipase) is desirable, as further described in co-pending, commonly owned U.S. Provisional Application Ser. No. 61/368,429, filed on Jul. 28, 2010; U.S. Provisional Application Ser. No. 61/379,546, filed on Sep. 2, 2010; and U.S. Provisional Application Ser. No. 61/440,034, filed on Feb. 7, 2011, all incorporated herein in its entirety by reference thereto. For example, for butanol production, active catalyst 42 in fermentation vessel (introduced via slurry 18) can catalyze the esterification of the butanol with fatty acids 28 (introduced via slurry 18) to form fatty acid butyl esters (FABE) in situ.

Fermentation vessel 30 is configured to ferment slurry 18 to produce a product alcohol such as butanol. In particular, microorganism 32 metabolizes the fermentable sugar in slurry 18 and excretes a product alcohol. Microorganism 32 is selected from the group of bacteria, cyanobacteria, filamentous fungi, and yeasts. In some embodiments, microorganism 32 can be a bacteria such as *E. coli*. In some embodiments, microorganism 32 can be a fermentative recombinant microorganism. The slurry can include sugar, for example, in the form of oligosaccharides, and water, and can comprise less than about 20 g/L of monomeric glucose, more preferably less than about 10 g/L or less than about 5 g/L of monomeric glucose. Suitable methodology to determine the amount of monomeric glucose is well known in the art. Such suitable methods known in the art include HPLC.

In some embodiments, slurry 18 is subjected to a saccharification process in order to break the complex sugars (e.g., oligosaccharides) in slurry 18 into monosaccharides that can be readily metabolized by microorganism 32. Any known saccharification process that is routinely utilized by the industry can be used including, but not limited to, the acid process, the acid-enzyme process, or the enzyme process. In some embodiments, simultaneous saccharification and fermentation (SSF) can occur inside fermentation vessel 30, as shown in FIG. 1. In some embodiments, an enzyme 38, such as glucoamylase, can be introduced to an inlet in fermentation vessel 30 in order to breakdown the starch or oligosaccharides to glucose capable of being metabolized by microorganism 32.

Optionally, ethanol 33 may be supplied to fermentation vessel 30 to be included in the fermentation broth. In some embodiments, when a recombinant microorganism having a butanol biosynthetic pathway is used as microorganism 32 for butanol production, microorganism 32 may require supplementation of a 2-carbon substrate (e.g., ethanol) to survive and grow. Thus, in some embodiments, ethanol 33 may be supplied to fermentation vessel 30.

However, it has been surprisingly found that methods of the present invention, in which free fatty acid (e.g., FFA 28) is present in the fermentation vessel, can allow reduction of the amount of ethanol 33 typically supplied for a given recombinant microorganism without detriment to the vitality of the recombinant microorganism. Further, in some embodiments, the methods of the present invention provide that the alcohol (e.g., butanol) production rate without ethanol supplementation to be comparable with the production rate that can be realized when ethanol 33 is supplemented. As further demonstrated by the comparative examples presented in Examples 1-14 below, the butanol production rate when fatty acid but not ethanol is in the fermentation vessel can be greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the butanol fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which fatty acids are produced at a step in the process and are contacted with microorganism cultures in a fermentation vessel for improving microorganism growth rate and glucose consumption are described in co-pending, commonly owned U.S. Provisional Application Ser. No. 61/368,451, filed on Jul. 28, 2010, which is incorporated herein in its entirety by reference thereto.

In fermentation vessel 30, alcohol is produced by microorganism 32. In situ product removal (ISPR) can be utilized to remove the product alcohol from the fermentation broth. In some embodiments, ISPR includes liquid-liquid extraction. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof, which contacts a fermentation broth and to form a two-phase mixture comprising an aqueous phase and an organic phase. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof, which contacts a fermentation broth and to form a two-phase mixture comprising an aqueous phase and an organic phase. Free fatty acids 28 from slurry 18 can also serve as an ISPR extractant 28. For example, when free fatty acids 28 are corn oil fatty acids (COFA), ISPR extractant 28 is COFA. ISPR extractant (FFA) 28 contacts the fermentation broth and forms a two-phase mixture comprising an aqueous phase 34 and an organic phase. The product alcohol present in the fermentation broth preferentially partitions into the organic phase to form an alcohol-containing organic phase 36. In some embodiments, fermentation vessel 30 has one or more inlets for receiving one or more additional ISPR extractants 29 which form a two-phase mixture comprising an aqueous phase and an organic phase, with the product alcohol partitioning into the organic phase.

The biphasic mixture can be removed from fermentation vessel 30 as stream 39 and introduced into a vessel 35, in which the alcohol-containing organic phase 36 is separated from the aqueous phase 34. The alcohol-containing organic phase 36 is separated from the aqueous phase 34 of the biphasic mixture stream 39 using methods known in the art including, but not limited to, siphoning, aspiration, decantation, centrifugation, using a gravity settler, membrane-assisted phase splitting, and the like. All or part of the aqueous phase 34 can be recycled into fermentation vessel 30 as fermentation medium (as shown), or otherwise discarded and replaced with fresh medium, or treated for the removal of any remaining product alcohol and then recycled to fermentation vessel 30. Then, the alcohol-containing organic phase 36 is treated in a separator 50 to recover product alcohol 54, and the resulting alcohol-lean extractant 27 can then be recycled back into fermentation vessel 30, usually in combination with fresh FFA 28 from slurry 18 and/or with fresh extractant 29 for further extraction of the product alcohol. Alternatively, fresh FFA 28 (from slurry 18) and/or extractant 29 can be continuously added to the fermentation vessel to replace the ISPR extractant(s) removed in biphasic mixture stream 39.

In some embodiments, any additional ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. In some embodiments, ISPR extractant 29 can be a carboxylic acid and in some embodiments, ISPR extractant 29 can be a fatty acid. In some embodiments, the carboxylic acid or fatty acid can have 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, ISPR extractant 29 is one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, ISPR extractant 29 is one or more of diacids, azelaic, dimer and sebacic acid. Thus, in some embodiments, ISPR extractant 29 can be a mixture of two or more different fatty acids. In some embodiments, ISPR extractant 29 can be a fatty acid derived from chemical or enzymatic hydrolysis of glycerides derived from native oil. For example, in some embodiments, ISPR extractant 29 can be free fatty acids 28' obtained by enzymatic hydrolysis of native oil such as biomass lipids as later described with reference to the embodiment of FIG. 5. In some embodiments, ISPR extractant 29 can be a fatty acid extractant selected from the group consisting of fatty acids, fatty alcohols, fatty amides, fatty acid methyl esters, lower alcohol esters of fatty acids, fatty acid glycol esters, hydroxylated triglycerides, and mixtures thereof, obtained from chemical conversion of native oil such as biomass lipids as described for example in co-pending, commonly owned U.S. Provisional Application Ser. No. 61/368,436, filed on Jul. 28, 2010. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. In some embodiments, additional ISPR extractant 29 includes COFA.

In situ extractive fermentation can be carried out in a batch mode or a continuous mode in fermentation vessel 30. For in situ extractive fermentation, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production, for example, the ISPR extractant can contact the fermentation medium at a time before the butanol concentration reaches a level which would be toxic to the microorganism. After contacting the fermentation medium with the ISPR extractant, the butanol product partitions into the extractant, decreasing the concentration in the aqueous phase containing the microorganism, thereby limiting the exposure of the production microorganism to the inhibitory butanol product.

The volume of the ISPR extractant to be used depends on a number of factors including the volume of the fermentation medium, the size of the fermentation vessel, the partition coefficient of the extractant for the butanol product, and the fermentation mode chosen, as described below. The volume of the extractant can be about 3% to about 60% of the fermentation vessel working volume. Depending on the efficiency of the extraction, the aqueous phase titer of butanol in the fermentation medium can be, for example, from about 1 g/L to about 85 g/L, from about 10 g/L to about 40 g/L, from about 10 g/L to about 20 g/L, from about 15 g/L to about 50 g/L or from about 20 g/L to about 60 g/L. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. Without being held to theory, it is believed that higher butanol titer may obtained with the extractive fermentation method, in part, from the removal of the toxic butanol product from the fermentation medium, thereby keeping the level below that which is toxic to the microorganism.

In a batchwise mode of in situ extractive fermentation, a volume of organic extractant is added to the fermentation vessel and the extractant is not removed during the process. This mode requires a larger volume of organic extractant to minimize the concentration of the inhibitory butanol product in the fermentation medium. Consequently, the volume of the fermentation medium is less and the amount of product produced is less than that obtained using the continuous mode. For example, the volume of the extractant in the batchwise mode can be 20% to about 60% of the fermentation vessel working volume in one embodiment, and about 30% to about 60% in another embodiment.

Gas stripping (not shown) can be used concurrently with the ISPR extractant to remove the product alcohol from the fermentation medium.

In the embodiment of FIG. 1, the product alcohol is extracted from the fermentation broth in situ, with the separation of the biphasic mixture 39 occurring in a separate vessel 35. In some embodiments, separation of the biphasic mixture 39 can occur in the fermentation vessel, as shown in the embodiments of later described FIGS. 2 and 3 in which the alcohol-containing organic phase stream 36 exits directly from fermentation vessel 30. Aqueous phase stream 34 can also exit directly from fermentation vessel 30, be treated for the removal of any remaining product alcohol and recycled, or discarded and replaced with fresh fermentation medium. The extraction of the product alcohol by the organic extractant(s) can be done with or without the removal of the microorganism from the fermentation broth. The microorganism can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

In a continuous mode of in situ extractive fermentation, the volume of the extractant can be about 3% to about 50% of the fermentation vessel working volume in one embodiment, about 3% to about 30% in another embodiment, 3% to about 20% in another embodiment; and 3% to about 10% in another embodiment. Because the product is continually removed from the reactor, a smaller volume of extractant is required enabling a larger volume of the fermentation medium to be used.

As an alternative to in situ extractive fermentation, the product alcohol can be extracted from the fermentation broth downstream of fermentation vessel 30. In such an instance, the fermentation broth can be removed from fermentation vessel 30 and introduced into vessel 35. Extractant 28 can then be introduced into vessel 35 and contacted with the fermentation broth to obtain biphasic mixture 39 in vessel 35, which is then separated into the organic and aqueous phases 36 and 34. Alternatively, extractant 28 can be added to the fermentation broth in a separate vessel (not shown) prior to introduction to vessel 35.

As a non-limiting prophetic example, with reference to the embodiment of FIG. 1, an aqueous suspension of ground whole corn (as feedstock 12), which can nominally contain about 4 wt % corn oil, can be treated with amylase (as liquefaction enzyme 14) at about 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. Optionally, the liquefied and lipase-treated mash 18 can be heated to inactivate lipase 42 prior to fermentation. Mash 18 can be cooled to about 30° C. (e.g., using a heat-exchanger) and loaded to fermentation vessel 30 at about 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a fermentation broth using a liquefied mash that has not been treated with lipase 42. In particular, the lipase 42 treatment can result in the conversion of corn oil lipids 26 (triglycerides (TG)) into COFA as FFA 28 (and some diglycerides (DG) or monoglycerides (MG)), decreasing the rate of build-up of lipids 26 in any ISPR extractant 29 (e.g., oleyl alcohol), and dissolution of COFA 28 into organic phase 36 during ISPR should not decrease the partition coefficient of butanol in organic phase 36 as much as would the dissolution of lipids (TG) into the organic phase 36.

In some embodiments, the system and processes of FIG. 1 can be modified such that feedstock slurry 16 (having oil 26) and catalyst 42 are introduced and contacted in fermentation vessel 30 so as to produce slurry 18 (having FFA 28). The fermentation vessel temperature can then be raised to heat inactivate catalyst 42. The fermentation vessel temperature can then be reduced, and the fermentation vessel can be inoculated with microorganism 32, whereby the sugars of slurry 18 can be fermented to produce a product alcohol.

In some embodiments, the system and processes of FIG. 1 can be modified such that simultaneous saccharification and fermentation (SSF) in fermentation vessel 30 is replaced with a separate saccharification vessel 60 (see FIG. 2) prior to fermentation vessel 30, as should be apparent to one of skill in the art. Thus, slurry 18 can be saccharified either before fermentation or during fermentation in an SSF process. It should also be apparent that catalyst 42 for hydrolysis of feedstock oil 26 can be introduced before, after, or contemporaneously with saccharification enzyme 38. Thus, in some embodiments, addition of enzyme 38 and catalyst 42 can be stepwise (e.g., catalyst 42, then enzyme 38, or vice versa), or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes).

Figure 2:
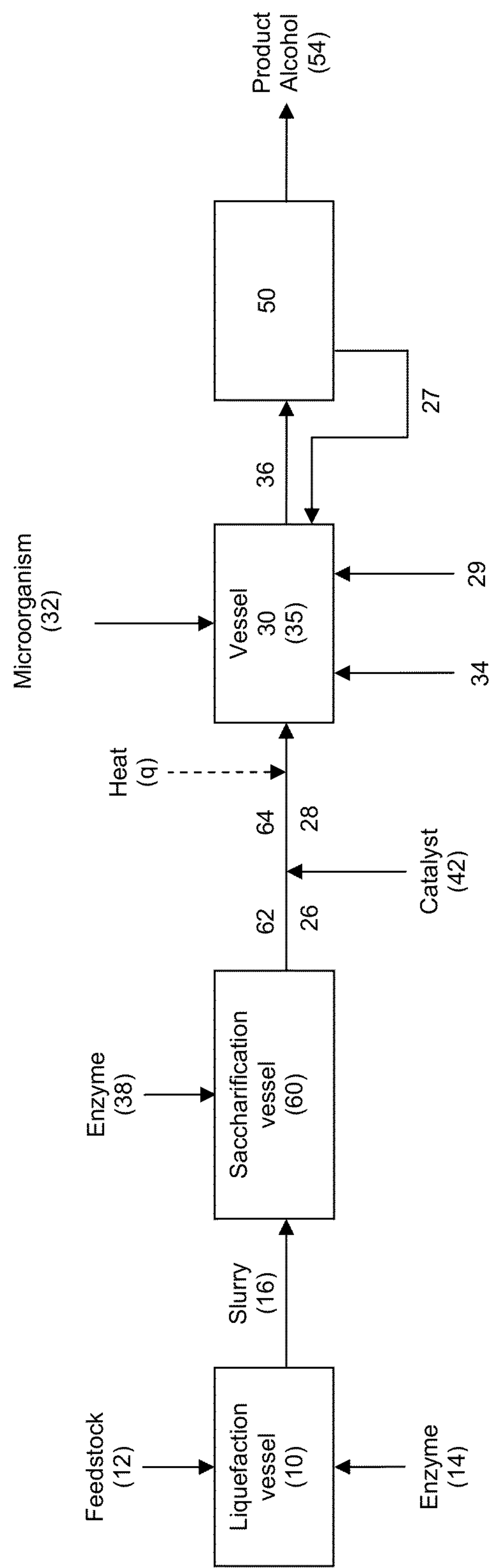

For example, as shown in the embodiment of FIG. 2, the system and processes of FIG. 1 can be modified such that simultaneous saccharification and fermentation (SSF) in fermentation vessel 30 is replaced with a separate saccharification vessel 60 prior to fermentation vessel 30. FIG. 2 is substantially identical to FIG. 1 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, oil 26, and undissolved solids derived from the feedstock. Oil 26 is hydrolyzed by the introduction of catalyst 42 resulting in a liquefied, saccharified feedstock slurry 64 having free fatty acids 28 and catalyst 42.

Alternatively, in some embodiments, catalyst 42 can be added with saccharification enzyme 38 to simultaneously produce glucose and hydrolyze oil lipids 26 to free fatty acids 28. The addition of enzyme 38 and catalyst 42 can be stepwise (e.g., catalyst 42, then enzyme 38, or vice versa) or simultaneous. Alternatively, in some embodiments, slurry 62 can be introduced to fermentation vessel with catalyst 42 being added directly to the fermentation vessel 30.

In the embodiment of FIG. 2, heat q is applied to feedstock slurry 64, whereby catalyst 42 becomes inactive, and heat-treated slurry 64 is then introduced to fermentation vessel 30 along with alcohol-producing microorganism 32, which metabolizes the monosaccharides to produce a product alcohol (e.g., butanol). Alternatively, slurry 64 can be fed to fermentation vessel 30 and subjected to heat q while in the fermentation vessel, before inoculation of microorganism 32.

As described above with reference to FIG. 1, free fatty acids 28 can also serve as an ISPR extractant for preferentially partitioning the product alcohol from the aqueous phase. In some embodiments, one or more additional ISPR extractants 29 can also be introduced into fermentation vessel 30. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. The remaining process operations of the embodiment of FIG. 2 are identical to FIG. 1 and therefore, will not be described in detail again.

In still other embodiments of the present invention, oil 26 derived from feedstock 12 can be catalytically hydrolyzed into FFA 28 either prior to or during liquefaction. For example, in the embodiment of FIG. 3, feedstock 12 having oil 26 is fed to liquefaction vessel 10, along with catalyst 42 for hydrolysis of at least a portion of the glycerides in oil 26 into FFA 28. Enzyme 14 (e.g., alpha-amylase) for hydrolyzing the starch in feedstock 12 can also be introduced to vessel 10 to produce a liquefied feedstock. The addition of enzyme 14 and catalyst 42 can be stepwise or simultaneous. For example, catalyst 42 can be introduced, and then enzyme 14 can be introduced after at least a portion of oil 26 has been hydrolyzed. Alternatively, enzyme 14 can be introduced, and then catalyst 42 can be introduced. The liquefaction process can involve the application of heat q. In such embodiments, it is preferred that catalyst 42 is introduced prior to or during liquefaction when the process temperature is below that which inactivates catalyst 42, so that oil 26 can be hydrolyzed. Thereafter, application of heat q can provide a two-fold purpose of liquefaction and inactivation of catalyst 42.

In any case, oil 26 in feedstock 12 is converted to FFA 28 in liquefaction vessel 10, such that biphasic feedstock slurry 18 exits liquefaction vessel 10. Biphasic slurry 18 includes both an organic phase of FFA 28 as well as sugar, water, and undissolved solids of an aqueous phase. In some embodiments, the aqueous phase can include glycerol (glycerin) from converting the glycerides in the oil to fatty acids. In some embodiments, such glycerol, if present, can be removed from the stream 18 prior to introduction into fermentation vessel 30.

Figure 3:
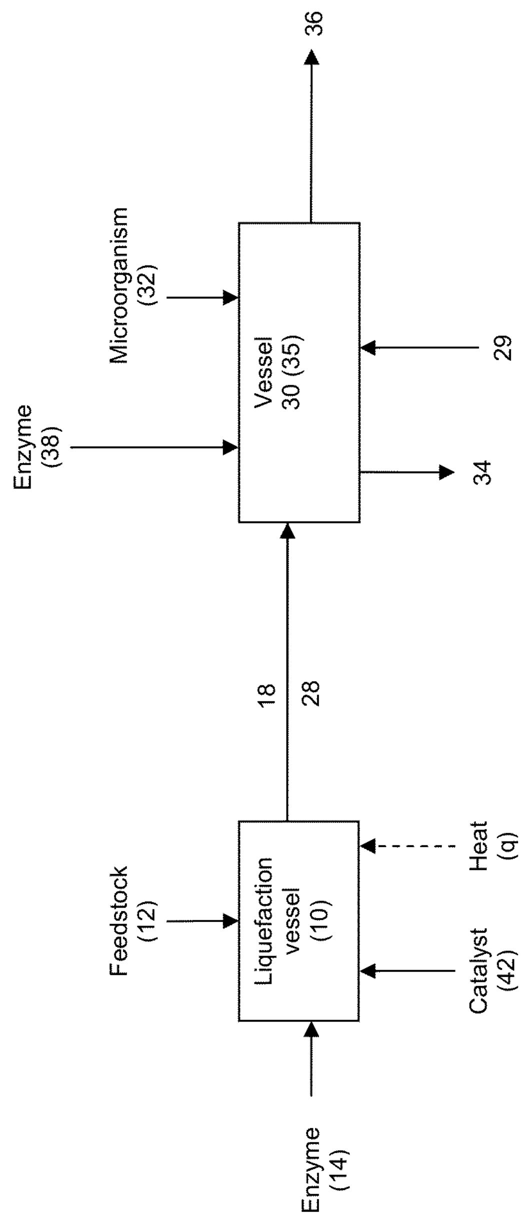

With reference to FIG. 3, biphasic stream 18 is contacted with the fermentation broth in fermentation vessel 30 to form a biphasic mixture. In fermentation vessel 30, product alcohol produced by SSF partitions into the organic phase including FFA 28. Alternatively, in some embodiments, the process can be modified to include a separate saccharification vessel as discussed in connection with FIG. 2. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Optionally, one or more additional extractants 29 can be introduced into fermentation vessel 30 to form an organic phase that preferentially partitions the product alcohol from the aqueous phase. Alcohol-containing organic phase 36 can be introduced to separator 50 for recovery of product alcohol 54 and optional recycle of recovered extractant 27 as shown in FIG. 1. The remaining process operations of the embodiment of FIG. 3 can be identical to the previously described figures and therefore, will not be described in detail again.

Figure 4:
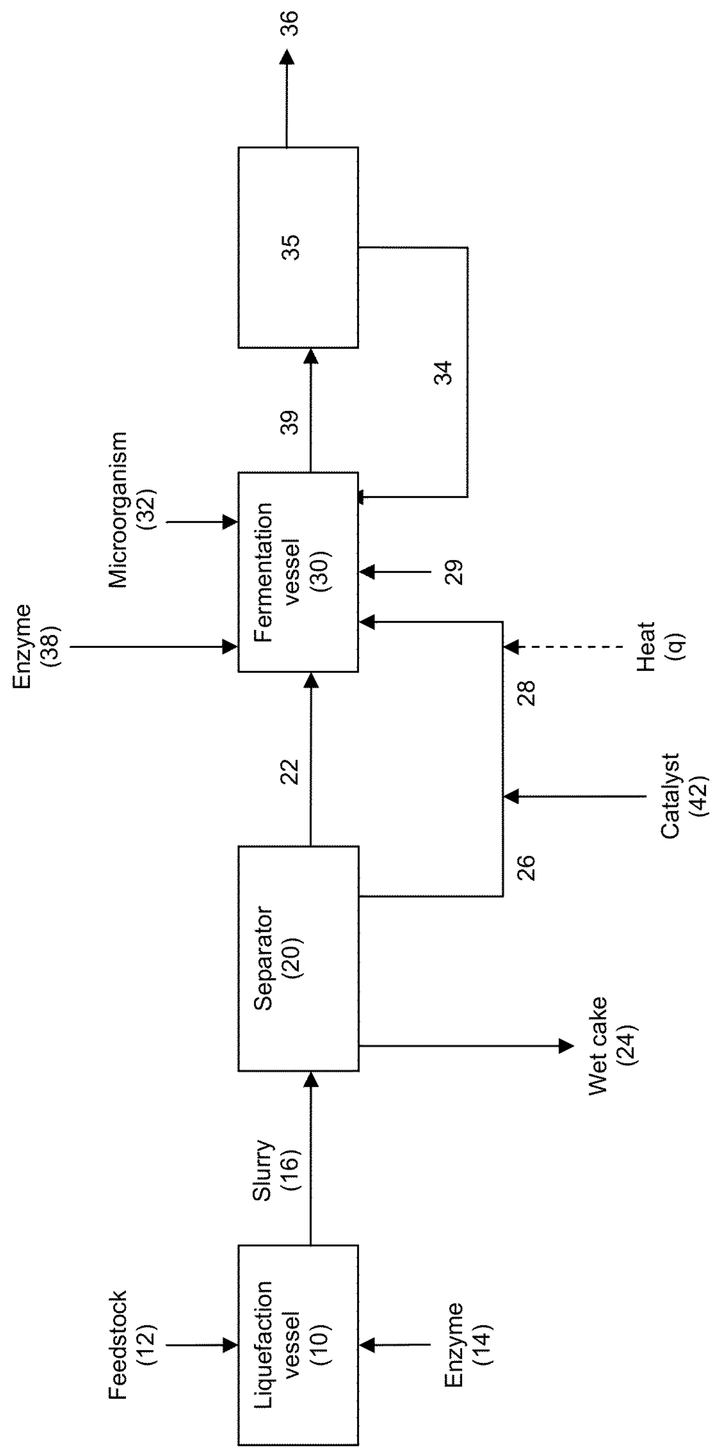

In some embodiments, including any of the earlier described embodiments with respect to FIGS. 1-3, undissolved solids can be removed from the feedstock slurry prior to introduction into fermentation vessel 30. For example, as shown in the embodiment of FIG. 4, feedstock slurry 16 is introduced into an inlet of a separator 20 which is configured to discharge the undissolved solids as a solid phase or wet cake 24. For example, in some embodiments, separator 20 may include a filter press, vacuum filtration, or a centrifuge for separating the undissolved solids from feedstock slurry 16. Optionally, in some embodiments, separator 20 can also be configured to remove some, or substantially all, of oil 26 present in feedstock slurry 16. In such embodiments, separator 20 can be any suitable separator known in the art for removing oil from an aqueous feedstream including, but not limited to, siphoning, decantation, aspiration, centrifugation, using a gravity settler, membrane-assisted phase splitting, and the like. The remaining feedstock including the sugar and water is discharged as an aqueous stream 22 to fermentation vessel 30.

In some embodiments, separator 20 removes oil 26 but not undissolved solids. Thus, aqueous stream 22 fed to fermentation vessel 30 includes undissolved solids. For example, in some embodiments, separator 20 includes a tricanter centrifuge 20 that agitates or spins feedstock slurry 16 to produces a centrifuge product comprising an aqueous layer containing the sugar and water (i.e., stream 22), a solids layer containing the undissolved solids (i.e., wet cake 24), and an oil layer (i.e., oil stream 26). In such a case, catalyst 42 can be contacted with the removed oil 26 to produce a stream of FFA 28 including catalyst 42, as shown in FIG. 4. Heat q can then be applied to the stream of FFA 28, whereby catalyst 42 becomes inactive. The stream of FFA 28 and inactive catalyst 42 can then be introduced into fermentation vessel 30, along with stream 22 and microorganism 32. Alternatively, FFA 28 and active catalyst 42 can be fed to fermentation vessel 30 from vessel 40, and active catalyst 42 can thereafter be subjected to heat q and inactivated while in the fermentation vessel, before inoculation of microorganism 32.

FFA 28 can serve as ISPR extractant 28 and forms a biphasic mixture in fermentation vessel 30. Product alcohol produced by SSF partitions into organic phase 36 constituted by FFA 28. In some embodiments, one or more additional ISPR extractants 29 can also be introduced into fermentation vessel 30. Thus, oil 26 (e.g., from feedstock) can be catalytically hydrolyzed to FFA 28, thereby decreasing the rate of build-up of lipids in an ISPR extractant while also producing an ISPR extractant. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced to separator 50 for recovery of product alcohol 54 and optional recycle of recovered extractant 27 as shown in FIG. 1. The remaining process operations of the embodiment of FIG. 4 are identical to FIG. 1 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 20 can be dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26 is not discharged separately from wet cake 24, but rather oil 26 is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock 16 via centrifugation are described in detail in co-pending, commonly owned U.S. Patent Application No. 61/356,290, filed Jun. 18, 2010, which is incorporated herein in its entirety by reference thereto.

In still other embodiments (not shown), saccharification can occur in a separate saccharification vessel 60 (see FIG. 2) which is located between separator 20 and liquefaction vessel 10, as should be apparent to one of skill in the art.

Figure 5:
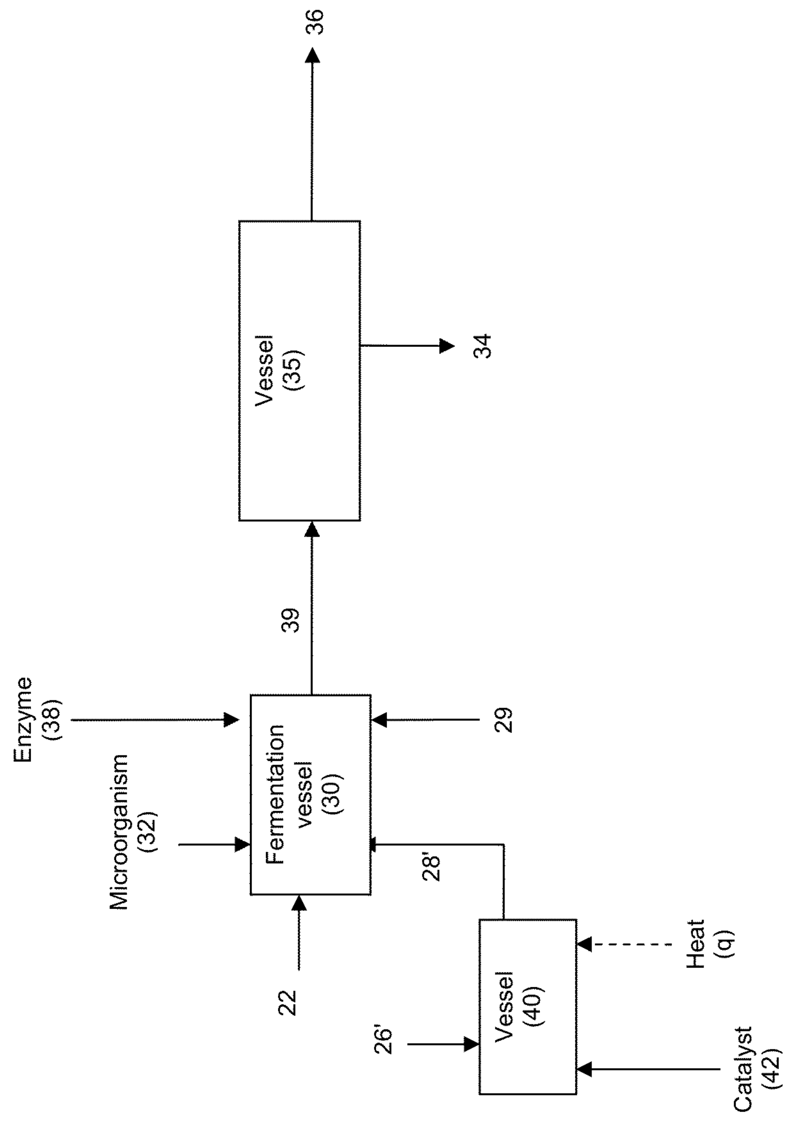

In still other embodiments, as shown, for example, in the embodiment of FIG. 5, a native oil 26' is supplied to a vessel 40 to which catalyst 42 is also supplied, whereby at least a portion of glycerides in oil 26' are hydrolyzed to form FFA 28'. Catalyst 42 can be subsequently inactivated, such as by the application of heat q. A product stream from vessel 40 containing FFA 28' and inactive catalyst 42 are then introduced into fermentation vessel 30, along with aqueous feedstock stream 22 in which feedstock oil 26, and in some embodiments, the undissolved solids have been previously removed by means of separator 20 (see, e.g., the embodiment of FIG. 4). Saccharification enzyme 38 and microorganism 32 are also introduced into fermentation vessel 30, whereby a product alcohol is produced by SSF.

Alternatively, oil 26' and catalyst 42 can be fed directly to fermentation vessel 30 in which oil 26' is hydrolyzed to FFA 28' rather than using vessel 40. Thereafter, active catalyst 42 can be subjected to heat q and inactivated while in the fermentation vessel before inoculation of microorganism 32. Alternatively, FFA 28' and active catalyst 42 can be fed to fermentation vessel 30 from vessel 40, and active catalyst 42 can thereafter be subjected to heat q and inactivated while in the fermentation vessel before inoculation of microorganism 32. In such embodiments, feedstock slurry 16 including oil 26, rather than stream 22 in which oil 26 was removed, can be fed to fermentation vessel 30 and contacted with active catalyst 42. Active catalyst 42 can therefore be used to hydrolyze oil 26 into FFA 28, thereby reducing the loss and/or degradation of the partition coefficient of the extractant over time that is attributable to the presence of the oil in the fermentation vessel.

In some embodiments, the system and processes of FIG. 5 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 2).

In some embodiments, native oil 26' can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, vegetable oil blends, and mixtures thereof. In some embodiments, native oil 26' is a mixture of two or more native oils, for example, a mixture of palm and soybean oils. In some embodiments, native oil 26' is a plant-derived oil. In some embodiments, the plant-derived oil can be, though not necessarily, derived from biomass that can be used in a fermentation process. The biomass can be the same or different source from which feedstock 12 (shown in FIG. 5 as stream 22) is obtained. Thus, for example, in some embodiments, oil 26' can be derived from corn, whereas feedstock 12 can be cane. For example, in some embodiments, oil 26' can be derived from corn, and the biomass source of feedstock 12 is also corn. Any possible combination of different biomass sources for oil 26' versus feedstock 12 can be used, as should be apparent to one of skill in the art.

FFA 28' can serve as an ISPR extractant 28' to form a two-phase mixture including an aqueous phase and an organic phase, with the product alcohol produced in the fermentation medium preferentially partitioning into the organic phase constituted by ISPR extractant 28'. In some embodiments, one or more additional ISPR extractants 29 can be introduced into fermentation vessel 30 as described above with reference to FIG. 1. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced in separator 50 for recovery of product alcohol 54 and optional recycle of recovered extractant 27 as shown in FIG. 1. The remaining process operations of the embodiment of FIG. 5 are identical to FIG. 1 and therefore, will not be described in detail again.

Figure 6:
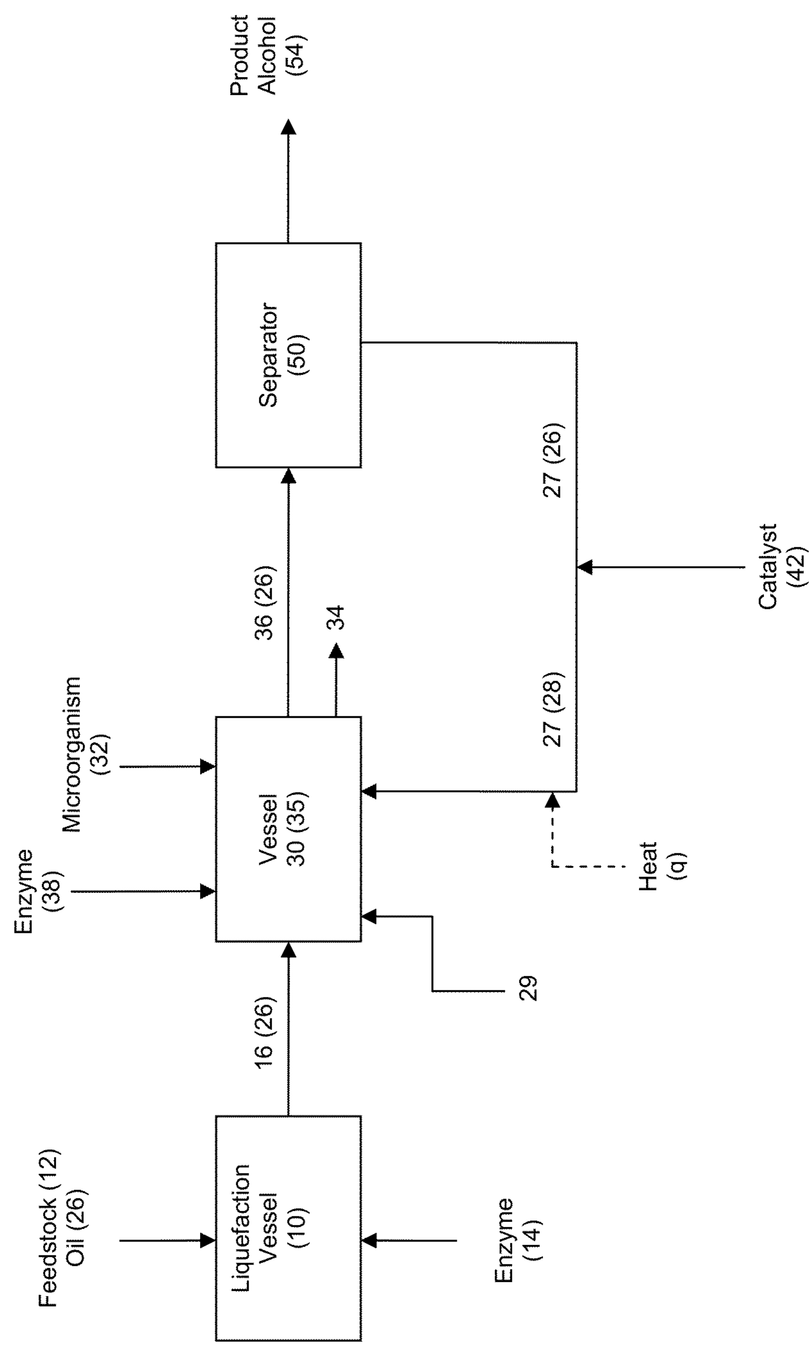

In some embodiments of the present invention, biomass oil present in feedstock 12 can be converted to FFA 28 at a step following alcoholic fermentation. FFA 28 can then be introduced as ISPR extractant 28 in the fermentation vessel. For example, in the embodiment of FIG. 6, feedstock 12 is liquefied to produced feedstock slurry 16 which includes oil 26 derived from the feedstock. Feedstock slurry 16 can also include undissolved solids from the feedstock. Alternatively, the undissolved solids can be separated from slurry 16 via a separator, such as a centrifuge (not shown). Feedstock slurry 16 containing oil 26 is introduced directly to fermentation vessel 30 containing a fermentation broth including saccharification enzyme 38 and microorganism 32. A product alcohol is produced by SSF in fermentation vessel 30. Alternatively, in some embodiments, the process can be modified to include a separate saccharification vessel as discussed in connection with FIG. 2.

ISPR extractant 29 is introduced to fermentation vessel 30 to form a biphasic mixture, and the product alcohol is removed by partitioning into the organic phase of the ISPR extractant 29. Oil 26 also partitions into the organic phase. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Organic phase stream 36 including oil 26 is introduced into separator 50 to recover product alcohol 54 from extractant 29. The resulting alcohol-lean extractant 27 includes recovered extractant 29 and oil 26. Extractant 27 is contacted with catalyst 42, whereby at least a portion of glycerides in oil 26 are hydrolyzed to form FFA 28. Heat q can then be applied to extractant 27 including FFA 28 so as to inactivate catalyst 42 before being recycled back into fermentation vessel 30. Such recycled extractant stream 27 can be a separate stream or a combined stream with fresh, make-up extractant stream 29. The subsequent withdrawal of alcohol-containing organic phase 36 from fermentation vessel 30 can then include FFA 28 and ISPR extractant 29 (as fresh extractant 29 and recycled extractant 27), in addition to the product alcohol and additional oil 26 from newly introduced feedstock slurry 16. Organic phase 36 can then be treated to recover the product alcohol, and recycled back into fermentation vessel 30 after contacting with catalyst 42 for hydrolysis of additional oil 26, in the same manner as just described. In some embodiments, use of make-up ISPR extractant 29 can be phased out as the fermentation process is operated over time because the process itself can produce FFA 28 as a make-up ISPR extractant for extracting the product alcohol. Thus, the ISPR extractant can be the stream of recycled extractant 27 with FFA 28.

Thus, FIGS. 1-5 provide various non-limiting embodiments of methods and systems involving fermentation processes and FFAs 28 produced from catalytic hydrolysis of biomass derived oil 26, and FFAs 28' produced from catalytic hydrolysis of native oil 26' such as plant-derived oil that can be used as ISPR extractants 28 and 28' to remove product alcohol in extractive fermentation.

In some embodiments, including any of the aforementioned embodiments described with reference to FIGS. 1-6, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose; oligosaccharides such as lactose, maltose, or sucrose; polysaccharides such as starch or cellulose; or mixtures thereof, and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C*1 *Compd*., [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described in, for example, in U.S. Patent Application Publication No. 2007/0031918 A1, which is herein incorporated by reference. In addition to an appropriate carbon source (from aqueous stream 22), fermentation broth must contain suitable minerals, salts, cofactors, buffers and other components, known to those skilled in the art, suitable for the growth of the cultures and promotion of an enzymatic pathway comprising a dihydroxyacid dehydratase (DHAD).

Recombinant microorganisms that produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula*, or *Saccharomyces*. In one embodiment, recombinant microorganisms can be selected from the group consisting of *Escherichia coli, Lactobacillus plantarum*, and *Saccharomyces cerevisiae*. In one embodiment, the recombinant microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*. For example, the production of butanol utilizing fermentation with a microorganism, as well as which microorganisms produce butanol, is known and is disclosed, for example, in U.S. Patent Application Publication No. 2009/0305370, herein incorporated by reference. In some embodiments, microorganisms comprise a butanol biosynthetic pathway. Suitable isobutanol biosynthetic pathways are known in the art (see, e.g., U.S. Patent Application Publication No. 2007/0092957, herein incorporated by reference). In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in U.S. Patent Application Publication No. 2009/0305363, herein incorporated by reference.

Construction of certain strains, including those used in the Examples, is provided herein.

Construction of *Saccharomyces cerevisiae* Strain BP1083 ("NGCI-070")

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-IoxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-IoxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 μg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from

*Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccaromyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccaromyces cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 143) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 144) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 145) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of Strains NYLA74, NYLA83, and NYLA84

Insertion-inactivation of endogenous PDC1 and PDC6 genes of *S. cerevisiae*. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from *Achromobacter xylosoxidans* (disclosed in U.S. Patent Application Publication No. 2009/0269823) was cloned. The coding region of this gene called sadB for secondary alcohol dehydrogenase (SEQ ID NO: 69) was amplified using standard conditions from A. xylosoxidans genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in *Saccharomyces cerevisiae* (Ma, et al., Gene 58:201-216, 1987) as follows. The yeast-*E. coli* shuttle vector pRS425::GPM::kivD::ADH which contains the GPM1 promoter (SEQ ID NO: 72), kivD coding region from *Lactococcus* lactis (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 μg of the remaining vector fragment was transformed into *S. cerevisiae* strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6:: PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO:80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH1t.

Construction of pdc1:: PPDC1-ilvD Integration Cassette and PDC1 Deletion:

A pdc1:: PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: PGPM1-sadB-ADH1t pdc1:: PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: PGPM1-sadB-ADH1t pdc1:: PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6:: PGPM1-sadB-ADH1t pdc1:: PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (Hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6:: PGPM1-sadB-ADH1t pdc1:: PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6:: PGPM1-sadB-ADH1t pdc1:: PPDC1-ilvD-FBA1t Δhis3 Δhxk2 pdc5::kanMX4.

Plasmid vectors pLH468 and pLH532 were simultaneously transformed into strain NYLA84 (BY4700 pdc6:: PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus lactis* (nt 9249-10895) expressed from the TDH3 promoter (nt 10896-11918) followed by the TDH3 terminator (nt 8237-9235) for expression of KivD.

Coding regions for *Lactococcus lactis* ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058,970, Example 3, which is herein incorporated by reference. pRS425::GPM-sadB is the pRS425 vector (ATCC No. 77106) with a chimeric gene containing the GPM1 promoter (SEQ ID NO:72), coding region from a butanol dehydrogenase of *Achromobacter xylosoxidans* (sadB; DNA SEQ ID NO: 69; protein SEQ ID NO:70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-NotI fragment from pLH435 that contains the PGPM1-Hadhy-ADH1t cassette in a triple ligation reaction. This yielded the vector pRS411::PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the IlvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-ilvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-ilvD (*Streptococcus mutans*)-Lumio. This generated vector pLH468 (pRS423::PFBA1-ilvD(Strep) Lumio-FBA1t-PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KARI in yeast. pLH532 is a pHR81 vector (ATCC No. 87541) containing the following chimeric genes: 1) the CUP1 promoter (SEQ ID NO: 139), acetolactate synthase coding region from *Bacillus subtilis*

(AlsS; SEQ ID NO: 137; protein SEQ ID NO: 138) and CYC1 terminator2 (SEQ ID NO: 133); 2) an ILV5 promoter (SEQ ID NO: 134), Pf5.IlvC coding region (SEQ ID NO: 132) and ILV5 terminator (SEQ ID NO: 135); and 3) the FBA1 promoter (SEQ ID NO: 136), *S. cerevisiae* KARI coding region (ILV5; SEQ ID NO: 131); and CYC1 terminator.

The Pf5.IlvC coding region is a sequence encoding KARI derived from *Pseudomonas fluorescens* that was described in U.S. Patent Application Publication No. 2009/0163376, which is herein incorporated by reference.

The Pf5.IlvC coding region was synthesized by DNA2.0, Inc. (Menlo Park, Calif.; SEQ ID NO: 132) based on codons that were optimized for expression in *Saccharomyces cerevisiae.* pYZ090 Construction pYZ090 (SEQ ID NO: 1) is based on the pHR81 (ATCC No. 87541) backbone and was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus* lactis (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 Construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "μL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods

Seed Flask Growth

A *Saccharomyces cerevisiae* strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 26° C. in an incubator rotating at 300 rpm. The frozen culture was previously stored at −80° C. The composition of the first seed flask medium was:

3.0 g/L dextrose 3.0 g/L ethanol, anhydrous 3.7 g/L ForMedium™ Synthetic Complete Amino Acid (Kaiser) Drop-Out: without HIS, without URA (Reference No. DSCK162CK)

6.7 g/L Difco Yeast Nitrogen Base without amino acids (No. 291920)

Twelve milliliters from the first seed flask culture was transferred to a 2 L flask and grown at 30° C. in an incubator rotating at 300 rpm. The second seed flask has 220 mL of the following medium:

30.0 g/L dextrose 5.0 g/L ethanol, anhydrous 3.7 g/L ForMedium™ Synthetic Complete Amino Acid (Kaiser) Drop-Out: without HIS, without URA (Reference No. DSCK162CK)

6.7 g/L Difco Yeast Nitrogen Base without amino acids (No. 291920)

0.2 M MES Buffer titrated to pH 5.5-6.0

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 300 mL of 0.2 uM filter sterilized Cognis, 90-95% oleyl alcohol was added to the flask. The culture continues to grow to >4 g/L dcw ($OD_{600}$>10) before being harvested and added to the fermentation.

Fermentation Preparation

Initial Fermentation Vessel Preparation

A glass jacked, 2 L fermentation vessel (Sartorius AG, Goettingen, Germany) was charged with house water to 66% of the liquefaction weight. A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (6.36 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a $\alpha$-amylase (glucoamylase). The glucose was kept excess (1-50 g/L) for as long as starch was available for saccharification.

Analytical

Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
|---|---|---|
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Biomass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 μL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 μL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 μL) was drawn of the final Trypan Blue dilution with an m20 Variable Channel BioHit pipette with 2-20 μL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 μL of sample was transferred with a m1000 Variable Channel BioHit pipette with 100-1000 μL BioHit pipette tips into a 0.2 um centrifuge filter (Nanosep® MF modified nylon centrifuge filter), then centrifuged using a Eppendorf, 5415C for five minutes at 14,000 rpm. Approximately 200 μL of filtered sample was transferred into a 1.8 auto sampler vial with a 250 μL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and R1 detector. The column used was an Aminex HPX-87H, 300×7.8 with a Bio-Rad Cation H refill, 30×4.6 guard column. Column temperature was 40° C., with a mobile phase of 0.01 N sulfuric acid, at a flow rate of 0.6 mL/min for 40 minutes. Results are shown in Table 1.

TABLE 1

Retention times of fermentation products in aqueous phase

| HPLC 302/310 Normalized to 10 μL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 μL of sample was transferred using a m1000 Variable Channel BioHit pipette with 100-1000 μL BioHit pipette tips into a 1.8 auto sampler vial with a 250 μL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 μm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

Retention times of fermentation products in solvent phase.

| GC 302/310 Normalized to 10 μL injections | FW | Solvent Retention Time, min | Range of Standards, g/L |
|---|---|---|---|
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 μm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14.

| Example # | Experimental Identifier | Lipase | Max cell Count $\times 10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post-liquefaction | 17.2 | 0.25 |
| 5 | 2010Y018 | 7.2 ppm | 16.2 | 5 | Oleyl alcohol | post-liquefaction | 45.8 | 0.66 |
| 6 | 2010Y019 | none | 17.5 | 5 | Oleyl alcohol | post-liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |
| 13 | 2010Y031 | 10 ppm | 12.8 | 0 | Corn Oil Fatty Acids | none | 18.86 | 0.35 |

TABLE 3-continued

| Fermentation conditions for Examples 1-14. | | | | | | | | |
|---|---|---|---|---|---|---|---|---|
| Example # | Experimental Identifier | Lipase | Max cell Count $\times 10^7$ | Ethanol g/L | Solvent | Heat Kill Lipase | Eff Iso Titer g/L* | max Eff Iso rate g/L/h |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume Example 15

The experimental identifier was GLNOR432A. NYLA74 (a butanediol producer—NGCI-047) was grown in 25 mL of medium in a 250 mL flask from a frozen vial to ~1 OD. The pre-seed culture was transferred to a 2 L flask and grown to 1.7-1.8 OD. The medium for both flasks was:

3.0 g/L dextrose
3.0 g/L ethanol, anhydrous
6.7 g/L Difco Yeast Nitrogen Base without amino acids (No. 291920)
1.4 g/L Yeast Dropout Mix (Sigma Y2001)
10 mL/L 1% w/v L-Leucine stock solution
2 mL/L 1% w/v L-Tryptophan stock solution A 1 L, Applikon fermentation vessel was inoculated with 60 mL of the seed flask. The fermentation vessel contained 700 mL of the following sterile medium:

20.0 g/L dextrose
8.0 mL/L ethanol, anhydrous
6.7 g/L Difco Yeast Nitrogen Base without amino acids (No. 291920)
2.8 g/L Yeast Dropout Mix (Sigma Y2001)
20 mL/L 1% w/v L-Leucine stock solution
4 mL/L 1% w/v L-Tryptophan stock solution
0.5 mL Sigma 204 Antifoam
0.8 mL/L 1% w/v Ergesterol solution in 1:1::Tween 80:Ethanol The residual glucose was kept excess with a 50% w/w glucose solution. The dissolved oxygen concentration of the fermentation vessel was controlled at 30% with stir control. The pH was controlled at pH=5.5. The fermentation vessel was sparged with 0.3 slpm of sterile, house air. The temperature was controlled at 30° C.

Example 16

The experimental identifier was GLNOR434A. This example is the same as example 15 with the exception of the addition of 3 g of oleic acid and the addition of 3 g of palmitic acid prior to inoculation. NYLA74 (a butanediol producer—NGCI-047) was the biocatalyst.

Figure 7:
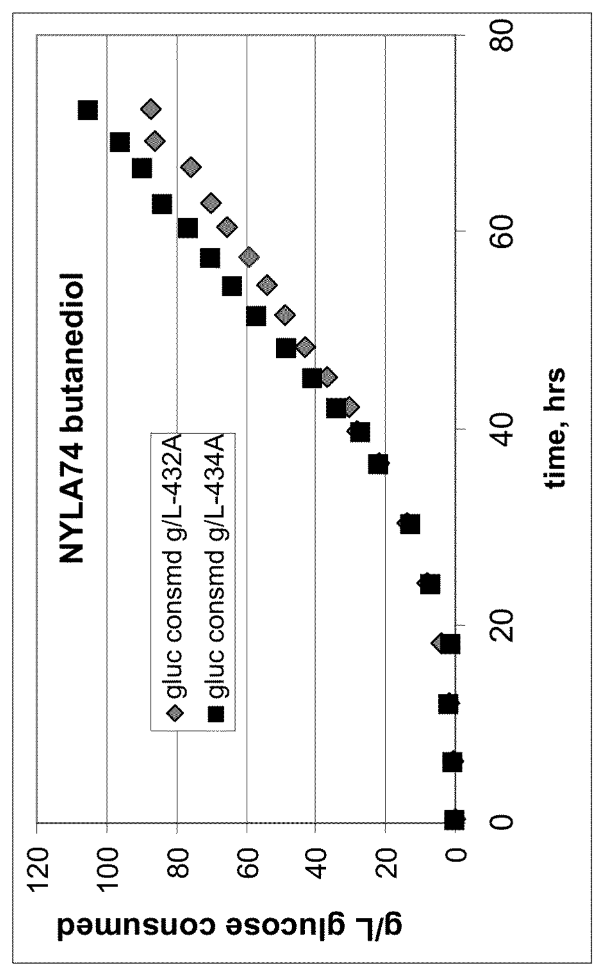
FIG. 7 is a chart illustrating the effect that the presence of fatty acids in a fermentation vessel has on glucose consumption for butanologen strain NGCI-047.

FIG. 7 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 17

The experimental identifier was GLNOR435A. This example was the same as example 15 except it was inoculated with NYLA74 (an isobutanol producer—NGCI-049).

Example 18

The experimental identifier was GLNOR437A. This example was the same as Example 16 except it was inoculated with NYLA74 (an isobutanol producer) (NGCI-049).

Figure 8:
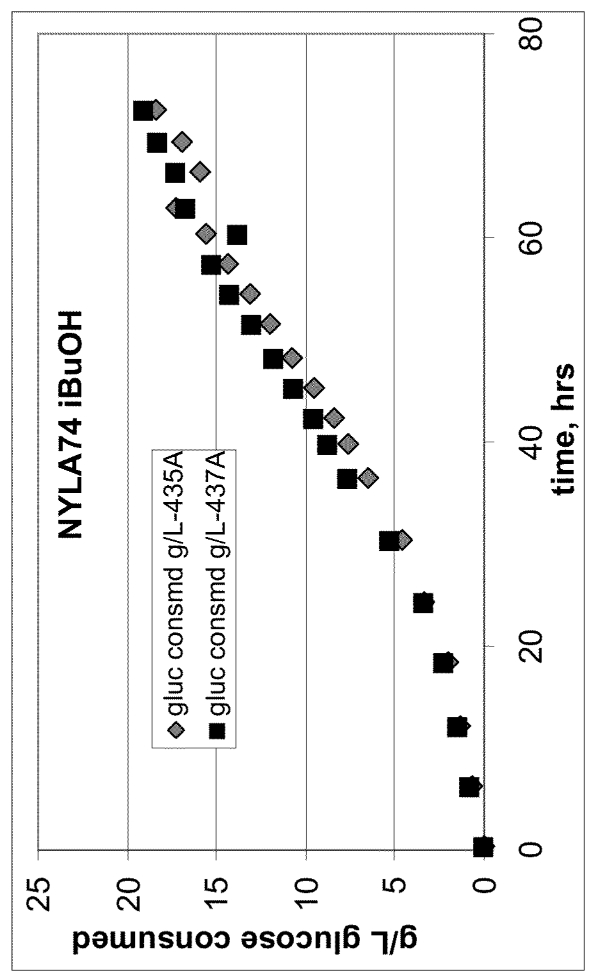
FIG. 8 is a chart illustrating the effect that the presence of fatty acids in a fermentation vessel has on glucose consumption for butanologen strain NGCI-049.

FIG. 8 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 19

The experimental identifier was 090420_3212. This example was run similarly to Example 15 except it was inoculated with butanologen NYLA84 (an isobutanol producer). This fermentation was run in a 1 L Sartorius fermentation vessel.

Example 20

The experimental identifier was 2009Y047. This example was run similarly to Example 16 except it was inoculated with butanologen NYLA84 (an isobutanol producer). This fermentation was run in a 1 L Sartorius fermentation.

Figure 9:
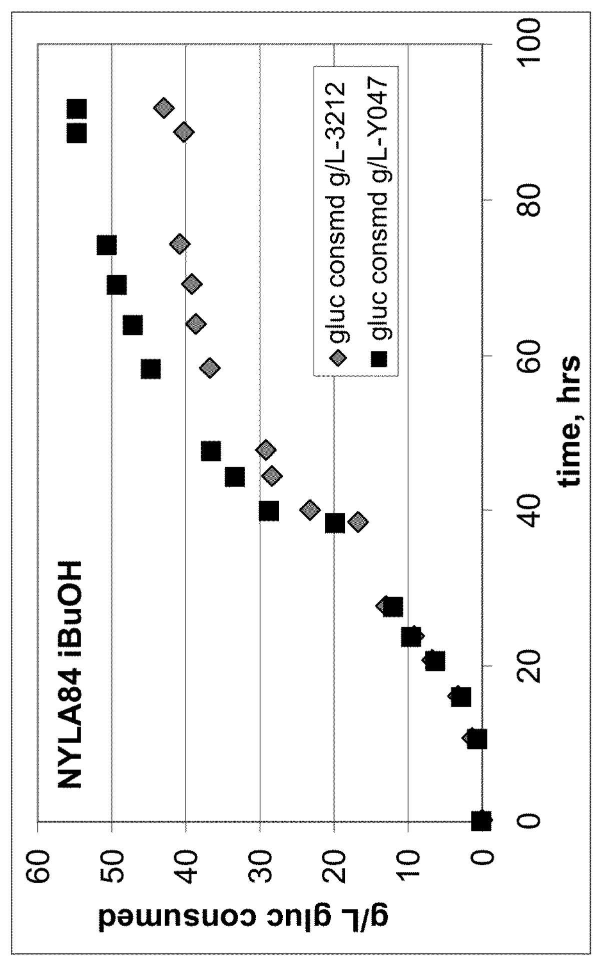
FIG. 9 is a chart illustrating the effect that the presence of fatty acids in a fermentation vessel has on glucose consumption for butanologen strain NYLA84.

FIG. 9 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Table 4 shows +/−fatty acid addition, maximum optical density, and g/L glucose consumed.

TABLE 4

| Example # | Experimental Identifier | Strain | Fatty Acids Added | Product | 69 hours $OD_{600}$ | 69 hours g/L glucose consumed |
|---|---|---|---|---|---|---|
| 15 | GLNOR432A | NYLA74 | − | butanediol | 12.8 | 86.0 |
| 16 | GLNOR434A | NYLA74 | + | butanediol | 23.1 | 95.9 |
| 17 | GLNOR435A | NYLA74 | − | isobutanol | 2.4 | 16.9 |
| 18 | GLNOR437A | NYLA74 | + | isobutanol | 4.5 | 18.3 |
| 19 | 090420_3212 | NYLA84 | − | isobutanol | 9.6 | 39.3 |
| 20 | 2009Y047 | NYLA84 | + | isobutanol | 20.2 | 49.1 |

Example 21

Lipase Treatment of Liquefied Corn Mash for Simultaneous Saccharification and Fermentation with In-Situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash. Results are shown in Table 5.

TABLE 5

Lipid and free fatty acid content of fermentations containing oleyl alcohol as ISPR solvent and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 22

Heat Inactivation of Lipase in Lipase-treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 6.

TABLE 6

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, | 6 h, liq. mash | 0.08 | 0.71 | 41 | 345 | 386 | 89 |
| no 85° C. heat treatment | 25 h, liq. mash | 0.22 | 0.06 | 105 | 27 | 132 | 20 |
| | 25 h, OA | 0.58 | 0.39 | 212 | 143 | 355 | 40 |
| | 73 h, liq. mash | 0.25 | 0.05 | 121 | 22 | 143 | 18 |
| | 73 h, OA | 0.91 | 0.24 | 333 | 88 | 420 | 21 |
| 10 ppm inactive lipase, | 6 h, liq. mash | 0.06 | 0.45 | 28 | 224 | 252 | 89 |
| 85° C. heat treatment | 25 h, liq. mash | 0.10 | 0.11 | 49 | 54 | 103 | 53 |
| | 25 h, OA | 0.02 | 0.96 | 8 | 366 | 374 | 99 |
| | 73 h, liq. mash | 0.24 | 0.15 | 117 | 72 | 189 | 62 |
| | 73 h, OA | 0.06 | 1.11 | 23 | 424 | 447 | 95 |
| no lipase, | 6 h, liq. mash | 0.80 | 0.40 | 401 | 199 | 599 | 33 |
| no 85° C. heat treatment | 25 h, liq. mash | 0.30 | 0.05 | 147 | 25 | 173 | 15 |
| | 25 h, OA | 0.55 | 0.36 | 212 | 139 | 351 | 40 |
| | 73 h, liq. mash | 0.23 | 0.05 | 117 | 26 | 143 | 23 |
| | 73 h, OA | 0.79 | 0.42 | 305 | 162 | 467 | 34 |
| no lipase, | 6 h, liq. mash | 0.74 | 0.36 | 370 | 183 | 553 | 33 |
| 85° C. heat treatment | 25 h, liq. mash | 0.31 | 0.05 | 156 | 27 | 183 | 15 |
| | 25 h, OA | 0.60 | 0.35 | 233 | 136 | 369 | 37 |
| | 73 h, liq. mash | 0.20 | 0.05 | 99 | 23 | 121 | 23 |
| | 73 h, OA | 0.84 | 0.41 | 326 | 159 | 486 | 33 |

Example 23

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 7.

TABLE 7

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |

TABLE 7-continued

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

Example 24

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100L Solution (21 mg total soluble protein, 10 ppm lipase final concentration) and to the second mixture was added 1.05 mL of aqueous solution of Lipolase® 100L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 8.

TABLE 8

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase at 55° C. prior to liquefaction at 85° C., mix with OA for 20 h | 1 h, pre-liquefaction | 0.226 | 0.627 | 112 | 311 | 424 | 74 |
| | 2 h, pre-liquefaction | 0.199 | 0.650 | 99 | 323 | 422 | 77 |
| | 4 h, pre-liquefaction | 0.151 | 0.673 | 75 | 334 | 410 | 82 |
| | 6 h, pre-liquefaction | 0.101 | 0.700 | 50 | 348 | 398 | 87 |
| | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase at 55° C. prior to liquefaction at 85° C., mix with OA for 20 h | 1 h, pre-liquefaction | 0.408 | 0.480 | 226 | 266 | 492 | 54 |
| | 2 h, pre-liquefaction | 0.401 | 0.424 | 222 | 235 | 457 | 51 |
| | 4 h, pre-liquefaction | 0.299 | 0.433 | 165 | 240 | 405 | 58 |
| | 6 h, pre-liquefaction | 0.346 | 0.453 | 192 | 251 | 442 | 57 |
| | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

Example 25

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 9.

TABLE 9

Percent free fatty acid content (% FFA) of a mixture of ground whole corn kernels using lipase treatment at 55° C. prior to liquefaction

| | % FFA time | | | | |
|---|---|---|---|---|---|
| | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |
| Novozyme ® CALA L | 37 | 40 | 44 | 44 | 45 |
| Palatase ® 20000L | 37 | 49 | 59 | 62 | 66 |
| no enzyme | 38 | 33 | 37 | 41 | 42 |

Example 26

Lipase treatment of Ground Whole Corn Kernels prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The % FFA in the OA phase of the fermentation run according to Examples 7 and 10 (with heat inactivation of lipase prior to fermentation) was 97% at 70 h (end of run (EOR)), compared to only 49% FFA for the fermentation run according to Example 8 where ground whole corn kernels had not been treated with lipase prior to liquefaction. Results are shown in Table 10.

TABLE 10

Lipid and free fatty acid content of fermentations containing oleyl alcohol as ISPR solvent and heat-inactivated lipase (lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 27

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH present in the COFA phase of the fermentations containing inactive lipase. The final total grams of isobutanol (i-BuOH) present in the fermentation broths containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 11 and 12.

TABLE 11

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9 | 4.5 | 2.4 | 0.0 | 0 | 2.4 |
| Example 9 | 28.8 | 5.4 | 70.9 | 16.5 | 22.0 |
| Example 9 | 52.4 | 8.9 | 199.0 | 46.4 | 55.3 |
| Example 9 | 69.3 | 4.9 | 230.9 | 53.9 | 69.3 |
| Example 11 | 6.6 | 2.3 | 0.0 | 0.0 | 2.3 |
| Example 11 | 53.5 | 25.1 | 2.9 | 0.6 | 25.7 |
| Example 11 | 71.1 | 24.4 | 6.3 | 1.4 | 25.8 |
| Example 12 | 6.6 | 2.3 | 0.0 | 0.0 | 2.3 |
| Example 12 | 53.5 | 12.8 | 1.6 | 0.4 | 13.2 |
| Example 12 | 71.1 | 12.8 | 3.0 | 0.7 | 13.5 |
| Example 13 | 6.6 | 2.3 | 0.0 | 0.0 | 2.3 |
| Example 13 | 53.5 | 4.9 | 72.1 | 16.0 | 20.9 |
| Example 13 | 71.1 | 4.6 | 91.4 | 20.3 | 24.9 |
| Example 14 | 6.6 | 2.1 | 0.0 | 0.0 | 2.1 |
| Example 14 | 53.5 | 9.8 | 197.2 | 43.8 | 53.6 |
| Example 14 | 71.1 | 4.9 | 244.5 | 54.3 | 59.2 |

TABLE 12

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (fermentation broth analysis)

| sample | fermentation time (h) | g i-BuOH/ kg broth | g FABE/ kg broth | g i-BuOH from FABE/ kg broth | total g i-BuOH/ kg broth |
|---|---|---|---|---|---|
| Example 9 | 4.5 | 0.0 | 0.0 | 0 | 0 |
| Example 9 | 28.8 | 0.0 | 12.6 | 2.9 | 2.9 |
| Example 9 | 52.4 | 0.0 | 30.3 | 7.1 | 7.1 |
| Example 9 | 69.3 | 0.0 | 24.7 | 5.8 | 5.8 |
| Example 11 | 6.6 | 0.0 | 0.0 | 0 | 0.0 |
| Example 11 | 53.5 | 9.8 | 0.0 | 0 | 9.8 |
| Example 11 | 71.1 | 9.5 | 0.0 | 0 | 9.5 |
| Example 12 | 6.6 | 0.0 | 0.0 | 0 | 0 |
| Example 12 | 53.5 | 3.8 | 0.0 | 0.0 | 3.8 |
| Example 12 | 71.1 | 5.1 | 0.0 | 0.0 | 5.1 |
| Example 13 | 6.6 | 0.0 | 0.0 | 0 | 0 |
| Example 13 | 53.5 | 2.1 | 3.0 | 0.7 | 2.8 |
| Example 13 | 71.1 | 2.1 | 7.4 | 1.6 | 3.7 |
| Example 14 | 6.6 | 0.0 | 0.0 | 0 | 0.0 |
| Example 14 | 53.5 | 2.9 | 22.4 | 5.0 | 7.9 |
| Example 14 | 71.1 | 3.3 | 19.3 | 4.3 | 7.6 |

Example 28

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol), lipase (Lipolase® 100 L; Novozymes) and corn oil fatty acids prepared from corn oil (Table 13) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (1-BuO-COFA) (Table 14).

TABLE 13

Reaction conditions for conversion of isobutanol (i-BuOH) to isobutyl esters of corn oil fatty acids (i-BuO-COFA)

| reaction | MES (0.2M) (g) | i-BuOH (g) | COFA (g) | lipase (ppm) |
|---|---|---|---|---|
| 1 | 45.96 | 3.6 | 43.4 | 10 |
| 2 | 45.96 | 3.6 | 21.7 | 10 |
| 3 | 45.96 | 3.6 | 10.85 | 10 |
| 4 | 45.96 | 3.6 | 43.4 | 4 |
| 5 | 45.96 | 3.6 | 43.4 | 0 |

TABLE 14

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1 | 0.76 | 2.84 | 2.58 | 0.25 | 1.13 |

TABLE 14-continued

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 2 | 0.74 | 2.86 | 2.41 | 0.44 | 2.00 |
| 1 | 4 | 0.66 | 2.94 | 2.05 | 0.89 | 4.03 |
| 1 | 6 | 0.63 | 2.97 | 1.43 | 1.54 | 6.93 |
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 29

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 15) were stirred at 30° C., and samples were withdrawn from each reaction mixture at predetermined times, immediately centrifuged, and the aqueous and organic layers separated and analyzed for isobutanol (i-BuOH) or n-butanol (n-BuOH) and isobutyl- or butyl esters of corn oil fatty acids (BuO-COFA) (Table 16).

TABLE 15

Reaction conditions for conversion of isobutanol (i-BuOH) or n-butanol (n-BuOH) to butyl esters of corn oil fatty acids (BuO-COFA)

| reaction | butanol | MES(0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 16

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| reaction | time (h) | total i-BuOH (g) (AQ) | total i-BuOH (g) (ORG) | total i-BuOH (g) (ORG) | i-BuOH (g) (ORG) | i-BuOH from i-BuO-COFA (g) (ORG) |
|---|---|---|---|---|---|---|
| 6 | 0 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |
| | | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
| 7 | 0 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |
| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
| 8 | 0 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |
| 9 | 0 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 30

Production of Iso-Butyl Oleate by Lipase-Catalyzed Reaction of Iso-Butanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 17) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 18).

TABLE 17

Reaction conditions for conversion of isobutanol (i-BuOH) to iso-butyl oleate (i-BuO-oleate)

| reaction | MES (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 18

Weights of isobutanol (i-BuOH) and iso-butyl oleate (i-BuO-COFA) present in the aqueous fraction (AQ) and organic fraction (ORG) for reactions described in Table 17.

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |

TABLE 18-continued

Weights of isobutanol (i-BuOH) and iso-butyl oleate (i-BuO-COFA) present in the aqueous fraction (AQ) and organic fraction (ORG) for reactions described in Table 17.

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 51 | 0.82 | 2.83 | 0.54 | 2.29 | 10.5 |
| 11 | 0 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 31

Production of Iso-Butyl Oleate by Lipase-Catalyzed Reaction of Iso-Butanol and Oleic Acid Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100L, Lipex® 100L, Lipozyme® CALB L, Novozyme® CALA L, Palatase® from Novozymes, or lipase (10 ppm) from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* from SigmaAldrich (Table 19), were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 20).

TABLE 19

Reaction conditions for conversion of isobutanol (i-BuOH) to iso-butyl oleate (i-BuO-oleate)

| MES (0.2M) (g) | i-BuOH (g) | oleic acid (g) | lipase (ppm) |
|---|---|---|---|
| 46.105 | 3.601 | 13.72 | 10 |

TABLE 20

Weights of isobutanol (i-BuOH) and iso-butyl oleate (i-BuO-oleate) present in the aqueous fraction (AQ) and organic fraction (ORG) for reactions described in Table 19

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100L | 23 | 1.55 | 2.05 | 1.47 | 0.59 | 2.68 |
| Lipex ® 100L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| *Pseudomonas fluorescens* | 23 | 1.38 | 2.22 | 1.97 | 0.25 | 1.14 |
| *Pseudomonas cepacia* | 23 | 1.39 | 2.21 | 1.95 | 0.26 | 1.20 |
| *Mucor miehei* | 23 | 1.29 | 2.31 | 1.57 | 0.75 | 3.42 |
| hog pancreas | 23 | 1.40 | 2.20 | 2.19 | 0.01 | 0.04 |
| *Candida cylindracea* | 23 | 1.15 | 2.45 | 1.08 | 1.37 | 6.25 |
| *Rhizopus niveus* | 23 | 1.39 | 2.21 | 2.19 | 0.02 | 0.11 |
| *Candida antarctica* | 23 | 1.37 | 2.24 | 2.08 | 0.15 | 0.69 |
| *Rhizopus arrhizus* | 23 | 1.01 | 2.59 | 0.81 | 1.78 | 8.12 |
| *Aspergillus* | 23 | 1.36 | 2.24 | 2.06 | 0.18 | 0.82 |

Example 32

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 21), and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 22).

TABLE 21

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 22

Weights of isobutanol (i-BuOH) and isobutyl esters of corn oil fatty acids (i-BuO-COFA) present in the aqueous fraction (AQ) and organic fraction (ORG) for reactions described in Table 21

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |
| 1 | 20 | 1.25 | 2.43 | 2.22 | 0.21 | 0.96 |
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 33

Comparison of Partition Coefficients for Isobutanol Between Water and Extractant Aqueous solutions of isobutanol (30 g/L) were mixed with corn oil fatty acids (COFA), oleic acid, or corn oil triglycerides, and their measured partition coefficients reported in the table relative to the measured partition coefficient for oleyl alcohol. Results are shown in Table 23.

TABLE 23

Relative partition coefficients for isobutanol (30 g/L) between water and extractant

| extractant | isobutanol partition coefficient, relative to oleyl alcohol |
|---|---|
| oleyl alcohol | 100% |
| corn oil fatty acids | 91% |
| corn oil fatty acid isobutyl esters | 43% |
| corn oil triglycerides | 10% |

Example 34

Hydroxylated Triglycerides from Corn Oil

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1$H NMR analysis of the crude reaction product showed that 63% of double bonds were epoxidized.

A. Corn Oil Hydroxylation (63% Hydroxylation)

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1$H NMR analysis of the crude reaction product showed that 63% of double bonds were epoxidized.

To a 500 mL round bottom flask was added epoxidized corn oil (20.0 g), tetrahydrofuran (THF) (100.0 mL), and sulfuric acid (50 mL of 1.7 M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.9 g of dark yellow oil (63% hydroxylation corn oil).

B. Corn Oil Hydroxylation (47% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for one hour, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 49.8 g of yellow oil. The $^1$H NMR analysis of the crude reaction product showed that 47% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.2 g of dark yellow oil (47% hydroxylation corn oil).

C. Corn Oil Hydroxylation (28% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 47.2 g of yellow oil. The $^{1}H$ NMR analysis of the crude reaction product showed that 28% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 20.3 g of dark yellow oil (28% hydroxylation corn oil).

Partition Coefficient Measurement

To a 5 mL vial was added 0.910 g of the 67% hydroxylated corn oil, and 0.910 mL of 3 wt % i-BuOH water solution. The biphasic mixture was vigorously stirred using Vortex Genie® for 10 minutes. Upon mixing, the separation of layers was aided by centrifuging the mixture using Fisher Scientific Centrific 228 centrifuge (3300 rpm) for 10 minutes. 0.100 g of both layers were taken. The organic, upper layer was diluted to 1.00 mL with toluene solution of ethylene glycol diethylether (10.1 mg/mL), and the water layer was diluted to 1.00 mL with methanol solution of ethylene glycol diethylether (10.2 mg/mL). The concentrations of i-BuOH in both phases were measured using a calibrated gas chromatograph (GC). The same procedure was repeated for 47% and 28% hydroxylated corn oil. The partition coefficient thus measured was 3.2 for the 67% hydroxylated corn oil, 2.3 for the 47% hydroxylated corn oil, and 2.1 for the 28% hydroxylated corn oil.

The above outlined procedure was repeated with 6% i-BuOH water solution. The partition coefficients for 67%-, 47%-, and 28%-hydroxylated corn oils were 2.9, 2.9, and 2.0, respectively.

Example 34

Fatty Amides Plus Fatty Acids, and Pure Fatty Amides from Corn Oil

Corn oil was reacted with aqueous ammonium hydroxide in a manner similar to that described by Roe, et al., J. Am. Oil Chem. Soc. 29:18-22, 1952. Mazola® corn oil (0.818 L, 755 g) was placed in a 1 gallon stainless steel reactor to which was added 1.71 L (1540 g) of aqueous ammonium hydroxide (28% as $NH_3$). The reactor was heated with stirring to 160° C. and was maintained at that temperature with stirring for 7 h during which time the pressure reached 400 psi. The reactor was cooled and the product, a creamy white solid, was removed and the reactor rinsed with ethyl acetate. The product was dissolved in 5 L ethyl acetate and washed 5 times with 500 mL each of water which was neutralized with $H_2SO_4$. The ethyl acetate was then dried over anhydrous $Na_2SO_4$ and the solvent removed on a rotary evaporator leaving a light brown soft solid.

$^{13}C$ NMR in $CDCl_3$ indicated that the product contained an approximate 2:1 ratio of fatty amide to fatty acid and that the conversion of the corn oil to product was quantitative. The product had a melting point of 57-58° C., but dropped about 11° C. when saturated with water.

Pure corn oil fatty amide was synthesized from corn oil according to Kohlhase, et al., J. Am. Oil Chem. Soc. 48:265-270, 1971 using anhydrous ammonia with ammonium acetate as a catalyst.

Three grams of ammonium acetate were placed in a 400 mL stainless steel shaker tube to which was added 51.8 g of corn oil. Anhydrous ammonia (89.7 g) was then added and the reactor sealed and heated for 7 h at 125° C. during which time the pressure reached 1300 psi. The reactor was cooled, the light colored solid removed and the reactor rinsed with ethyl acetate. The product dissolved in ethyl acetate was then worked up as in the case of the fatty amide/fatty acid mixture above.

Fatty acids were synthesized from corn oil by base hydrolysis using NaOH. Round bottom flask (5L) was equipped with a mechanical stirrer, thermocouple, heating mantle, condenser, and nitrogen tee. Charged with 500 g of food grade corn oil, 1 L of water and 75 g of sodium hydroxide. Mixture was heated to 90° C. and held for three hours, during which time it became a single thick, emulsion-like single phase. At the end of this time, TLC shows no remaining corn oil in the mixture. The mixture was then cooled to 72° C. and 500 mL of 25% sulfuric acid was added to acidify the mixture. It was then cooled to room temperature and 2 L of diethyl ether was added. The ether layer was washed 3×1 L with 1% sulfuric acid, 1×1 L with saturated brine, dried over $MgSO_4$, and filtered. The ether was removed by rotovap and then the oil was purged with nitrogen overnight, obtaining 470 g of a yellow oil that partially crystallized overnight. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids Three preparations: (1) the 2:1 mixture of corn oil fatty amide and corn oil fatty acid from aqueous ammonia, (2) a 2:1 mixture of pure corn oil fatty amide:pure corn oil fatty acid, and (3) a 1:2 mixture of pure corn oil fatty amide:corn oil fatty acid, were all tested for their ability to extract isobutanol from a 3% solution in water. Seven hundred milligrams of each was added to 2.1 mL of water containing 3% isobutanol in a 20 mL scintillation vial and placed on a rotary shaker overnight at 30° C. In all three cases, the organic phase became liquid at this temperature, indicating a further lowering of the melting point with the uptake of isobutanol. Fifty microliters of the upper phase were diluted with either 200 μL of toluene containing ethylene glycol diethylether (10.068 mg/mL) as a GC standard or 200 μL of isopropanol containing the same concentration of ethylene glycol diethylether. Fifty microliters of the lower phase was diluted with 150 μL of methanol and 50 μL of isopropanol containing the same concentration of ethylene glycol diethylether. The concentrations of isobutanol in both phases were determined using a calibrated GC. The partition coefficients measured were as follows: 3.81 for (1), 4.31 for (2), and 3.58 for (3).

Fatty amide/fatty acid aqueous ammonia preparation (1), and a preparation (1a) constituted by preparation (1) mixed 1:1 with pure corn oil fatty acid (equivalent to 1:2 fatty amide: fatty acid) were incubated in shake flasks with fermentation broth containing the *Saccharomyces* butanologen NGCI-070 at a ratio of 3 parts broth to 1 part amide/acid mixture. Preparation (1) was a soft solid, while preparation (1a) was a liquid at 30° C. Starting at a glucose concentration of 8.35 g/L, the shake flasks were then incubated for 25 h on an incubator shaker and the consumption of glucose followed as a function of time. Table 24 indicates that the fatty amide/fatty acid mixtures at both ratios were not toxic to the butanologen and even showed higher rates of glucose uptake than with oleyl alcohol.

TABLE 24

| Flask | Glucose conc. (g/L) | | |
|---|---|---|---|
| | Time = 0 | 18 hrs | 25 hrs |
| Oleyl Alcohol | 8.35 | 4.26 | 0 |
| Oleyl Alcohol | 8.35 | 4.46 | 0 |
| 2:1 Synthesized Fatty Amide:Fatty Acid Mix (Preparation (1)) | 8.35 | 3.06 | 0 |
| 2:1 Synthesized Fatty Amide:Fatty Acid Mix (Preparation (1)) | 8.35 | 3.22 | 0 |
| 1:1 Synthesized Fatty Amide Fatty Acid Mix:Pure Fatty Acids (Preparation (1a)) | 8.35 | 2.73 | 0 |
| 1:1 Synthesized Fatty Amide Fatty Acid Mix:Pure Fatty Acids (Preparation (1a)) | 8.35 | 2.73 | 0 |

Example 35

Fatty Alcohols from Corn Oil

With reference to the reaction of Equation IV above for producing fatty alcohols from corn oil, a 22L, round-bottom flask equipped with a mechanical stirrer, reflux condenser with $N_2$ source, addition funnel, internal thermocouple, and rubber septum was flame-dried under nitrogen. The flask was charged with 132 g (3.30 moles) of 95% lithium aluminum hydride powder that is weighed out in a dry box and loaded into a solids addition funnel. The 22L flask was cooled with an ice bath, and 9.0 liters of anhydrous THF were added into the reactor via a cannula. The resulting slurry was cooled to 0-5° C. and a solution of 956 g (1.10 moles) of Wesson® corn oil in 1.00 liter of anhydrous THF was added dropwise over 2-3 hours while holding the reaction temperature at 5-20° C. After adding the corn oil, the slurry was stirred overnight at ambient temperature. When the reaction was done, as verified by TLC chromatography, it was quenched by the dropwise addition of a solution of 130 g of water dissolved in 370 mL of THF. Then 130 g of 15% aqueous NaOH solution was added followed by the addition of 400 g of water. The mixture was vigorously stirred while warming to room temperature and produced a white granular solid. The solids were filtered off using a fritted-glass filter funnel and washed with additional THF. The THF was removed on a rotary evaporator and the residue was taken up in 3.00 liters of ethyl acetate. The product solution was washed with 2×1.00 L of water, 1×1.00 L of brine, dried over $Na_2SO_4$, filtered, and concentrated in vacuo to give 836 g (97%) of fatty alcohols as yellow oil. The crude fatty alcohol mixture was then distilled (140° C./1 mmHg), and used in the following partition coefficients experiments.

Partition Coefficient Experiments

To each of the five 5-mL vials were added 1 mL of fatty alcohol mixture, and 1 mL of 3 wt % i-BuOH water solution. The biphasic mixture was vigorously stirred using Vortex Genie® for 10, 20, 30, 40, and 60 minutes, respectively. Upon mixing, the separation of layers was aided by centrifuging the mixture using Fisher Scientific Centrific 228 centrifuge (3300 rpm) for 10 minutes. 0.100 mL of both layers were taken. The organic, upper layer was diluted to 1.00 mL with toluene solution of ethylene glycol diethylether, and the water layer was diluted to 1.00 mL with methanol solution of ethylene glycol diethylether. The concentrations of i-BuOH in both phases were measured using a calibrated GC. The partition coefficient thus measured was 2.70.

The same partition coefficient measurement, as described above was run for 6 wt % i-BuOH concentration. The partition coefficient thus measured was 3.06.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing a product alcohol comprising (a) providing biomass comprising fermentable sugars, oil, and undissolved solids;

(b) liquefying the biomass to produce a feedstock slurry;

(c) separating an amount of oil from the feedstock slurry;

(d) hydrolyzing a portion of the remaining oil in the feedstock slurry of step (c) whereby the hydrolyzed oil forms an extractant;

(e) combining the feedstock slurry and extractant of step (d) with a fermentation broth; and (f) fermenting the carbon source of the feedstock slurry to produce a product alcohol whereby the product alcohol is removed from the fermentation broth by partitioning into the extractant;

wherein the partition coefficient of the extractant for the product alcohol is greater than the partition coefficient of the oil for the product alcohol.

2. The method of claim 1, wherein the portion of the remaining oil is hydrolyzed by one or more enzymes.

3. The method of claim 2, wherein the one or more enzymes is selected from esterases, lipases, phospholipases, and lysophospholipases.

4. The method of claim 2, further comprising:

inactivating the one or more catalysts after at least a portion of the oil is hydrolyzed to form the extractant.

5. The method of claim 1 , wherein the oil is separated by centrifugation, decantation, aspiration, siphoning, gravity settler, membrane-assisted phase splitting, or a combination thereof.

6. The method of claim 1, further comprising separating the undissolved solids from the feedstock slurry.

7. The method of claim 1, further comprising contacting the fermentation broth with a second extractant.

8. The method of claim 1, wherein the extractant is recycled.

9. The method of claim 1, wherein the product alcohol is selected from ethanol and butanol.

10. The method of claim 1, wherein the product alcohol is selected from 1-butanol, 2-butanol, and isobutanol.

11. The method of claim 1, wherein a portion of the separated oil in step (c) is hydrolyzed to form an extractant and is combined with the fermentation broth in step (e).

12. The method of claim 11, wherein a portion of the separated oil is hydrolyzed by one or more enzymes.

13. The method of claim 12, wherein the one or more enzymes is selected from esterases, lipases, phospholipases, and lysophospholipases.

* * * * *

SEQUENCE LISTING

```
<160> NUMBER OF SEQ ID NOS: 145

<210> SEQ ID NO 1
<211> LENGTH: 11844
<212> TYPE: DNA
<213> ORGANISM: Artificial Sequence
<220> FEATURE:
<223> OTHER INFORMATION: Plasmid

<400> SEQUENCE: 1

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactagt tagaaaaaga    180

catttttgct gtcagtcact gtcaagagat tcttttgctg gcatttcttc tagaagcaaa    240

aagagcgatg cgtcttttcc gctgaaccgt tccagcaaaa aagactacca acgcaatatg    300

gattgtcaga atcatataaa agagaagcaa ataactcctt gtcttgtatc aattgcatta    360
```

-continued

```
taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct tttatatgt ttttacttct    2580
gtatatcgtg aagtagtaag tgataagcga atttggctaa gaacgttgta agtgaacaag   2640
ggacctcttt tgcctttcaa aaaaggatta aatggagtta atcattgaga tttagttttc   2700
gttagattct gtatccctaa ataactccct tacccgacgg gaaggcacaa aagacttgaa   2760
```

```
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg cccctatctg ttcttccgct ctaccgtgag aaataaagca tcgagtacgg   3120
cagttcgctg tcactgaact aaaacaataa ggctagttcg aatgatgaac ttgcttgctg   3180
tcaaacttct gagttgccgc tgatgtgaca ctgtgacaat aaattcaaac cggttatagc   3240
ggtctcctcc ggtaccggtt ctgccacctc caatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacggaaaat cttttgataa agcaaaagaa gatggctttg aaacatttga agtaggagaa   3840
gcagtagcta aagctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
tccatctcaa atactgctga gtttggcgat tatgtgactg gtccacggat tattactgac   4440
gaagttaaaa agaatatgaa gcttgttttg gctgatattc aatctggaaa atttgctcaa   4500
gatttcgttg atgacttcaa agcggggcgt ccaaaattaa tagcctatcg cgaagctgca   4560
aaaaatcttg aaattgaaaa aattggggca gagctacgtc aagcaatgcc attcacacaa   4620
tctggtgatg acgatgcctt taaaatctat cagtaaggcc ctgcaggcct atcaagtgct   4680
ggaaactttt tctcttggaa tttttgcaac atcaagtcat agtcaattga attgacccaa   4740
tttcacattt aagatttttt ttttttcatc cgacatacat ctgtacacta ggaagccctg   4800
tttttctgaa gcagcttcaa atatatatat tttttacata tttattatga ttcaatgaac   4860
aatctaatta aatcgaaaac aagaaccgaa acgcgaataa ataatttatt tagatggtga   4920
caagtgtata agtcctcatc gggacagcta cgatttctct ttcggttttg gctgagctac   4980
tggttgctgt gacgcagcgg cattagcgcg gcgttatgag ctaccctcgt ggcctgaaag   5040
atggcgggaa taaagcggaa ctaaaaatta ctgactgagc catattgagg tcaatttgtc   5100
aactcgtcaa gtcacgtttg gtggacggcc cctttccaac gaatcgtata tactaacatg   5160
```

-continued

```
cgcgcgcttc ctatatacac atatacatat atatatatat atatatgtgt gcgtgtatgt   5220
gtacacctgt atttaatttc cttactcgcg ggtttttctt ttttctcaat tcttggcttc   5280
ctctttctcg agcggaccgg atcctccgcg gtgccggcag atctatttaa atggcgcgcc   5340
gacgtcaggt ggcacttttc ggggaaatgt gcgcggaacc cctatttgtt tatttttcta   5400
aatacattca aatatgtatc cgctcatgag acaataaccc tgataaatgc ttcaataata   5460
ttgaaaaagg aagagtatga gtattcaaca tttccgtgtc gcccttattc ccttttttgc   5520
ggcattttgc cttcctgttt ttgctcaccc agaaacgctg gtgaaagtaa aagatgctga   5580
agatcagttg ggtgcacgag tgggttacat cgaactggat ctcaacagcg gtaagatcct   5640
tgagagtttt cgccccgaag aacgttttcc aatgatgagc acttttaaag ttctgctatg   5700
tggcgcggta ttatcccgta ttgacgccgg gcaagagcaa ctcggtcgcc gcatacacta   5760
ttctcagaat gacttggttg agtactcacc agtcacagaa aagcatctta cggatggcat   5820
gacagtaaga gaattatgca gtgctgccat aaccatgagt gataacactg cggccaactt   5880
acttctgaca acgatcggag gaccgaagga gctaaccgct tttttgcaca acatggggga   5940
tcatgtaact cgccttgatc gttgggaacc ggagctgaat gaagccatac caaacgacga   6000
gcgtgacacc acgatgcctg tagcaatggc aacaacgttg cgcaaactat taactggcga   6060
actacttact ctagcttccc ggcaacaatt aatagactgg atggaggcgg ataaagttgc   6120
aggaccactt ctgcgctcgg cccttccggc tggctggttt attgctgata aatctggagc   6180
cggtgagcgt gggtctcgcg gtatcattgc agcactgggg ccagatggta agccctcccg   6240
tatcgtagtt atctacacga cggggagtca ggcaactatg gatgaacgaa atagacagat   6300
cgctgagata ggtgcctcac tgattaagca ttggtaactg tcagaccaag tttactcata   6360
tatactttag attgatttaa aacttcattt ttaatttaaa aggatctagg tgaagatcct   6420
ttttgataat ctcatgacca aaatccctta acgtgagttt tcgttccact gagcgtcaga   6480
ccccgtagaa aagatcaaag gatcttcttg agatcctttt tttctgcgcg taatctgctg   6540
cttgcaaaca aaaaaaccac cgctaccagc ggtggtttgt ttgccggatc aagagctacc   6600
aactcttttt ccgaaggtaa ctggcttcag cagagcgcag ataccaaata ctgttcttct   6660
agtgtagccg tagttaggcc accacttcaa gaactctgta gcaccgccta catacctcgc   6720
tctgctaatc ctgttaccag tggctgctgc cagtggcgat aagtcgtgtc ttaccgggtt   6780
ggactcaaga cgatagttac cggataaggc gcagcggtcg ggctgaacgg ggggttcgtg   6840
cacacagccc agcttggagc gaacgaccta caccgaactg agatacctac agcgtgagct   6900
atgagaaagc gccacgcttc ccgaagggag aaaggcggac aggtatccgg taagcggcag   6960
ggtcggaaca ggagagcgca cgagggagct tccaggggga aacgcctggt atctttatag   7020
tcctgtcggg tttcgccacc tctgacttga gcgtcgattt ttgtgatgct cgtcaggggg   7080
gcggagccta tggaaaaacg ccagcaacgc ggccttttta cggttcctgg ccttttgctg   7140
gccttttgct cacatgttct ttcctgcgtt atcccctgat tctgtggata accgtattac   7200
cgcctttgag tgagctgata ccgctcgccg cagccgaacg accgagcgca gcgagtcagt   7260
gagcgaggaa gcggaagagc gcccaatacg caaaccgcct ctccccgcgc gttggccgat   7320
tcattaatgc agctggcacg acaggtttcc cgactggaaa gcgggcagtg agcgcaacgc   7380
aattaatgtg agttagctca ctcattaggc accccaggct ttacacttta tgcttccggc   7440
tcgtatgttg tgtggaattg tgagcggata acaatttcac acaggaaaca gctatgacca   7500
tgattacgcc aagctttttc tttccaattt ttttttttc gtcattataa aaatcattac   7560
```

-continued

```
gaccgagatt cccgggtaat aactgatata attaaattga agctctaatt tgtgagttta   7620
gtatacatgc atttacttat aatacagttt tttagttttg ctggccgcat cttctcaaat   7680
atgcttccca gcctgctttt ctgtaacgtt caccctctac cttagcatcc cttccctttg   7740
caaatagtcc tcttccaaca ataataatgt cagatcctgt agagaccaca tcatccacgg   7800
ttctatactg ttgacccaat gcgtctccct tgtcatctaa acccacaccg ggtgtcataa   7860
tcaaccaatc gtaaccttca tctcttccac ccatgtctct ttgagcaata aagccgataa   7920
caaaatcttt gtcgctcttc gcaatgtcaa cagtaccctt agtatattct ccagtagata   7980
gggagccctt gcatgacaat tctgctaaca tcaaaaggcc tctaggttcc tttgttactt   8040
cttctgccgc ctgcttcaaa ccgctaacaa tacctgggcc caccacaccg tgtgcattcg   8100
taatgtctgc ccattctgct attctgtata cacccgcaga gtactgcaat ttgactgtat   8160
taccaatgtc agcaaatttt ctgtcttcga agagtaaaaa attgtacttg gcggataatg   8220
cctttagcgg cttaactgtg ccctccatgg aaaaatcagt caagatatcc acatgtgttt   8280
ttagtaaaca aattttggga cctaatgctt caactaactc cagtaattcc ttggtggtac   8340
gaacatccaa tgaagcacac aagtttgttt gcttttcgtg catgatatta aatagcttgg   8400
cagcaacagg actaggatga gtagcagcac gttccttata tgtagctttc gacatgattt   8460
atcttcgttt cctgcaggtt tttgttctgt gcagttgggt taagaatact gggcaatttc   8520
atgtttcttc aacactacat atgcgtatat ataccaatct aagtctgtgc tccttccttc   8580
gttcttcctt ctgttcggag attaccgaat caaaaaaatt tcaaggaaac cgaaatcaaa   8640
aaaaagaata aaaaaaaaat gatgaattga aaagcttgca tgcctgcagg tcgactctag   8700
tatactccgt ctactgtacg atacacttcc gctcaggtcc ttgtccttta acgaggcctt   8760
accactcttt tgttactcta ttgatccagc tcagcaaagg cagtgtgatc taagattcta   8820
tcttcgcgat gtagtaaaac tagctagacc gagaaagaga ctagaaatgc aaaaggcact   8880
tctacaatgg ctgccatcat tattatccga tgtgacgctg catttttttt tttttttttt   8940
tttttttttt tttttttttt tttttttttt ttttgtacaa atatcataaa aaaagagaat   9000
ctttttaagc aaggattttc ttaacttctt cggcgacagc atcaccgact tcggtggtac   9060
tgttggaacc acctaaatca ccagttctga tacctgcatc caaaaccttt ttaactgcat   9120
cttcaatggc tttaccttct tcaggcaagt tcaatgacaa tttcaacatc attgcagcag   9180
acaagatagt ggcgataggg ttgaccttat tctttggcaa atctggagcg gaaccatggc   9240
atggttcgta caaaccaaat gcggtgttct tgtctggcaa agaggccaag gacgcagatg   9300
gcaacaaacc caaggagcct gggataacgg aggcttcatc ggagatgata tcaccaaaca   9360
tgttgctggt gattataata ccatttaggt gggttgggtt cttaactagg atcatggcgg   9420
cagaatcaat caattgatgt tgaactttca atgtagggaa ttcgttcttg atggtttcct   9480
ccacagtttt tctccataat cttgaagagg ccaaaacatt agctttatcc aaggaccaaa   9540
taggcaatgg tggctcatgt tgtagggcca tgaaagcggc cattcttgtg attctttgca   9600
cttctggaac ggtgtattgt tcactatccc aagcgacacc atcaccatcg tcttcctttc   9660
tcttaccaaa gtaaatacct cccactaatt ctctaacaac aacgaagtca gtacctttag   9720
caaattgtgg cttgattgga gataagtcta aaagagagtc ggatgcaaag ttacatggtc   9780
ttaagttggc gtacaattga agttctttac ggatttttag taaaccttgt tcaggtctaa   9840
cactaccggt accccattta ggaccaccca cagcacctaa caaaacggca tcagccttct   9900
tggaggcttc cagcgcctca tctggaagtg gaacacctgt agcatcgata gcagcaccac   9960
```

```
caattaaatg attttcgaaa tcgaacttga cattggaacg aacatcagaa atagctttaa  10020

gaaccttaat ggcttcggct gtgatttctt gaccaacgtg gtcacctggc aaaacgacga  10080

tcttcttagg ggcagacatt acaatggtat atccttgaaa tatatataaa aaaaaaaaaa  10140

aaaaaaaaaa aaaaaaatgc agcttctcaa tgatattcga atacgctttg aggagataca  10200

gcctaatatc cgacaaactg ttttacagat ttacgatcgt acttgttacc catcattgaa  10260

ttttgaacat ccgaacctgg gagttttccc tgaaacagat agtatatttg aacctgtata  10320

ataatatata gtctagcgct ttacggaaga caatgtatgt atttcggttc ctggagaaac  10380

tattgcatct attgcatagg taatcttgca cgtcgcatcc ccggttcatt ttctgcgttt  10440

ccatcttgca cttcaatagc atatctttgt taacgaagca tctgtgcttc attttgtaga  10500

acaaaaatgc aacgcgagag cgctaatttt tcaaacaaag aatctgagct gcatttttac  10560

agaacagaaa tgcaacgcga aagcgctatt ttaccaacga agaatctgtg cttcattttt  10620

gtaaaacaaa aatgcaacgc gagagcgcta atttttcaaa caaagaatct gagctgcatt  10680

tttacagaac agaaatgcaa cgcgagagcg ctattttacc aacaaagaat ctatacttct  10740

tttttgttct acaaaaatgc atcccgagag cgctattttt ctaacaaagc atcttagatt  10800

actttttttc tcctttgtgc gctctataat gcagtctctt gataactttt tgcactgtag  10860

gtccgttaag gttagaagaa ggctactttg gtgtctattt tctcttccat aaaaaaagcc  10920

tgactccact tcccgcgttt actgattact agcgaagctg cgggtgcatt ttttcaagat  10980

aaaggcatcc ccgattatat tctataccga tgtggattgc gcatactttg tgaacagaaa  11040

gtgatagcgt tgatgattct tcattggtca gaaaattatg aacggtttct tctattttgt  11100

ctctatatac tacgtatagg aaatgtttac attttcgtat tgttttcgat tcactctatg  11160

aatagttctt actacaattt ttttgtctaa agagtaatac tagagataaa cataaaaaat  11220

gtagaggtcg agtttagatg caagttcaag gagcgaaagg tggatgggta ggttatatag  11280

ggatatagca cagagatata tagcaaagag atacttttga gcaatgtttg tggaagcggt  11340

attcgcaata ttttagtagc tcgttacagt ccggtgcgtt tttggttttt tgaaagtgcg  11400

tcttcagagc gcttttggtt ttcaaaagcg ctctgaagtt cctatacttt ctagagaata  11460

ggaacttcgg aataggaact tcaaagcgtt tccgaaaacg agcgcttccg aaaatgcaac  11520

gcgagctgcg cacatacagc tcactgttca cgtcgcacct atatctgcgt gttgcctgta  11580

tatatatata catgagaaga acggcatagt gcgtgtttat gcttaaatgc gtacttatat  11640

gcgtctattt atgtaggatg aaaggtagtc tagtacctcc tgtgatatta tcccattcca  11700

tgcggggtat cgtatgcttc cttcagcact accctttagc tgttctatat gctgccactc  11760

ctcaattgga ttagtctcat ccttcaatgc tatcatttcc tttgatattg gatcatatgc  11820

atagtaccga gaaactagag gatc                                          11844
```

<210> SEQ ID NO 2
<211> LENGTH: 15539
<212> TYPE: DNA
<213> ORGANISM: Artificial Sequence
<220> FEATURE:
<223> OTHER INFORMATION: Plasmid

<400> SEQUENCE: 2

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180
```

```
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat attttttat gcctcggtaa tgattttcat     360
ttttttttt ccacctagcg gatgactctt tttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat ttttcttgaaa gctttgcaga ggctagcaga  1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttctttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtgaaccat caccctaatc aagttttttg   1680
gggtcgaggt gccgtaaagc actaaatcgg aaccctaaag ggagcccccg atttagagct   1740
tgacggggaa agccggcgaa cgtggcgaga aaggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg ggcccccccct cgaggtcgac  2100
ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
acatacgttg catacgtcga tatagataat aatgataatg acagcaggat tatcgtaata   2580
```

```
cgtaatagct gaaaatctca aaaatgtgtg ggtcattacg taaataatga taggaatggg   2640
attcttctat ttttcctttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca aagtttctgg   4320
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gtttttttaat gagtattgaa tctgtttaga aataatggaa   4920
tattattttt atttatttat ttatattatt ggtcggctct ttcttctgaa aggtcaatga   4980
```

-continued

```
caaaatgata tgaaggaaat aatgatttct aaaattttac aacgtaagat atttttacaa   5040
aagcctagct catcttttgt catgcactat tttactcacg cttgaaatta acggccagtc   5100
cactgcggag tcatttcaaa gtcatcctaa tcgatctatc gtttttgata gctcattttg   5160
gagttcgcga ttgtcttctg ttattcacaa ctgttttaat tttatttca ttctggaact   5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aactttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc ctttttccct actcctttta   5580
gtacggaaga caatgctaat aaataagagg gtaataataa tattattaat cggcaaaaaa   5640
gattaaacgc caagcgttta attatcagaa agcaaacgtc gtaccaatcc ttgaatgctt   5700
cccaattgta tattaagagt catcacagca acatattctt gttattaaat taattattat   5760
tgatttttga tattgtataa aaaaaccaaa tatgtataaa aaaagtgaat aaaaaatacc   5820
aagtatggag aaatatatta gaagtctata cgttaaacca cccgggcccc ccctcgaggt   5880
cgacggtatc gataagcttg atatcgaatt cctgcagccc gggggatcca ctagttctag   5940
agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat tttttttata acttatttaa   6240
taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gatttagcg acagatatct cgtccaccac   6960
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
tggcgctact tctacttctt ctatgctaaa cggctttttc tcttcccaca aaactgccgc   7380
```

```
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc cccgggctg caggaattcg atatcaagct    8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct    8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaaagaa aatttattta aatgcaagat ttaaagtaaa ttcacggccc   9240
tgcaggcctc agctcttgtt ttgttctgca aataacttac ccatcttttt caaaacttta   9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
ttcgatttca gaaatataga tgaggcaccg aagaaagaag tgccttgttc agccacgatc   9780
```

-continued

```
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
ttgaaaattt taccttcatc gatattcaag gaaatcattt tattttcatt aagatggtga  10020
gtaaatgcac ccgtactaga atcggtaagc tttacaccca acataagaat aaaatcagca  10080
gattccacaa attccttcaa gtttggctct gacagagtac cgttgtaaat ccccaaaaat  10140
gagggcaatg cttcatcaac agatgattta ccaaagttca aagtagtaat aggtaactta  10200
gtctttgaaa taaactgagt aacagtcttc tctaggccga acgatataat ttcatggcct  10260
gtgattacaa ttggtttctt ggcattcttc agactttcct gtattttgtt cagaatctct  10320
tgatcagatg tattcgacgt ggaattttcc ttcttaagag gcaaggatgg tttttcagcc  10380
ttagcggcag ctacatctac aggtaaattg atgtaaaccg gctttctttc ctttagtaag  10440
gcagacaaca ctctatcaat ttcaacagtt gcattctcgg ctgtcaataa agtcctggca  10500
gcagtaaccg gttcgtgcat cttcataaag tgcttgaaat caccatcagc caacgtatgg  10560
tgaacaaact taccttcgtt ctgcactttc gaggtaggag atcccacgat ctcaacaaca  10620
ggcaggttct cagcatagga gcccgctaag ccattaactg cggataattc gccaacacca  10680
aatgtagtca agaatgccgc agccttttc gttcttgcgt acccgtcggc catataggag  10740
gcatttaact cattagcatt tcccacccat ttcatatctt tgtgtgaaat aatttgatct  10800
agaaattgca aattgtagtc acctggtact ccgaatattt cttctatacc taattcgtgt  10860
aatctgtcca acagatagtc acctactgta tacattttgt ttactagttt atgtgtgttt  10920
attcgaaact aagttcttgg tgttttaaaa ctaaaaaaaa gactaactat aaaagtagaa  10980
tttaagaagt ttaagaaata gatttacaga attacaatca atacctaccg tctttatata  11040
cttattagtc aagtagggga ataatttcag ggaactggtt tcaacctttt ttttcagctt  11100
tttccaaatc agagagagca gaaggtaata gaaggtgtaa gaaaatgaga tagatacatg  11160
cgtgggtcaa ttgccttgtg tcatcattta ctccaggcag gttgcatcac tccattgagg  11220
ttgtgcccgt tttttgcctg tttgtgcccc tgttctctgt agttgcgcta agagaatgga  11280
cctatgaact gatggttggt gaagaaaaca atattttggt gctgggattc ttttttttc  11340
tggatgccag cttaaaaagc gggctccatt atatttagtg gatgccagga ataaactgtt  11400
cacccagaca cctacgatgt tatatattct gtgtaacccg cccccctattt tgggcatgta  11460
cgggttacag cagaattaaa aggctaattt tttgactaaa taaagttagg aaaatcacta  11520
ctattaatta tttacgtatt ctttgaaatg gcagtattga taatgataaa ctcgaactga  11580
aaaagcgtgt tttttattca aaatgattct aactccctta cgtaatcaag gaatcttttt  11640
gccttggcct ccgcgtcatt aaacttcttg ttgttgacgc taacattcaa cgctagtata  11700
tattcgtttt tttcaggtaa gttcttttca acgggtctta ctgatgaggc agtcgcgtct  11760
gaacctgtta agaggtcaaa tatgtcttct tgaccgtacg tgtcttgcat gttattagct  11820
ttgggaattt gcatcaagtc ataggaaaat ttaaatcttg gctctcttgg gctcaaggtg  11880
acaaggtcct cgaaaatagg gcgcgcccca ccgcggtgga gctccagctt ttgttccctt  11940
tagtgagggt taattgcgcg cttggcgtaa tcatggtcat agctgtttcc tgtgtgaaat  12000
tgttatccgc tcacaattcc acacaacata cgagccggaa gcataaagtg taaagcctgg  12060
ggtgcctaat gagtgagcta actcacatta attgcgttgc gctcactgcc cgctttccag  12120
tcgggaaacc tgtcgtgcca gctgcattaa tgaatcggcc aacgcgcggg gagaggcggt  12180
```

```
ttgcgtattg ggcgctcttc cgcttcctcg ctcactgact cgctgcgctc ggtcgttcgg  12240

ctgcggcgag cggtatcagc tcactcaaag gcggtaatac ggttatccac agaatcaggg  12300

gataacgcag gaaagaacat gtgagcaaaa ggccagcaaa aggccaggaa ccgtaaaaag  12360

gccgcgttgc tggcgttttt ccataggctc cgcccccctg acgagcatca caaaaatcga  12420

cgctcaagtc agaggtggcg aaacccgaca ggactataaa gataccaggc gtttccccct  12480

ggaagctccc tcgtgcgctc tcctgttccg accctgccgc ttaccggata cctgtccgcc  12540

tttctccctt cgggaagcgt ggcgctttct catagctcac gctgtaggta tctcagttcg  12600

gtgtaggtcg ttcgctccaa gctgggctgt gtgcacgaac cccccgttca gcccgaccgc  12660

tgcgccttat ccggtaacta tcgtcttgag tccaacccgg taagacacga cttatcgcca  12720

ctggcagcag ccactggtaa caggattagc agagcgaggt atgtaggcgg tgctacagag  12780

ttcttgaagt ggtggcctaa ctacggctac actagaagaa cagtatttgg tatctgcgct  12840

ctgctgaagc cagttacctt cggaaaaaga gttggtagct cttgatccgg caaacaaacc  12900

accgctggta gcggtggttt ttttgtttgc aagcagcaga ttacgcgcag aaaaaaagga  12960

tctcaagaag atcctttgat cttttctacg gggtctgacg ctcagtggaa cgaaaactca  13020

cgttaaggga ttttggtcat gagattatca aaaaggatct tcacctagat ccttttaaat  13080

taaaaatgaa gttttaaatc aatctaaagt atatatgagt aaacttggtc tgacagttac  13140

caatgcttaa tcagtgaggc acctatctca gcgatctgtc tatttcgttc atccatagtt  13200

gcctgactcc ccgtcgtgta gataactacg atacgggagg gcttaccatc tggccccagt  13260

gctgcaatga taccgcgaga cccacgctca ccggctccag atttatcagc aataaaccag  13320

ccagccggaa gggccgagcg cagaagtggt cctgcaactt tatccgcctc catccagtct  13380

attaattgtt gccgggaagc tagagtaagt agttcgccag ttaatagttt gcgcaacgtt  13440

gttgccattg ctacaggcat cgtggtgtca cgctcgtcgt ttggtatggc ttcattcagc  13500

tccggttccc aacgatcaag gcgagttaca tgatccccca tgttgtgcaa aaaagcggtt  13560

agctccttcg gtcctccgat cgttgtcaga agtaagttgg ccgcagtgtt atcactcatg  13620

gttatggcag cactgcataa ttctcttact gtcatgccat ccgtaagatg cttttctgtg  13680

actggtgagt actcaaccaa gtcattctga gaatagtgta tgcggcgacc gagttgctct  13740

tgcccggcgt caatacggga taataccgcg ccacatagca gaactttaaa agtgctcatc  13800

attggaaaac gttcttcggg gcgaaaactc tcaaggatct taccgctgtt gagatccagt  13860

tcgatgtaac ccactcgtgc acccaactga tcttcagcat cttttacttt caccagcgtt  13920

tctgggtgag caaaaacagg aaggcaaaat gccgcaaaaa agggaataag ggcgacacgg  13980

aaatgttgaa tactcatact cttccttttt caatattatt gaagcattta tcagggttat  14040

tgtctcatga gcggatacat atttgaatgt atttagaaaa ataaacaaat aggggttccg  14100

cgcacatttc cccgaaaagt gccacctgaa cgaagcatct gtgcttcatt ttgtagaaca  14160

aaaatgcaac gcgagagcgc taatttttca aacaaagaat ctgagctgca tttttacaga  14220

acagaaatgc aacgcgaaag cgctatttta ccaacgaaga atctgtgctt catttttgta  14280

aaacaaaaat gcaacgcgag agcgctaatt tttcaaacaa agaatctgag ctgcattttt  14340

acagaacaga aatgcaacgc gagagcgcta ttttaccaac aaagaatcta tacttctttt  14400

ttgttctaca aaaatgcatc ccgagagcgc tatttttcta acaaagcatc ttagattact  14460

tttttctcc tttgtgcgct ctataatgca gtctcttgat aactttttgc actgtaggtc  14520

cgttaaggtt agaagaaggc tactttggtg tctattttct cttccataaa aaaagcctga  14580
```

```
ctccacttcc cgcgtttact gattactagc gaagctgcgg gtgcattttt tcaagataaa  14640

ggcatccccg attatattct ataccgatgt ggattgcgca tactttgtga acagaaagtg  14700

atagcgttga tgattcttca ttggtcagaa aattatgaac ggtttcttct attttgtctc  14760

tatatactac gtataggaaa tgtttacatt ttcgtattgt tttcgattca ctctatgaat  14820

agttcttact acaatttttt tgtctaaaga gtaatactag agataaacat aaaaaatgta  14880

gaggtcgagt ttagatgcaa gttcaaggag cgaaaggtgg atgggtaggt tatataggga  14940

tatagcacag agatatatag caaagagata cttttgagca atgtttgtgg aagcggtatt  15000

cgcaatattt tagtagctcg ttacagtccg gtgcgttttt ggttttttga aagtgcgtct  15060

tcagagcgct tttggttttc aaaagcgctc tgaagttcct atactttcta gagaatagga  15120

acttcggaat aggaacttca aagcgtttcc gaaaacgagc gcttccgaaa atgcaacgcg  15180

agctgcgcac atacagctca ctgttcacgt cgcacctata tctgcgtgtt gcctgtatat  15240

atatatacat gagaagaacg gcatagtgcg tgtttatgct taaatgcgta cttatatgcg  15300

tctatttatg taggatgaaa ggtagtctag tacctcctgt gatattatcc cattccatgc  15360

ggggtatcgt atgcttcctt cagcactacc ctttagctgt tctatatgct gccactcctc  15420

aattggatta gtctcatcct tcaatgctat catttccttt gatattggat catactaaga  15480

aaccattatt atcatgacat taacctataa aaataggcgt atcacgaggc cctttcgtc   15539
```

<210> SEQ ID NO 3
<211> LENGTH: 4586
<212> TYPE: DNA
<213> ORGANISM: Artificial Sequence
<220> FEATURE:
<223> OTHER INFORMATION: pLA54 plasmid

<400> SEQUENCE: 3

```
gggtaccgag ctcgaattca ctggccgtcg ttttacaacg tcgtgactgg gaaaaccctg     60

gcgttaccca acttaatcgc cttgcagcac atcccccttt cgccagctgg cgtaatagcg    120

aagaggcccg caccgatcgc ccttcccaac agttgcgcag cctgaatggc gaatggcgcc    180

tgatgcggta ttttctcctt acgcatctgt gcggtatttc acaccgcata tggtgcactc    240

tcagtacaat ctgctctgat gccgcatagt taagccagcc ccgacacccg ccaacacccg    300

ctgacgcgcc ctgacgggct tgtctgctcc cggcatccgc ttacagacaa gctgtgaccg    360

tctccgggag ctgcatgtgt cagaggtttt caccgtcatc accgaaacgc gcgagacgaa    420

agggcctcgt gatacgccta tttttatagg ttaatgtcat gataataatg gtttcttaga    480

cgtcaggtgg cacttttcgg ggaaatgtgc gcggaacccc tatttgttta tttttctaaa    540

tacattcaaa tatgtatccg ctcatgagac aataaccctg ataaatgctt caataatatt    600

gaaaaaggaa gagtatgagt attcaacatt tccgtgtcgc ccttattccc ttttttgcgg    660

cattttgcct tcctgttttt gctcacccag aaacgctggt gaaagtaaaa gatgctgaag    720

atcagttggg tgcacgagtg ggttacatcg aactggatct caacagcggt aagatccttg    780

agagttttcg ccccgaagaa cgttttccaa tgatgagcac ttttaaagtt ctgctatgtg    840

gcgcggtatt atcccgtatt gacgccgggc aagagcaact cggtcgccgc atacactatt    900

ctcagaatga cttggttgag tactcaccag tcacagaaaa gcatcttacg gatggcatga    960

cagtaagaga attatgcagt gctgccataa ccatgagtga taacactgcg gccaacttac   1020

ttctgacaac gatcggagga ccgaaggagc taaccgcttt tttgcacaac atgggggatc   1080

atgtaactcg ccttgatcgt tgggaaccgg agctgaatga agccatacca aacgacgagc   1140
```

-continued

```
gtgacaccac gatgcctgta gcaatggcaa caacgttgcg caaactatta actggcgaac   1200
tacttactct agcttcccgg caacaattaa tagactggat ggaggcggat aaagttgcag   1260
gaccacttct gcgctcggcc cttccggctg gctggtttat tgctgataaa tctggagccg   1320
gtgagcgtgg gtctcgcggt atcattgcag cactggggcc agatggtaag ccctcccgta   1380
tcgtagttat ctacacgacg gggagtcagg caactatgga tgaacgaaat agacagatcg   1440
ctgagatagg tgcctcactg attaagcatt ggtaactgtc agaccaagtt tactcatata   1500
tactttagat tgatttaaaa cttcattttt aatttaaaag gatctaggtg aagatccttt   1560
ttgataatct catgaccaaa atcccttaac gtgagttttc gttccactga gcgtcagacc   1620
ccgtagaaaa gatcaaagga tcttcttgag atcctttttt tctgcgcgta atctgctgct   1680
tgcaaacaaa aaaaccaccg ctaccagcgg tggtttgttt gccggatcaa gagctaccaa   1740
ctctttttcc gaaggtaact ggcttcagca gagcgcagat accaaatact gtccttctag   1800
tgtagccgta gttaggccac cacttcaaga actctgtagc accgcctaca tacctcgctc   1860
tgctaatcct gttaccagtg gctgctgcca gtggcgataa gtcgtgtctt accgggttgg   1920
actcaagacg atagttaccg gataaggcgc agcggtcggg ctgaacgggg ggttcgtgca   1980
cacagcccag cttggagcga acgacctaca ccgaactgag atacctacag cgtgagctat   2040
gagaaagcgc cacgcttccc gaagggagaa aggcggacag gtatccggta agcggcaggg   2100
tcggaacagg agagcgcacg agggagcttc caggggggaaa cgcctggtat ctttatagtc   2160
ctgtcgggtt tcgccacctc tgacttgagc gtcgattttt gtgatgctcg tcaggggggc   2220
ggagcctatg gaaaaacgcc agcaacgcgg cctttttacg gttcctggcc ttttgctggc   2280
cttttgctca catgttcttt cctgcgttat cccctgattc tgtggataac cgtattaccg   2340
cctttgagtg agctgatacc gctcgccgca gccgaacgac cgagcgcagc gagtcagtga   2400
gcgaggaagc ggaagagcgc ccaatacgca aaccgcctct ccccgcgcgt tggccgattc   2460
attaatgcag ctggcacgac aggtttcccg actggaaagc gggcagtgag cgcaacgcaa   2520
ttaatgtgag ttagctcact cattaggcac cccaggcttt acactttatg cttccggctc   2580
gtatgttgtg tggaattgtg agcggataac aatttcacac aggaaacagc tatgaccatg   2640
attacgccaa gcttgcatgc ctgcaggtcg actctagagg atccccgcat tgcggattac   2700
gtattctaat gttcagataa cttcgtatag catacattat acgaagttat ctagggattc   2760
ataaccattt tctcaatcga attacacaga acacaccgta caaacctctc tatcataact   2820
acttaatagt cacacacgta ctcgtctaaa tacacatcat cgtcctacaa gttcatcaaa   2880
gtgttggaca gacaactata ccagcatgga tctcttgtat cggttctttt ctcccgctct   2940
ctcgcaataa caatgaacac tgggtcaatc atagcctaca caggtgaaca gagtagcgtt   3000
tatacagggt ttatacggtg attcctacgg caaaaatttt tcatttctaa aaaaaaaaag   3060
aaaaattttt ctttccaacg ctagaaggaa aagaaaaatc taattaaatt gatttggtga   3120
ttttctgaga gttccctttt tcatatatcg aattttgaat ataaaaggag atcgaaaaaa   3180
tttttctatt caatctgttt tctggtttta tttgatagtt tttttgtgta ttattattat   3240
ggattagtac tggtttatat gggtttttct gtataacttc tttttatttt agtttgttta   3300
atcttatttt gagttacatt atagttccct aactgcaaga gaagtaacat taaaactcga   3360
gatgggtaag gaaaagactc acgtttcgag gccgcgatta aattccaaca tggatgctga   3420
tttatatggg tataaatggg ctcgcgataa tgtcgggcaa tcaggtgcga caatctatcg   3480
attgtatggg aagcccgatg cgccagagtt gtttctgaaa catggcaaag gtagcgttgc   3540
```

```
caatgatgtt acagatgaga tggtcagact aaactggctg acggaattta tgcctcttcc   3600
gaccatcaag cattttatcc gtactcctga tgatgcatgg ttactcacca ctgcgatccc   3660
cggcaaaaca gcattccagg tattagaaga atatcctgat tcaggtgaaa atattgttga   3720
tgcgctggca gtgttcctgc gccggttgca ttcgattcct gtttgtaatt gtccttttaa   3780
cagcgatcgc gtatttcgtc tcgctcaggc gcaatcacga atgaataacg gtttggttga   3840
tgcgagtgat tttgatgacg agcgtaatgg ctggcctgtt gaacaagtct ggaaagaaat   3900
gcataagctt ttgccattct caccggattc agtcgtcact catggtgatt tctcacttga   3960
taaccttatt tttgacgagg ggaaattaat aggttgtatt gatgttggac gagtcggaat   4020
cgcagaccga taccaggatc ttgccatcct atggaactgc ctcggtgagt tttctccttc   4080
attacagaaa cggctttttc aaaaatatgg tattgataat cctgatatga ataaattgca   4140
gtttcatttg atgctcgatg agtttttcta agtttaactt gatactacta gatttttct    4200
cttcatttat aaaatttttg gttataattg aagctttaga agtatgaaaa aatccttttt   4260
tttcattctt tgcaaccaaa ataagaagct tcttttattc attgaaatga tgaatataaa   4320
cctaacaaaa gaaaaagact cgaatatcaa acattaaaaa aaaataaaag aggttatctg   4380
ttttcccatt tagttggagt ttgcattttc taatagatag aactctcaat taatgtggat   4440
ttagtttctc tgttcgtttt tttttgtttt gttctcactg tatttacatt tctatttagt   4500
atttagttat tcatataatc tataacttcg tatagcatac attatacgaa gttatccagt   4560
gatgatacaa cgagttagcc aaggtg                                        4586
```

<210> SEQ ID NO 4
<211> LENGTH: 80
<212> TYPE: DNA
<213> ORGANISM: Artificial Sequence
<220> FEATURE:
<223> OTHER INFORMATION: Primer

<400> SEQUENCE: 4

```
ttccggtttc tttgaaattt ttttgattcg gtaatctccg agcagaagga gcattgcgga     60
ttacgtattc taatgttcag                                                 80
```

<210> SEQ ID NO 5
<211> LENGTH: 81
<212> TYPE: DNA
<213> ORGANISM: Artificial Sequence
<220> FEATURE:
<223> OTHER INFORMATION: Primer

<400> SEQUENCE: 5

```
gggtaataac tgatataatt aaattgaagc tctaatttgt gagtttagta caccttggct     60
aactcgttgt atcatcactg g                                               81
```

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6

```
gcctcgagtt ttaatgttac ttctcttgca gttaggga                             38
```

<210> SEQ ID NO 7
<211> LENGTH: 31
<212> TYPE: DNA

<213> ORGANISM: Artificial Sequence
<220> FEATURE:
<223> OTHER INFORMATION: Primer

<400> SEQUENCE: 7
gctaaattcg agtgaaacac aggaagacca g 31

<210> SEQ ID NO 8
<211> LENGTH: 90
<212> TYPE: DNA
<213> ORGANISM: Artificial Sequence
<220> FEATURE:
<223> OTHER INFORMATION: Primer

<400> SEQUENCE: 8
gtattttggt agattcaatt ctctttccct ttccttttcc ttcgctcccc ttccttatca 60
gcattgcgga ttacgtattc taatgttcag 90

<210> SEQ ID NO 9
<211> LENGTH: 90
<212> TYPE: DNA
<213> ORGANISM: Artificial Sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc 60
accttggcta actcgttgta tcatcactgg 90

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggtgcggg cctcttcgct a 21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aatgtgagtt agctcactca t 21

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
aattggatcc ggcgcgccgt ttaaacggcc ggccaatgtg gctgtggttt cagggtc 57

<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatttctaga ttaattaagc ggccgcaagg ccatgaagct ttttctttc 49

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ttctcgacgt gggccttttt cttg 24

<210> SEQ ID NO 15
<211> LENGTH: 49
<212> TYPE: DNA
<213> ORGANISM: Artificial Sequence
<220> FEATURE:
<223> OTHER INFORMATION: Primer

<400> SEQUENCE: 15
tgcagcttta aataatcggt gtcactactt tgccttcgtt tatcttgcc 49

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
gagcaggcaa gataaacgaa ggcaaagtag tgacaccgat tatttaaag 49

<210> SEQ ID NO 17
<211> LENGTH: 49
<212> TYPE: DNA
<213> ORGANISM: Artificial Sequence
<220> FEATURE:
<223> OTHER INFORMATION: Primer

<400> SEQUENCE: 17
tatggaccct gaaaccacag ccacattgta accaccacga cggttgttg 49

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
tttagcaaca accgtcgtgg tggttacaat gtggctgtgg tttcagggt 49

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
ccagaaaccc tatacctgtg tggacgtaag gccatgaagc tttttcttt 49

<210> SEQ ID NO 20
<211> LENGTH: 49
<212> TYPE: DNA

<213> ORGANISM: Artificial Sequence
<220> FEATURE:
<223> OTHER INFORMATION: Primer

<400> SEQUENCE: 20
attggaaaga aaaagcttca tggccttacg tccacacagg tatagggtt 49

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cataagaaca cctttggtgg ag 22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
aggattatca ttcataagtt tc 22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ttcttggagc tgggacatgt ttg 23

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tgatgatatt tcataaataa tg 22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
atgcgtccat ctttacagtc ctg 23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tacgtacgga ccaatcgaag tg 22

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27
aattcgtttg agtacactac taatggcttt gttggcaata tgtttttgc 49

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
atatagcaaa aacatattgc caacaaagcc attagtagtg tactcaaac 49

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
tatggaccct gaaaccacag ccacattctt gttatttata aaaagacac 49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
ctcccgtgtc tttttataaa taacaagaat gtggctgtgg tttcagggt 49

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
taccgtaggc gtccttagga aagatagaag gccatgaagc tttttcttt 49

<210> SEQ ID NO 32
<211> LENGTH: 49
<212> TYPE: DNA
<213> ORGANISM: Artificial Sequence
<220> FEATURE:
<223> OTHER INFORMATION: Primer

<400> SEQUENCE: 32
attggaaaga aaaagcttca tggccttcta tctttcctaa ggacgccta 49

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ttattgtttg gcatttgtag c 21

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ccaagcatct cataaaccta tg 22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tgtgcagatg cagatgtgag ac 22

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36
agttattgat accgtac 17

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
cgagataccg taggcgtcc 19

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttatgtatgc tcttctgact tttc 24

<210> SEQ ID NO 39
<211> LENGTH: 49
<212> TYPE: DNA
<213> ORGANISM: Artificial Sequence
<220> FEATURE:
<223> OTHER INFORMATION: Primer

<400> SEQUENCE: 39
aataattaga gattaaatcg ctcatttttt gccagtttct tcaggcttc 49

<210> SEQ ID NO 40
<211> LENGTH: 49
<212> TYPE: DNA

<213> ORGANISM: Artificial Sequence
<220> FEATURE:
<223> OTHER INFORMATION: Primer

<400> SEQUENCE: 40
agcctgaaga aactggcaaa aaatgagcga tttaatctct aattattag 49

<210> SEQ ID NO 41
<211> LENGTH: 49
<212> TYPE: DNA
<213> ORGANISM: Artificial Sequence
<220> FEATURE:
<223> OTHER INFORMATION: Primer

<400> SEQUENCE: 41
tatggaccct gaaaccacag ccacattttt caatcattgg agcaatcat 49

<210> SEQ ID NO 42
<211> LENGTH: 49
<212> TYPE: DNA
<213> ORGANISM: Artificial Sequence
<220> FEATURE:
<223> OTHER INFORMATION: Primer

<400> SEQUENCE: 42
taaaatgatt gctccaatga ttgaaaaatg tggctgtggt ttcagggtc 49

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
accgtaggtg ttgtttggga aagtggaagg ccatgaagct ttttctttc 49

<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
ttggaaagaa aaagcttcat ggccttccac tttcccaaac aacacctac 49

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttattgctta gcgttggtag cag 23

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tttttggtgg ttccggcttc c 21

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
aaagttggca tagcggaaac tt 22

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gtcattgaca ccatct 16

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
agagataccg taggtgttg 19

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
aattggcgcg ccatgaaagc tctggtttat cac 33

<210> SEQ ID NO 51
<211> LENGTH: 49
<212> TYPE: DNA
<213> ORGANISM: Artificial Sequence
<220> FEATURE:
<223> OTHER INFORMATION: Primer

<400> SEQUENCE: 51
tgaatcatga gttttatgtt aattagctca ggcagcgcct gcgttcgag 49

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
atcctctcga acgcaggcgc tgcctgagct aattaacata aaactcatg 49

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
aattgtttaa acaagtaaat aaattaatca gcat 34

<210> SEQ ID NO 54
<211> LENGTH: 49
<212> TYPE: DNA
<213> ORGANISM: Artificial Sequence
<220> FEATURE:
<223> OTHER INFORMATION: Primer

<400> SEQUENCE: 54
acacaataca ataacaagaa gaacaaaatg aaagctctgg tttatcacg 49

<210> SEQ ID NO 55
<211> LENGTH: 49
<212> TYPE: DNA
<213> ORGANISM: Artificial Sequence
<220> FEATURE:
<223> OTHER INFORMATION: Primer

<400> SEQUENCE: 55
agcgtataca tctgttggga aagtagaagg ccatgaagct tttctttc 49

<210> SEQ ID NO 56
<211> LENGTH: 49
<212> TYPE: DNA
<213> ORGANISM: Artificial Sequence
<220> FEATURE:
<223> OTHER INFORMATION: Primer

<400> SEQUENCE: 56
ttggaaagaa aaagcttcat ggccttctac tttcccaaca gatgtatac 49

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
ttattgttta gcgttagtag cg 22

<210> SEQ ID NO 58
<211> LENGTH: 72
<212> TYPE: DNA
<213> ORGANISM: Artificial Sequence
<220> FEATURE:
<223> OTHER INFORMATION: Primer

<400> SEQUENCE: 58
cataatcaat ctcaaagaga acaacacaat acaataacaa gaagaacaaa atgaaagctc 60
tggtttatca cg 72

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
taggcataat caccgaagaa g 21

<210> SEQ ID NO 60

<211> LENGTH: 21
<212> TYPE: DNA
<213> ORGANISM: Artificial Sequence
<220> FEATURE:
<223> OTHER INFORMATION: Primer

<400> SEQUENCE: 60
aaaatggtaa gcagctgaaa g 21

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
agttgttaga actgttg 17

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gacgatagcg tatacatct 19

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cttagcctct agccatagcc at 22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ttagttttgc tggccgcatc ttc 23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cccattaata tactattgag a 21

<210> SEQ ID NO 66
<211> LENGTH: 7523
<212> TYPE: DNA
<213> ORGANISM: Artificial Sequence
<220> FEATURE:
<223> OTHER INFORMATION: Plasmid

<400> SEQUENCE: 66

-continued

```
ccagcttttg ttccctttag tgagggttaa ttgcgcgctt ggcgtaatca tggtcatagc      60
tgtttcctgt gtgaaattgt tatccgctca caattccaca caacatagga gccggaagca     120
taaagtgtaa agcctggggt gcctaatgag tgaggtaact cacattaatt gcgttgcgct     180
cactgcccgc tttccagtcg ggaaacctgt cgtgccagct gcattaatga atcggccaac     240
gcgcggggag aggcggtttg cgtattgggc gctcttccgc ttcctcgctc actgactcgc     300
tgcgctcggt cgttcggctg cggcgagcgg tatcagctca ctcaaaggcg gtaatacggt     360
tatccacaga atcaggggat aacgcaggaa agaacatgtg agcaaaaggc cagcaaaagg     420
ccaggaaccg taaaaaggcc gcgttgctgg cgtttttcca taggctccgc ccccctgacg     480
agcatcacaa aaatcgacgc tcaagtcaga ggtggcgaaa cccgacagga ctataaagat     540
accaggcgtt tccccctgga agctccctcg tgcgctctcc tgttccgacc ctgccgctta     600
ccggatacct gtccgccttt ctcccttcgg gaagcgtggc gctttctcat agctcacgct     660
gtaggtatct cagttcggtg taggtcgttc gctccaagct gggctgtgtg cacgaacccc     720
ccgttcagcc cgaccgctgc gccttatccg gtaactatcg tcttgagtcc aacccggtaa     780
gacacgactt atcgccactg gcagcagcca ctggtaacag gattagcaga gcgaggtatg     840
taggcggtgc tacagagttc ttgaagtggt ggcctaacta cggctacact agaaggacag     900
tatttggtat ctgcgctctg ctgaagccag ttaccttcgg aaaaagagtt ggtagctctt     960
gatccggcaa acaaaccacc gctggtagcg gtggtttttt tgtttgcaag cagcagatta    1020
cgcgcagaaa aaaaggatct caagaagatc ctttgatctt ttctacgggg tctgacgctc    1080
agtggaacga aaactcacgt taagggattt tggtcatgag attatcaaaa aggatcttca    1140
cctagatcct tttaaattaa aaatgaagtt ttaaatcaat ctaaagtata tatgagtaaa    1200
cttggtctga cagttaccaa tgcttaatca gtgaggcacc tatctcagcg atctgtctat    1260
ttcgttcatc catagttgcc tgactccccg tcgtgtagat aactacgata cgggagggct    1320
taccatctgg ccccagtgct gcaatgatac cgcgagaccc acgctcaccg gctccagatt    1380
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa tttttcaaac aaagaatctg    2280
agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
```

-continued

```
atctgagctg catttttaca gaacagaaat gcaacgcgag agcgctattt taccaacaaa   2460
gaatctatac ttcttttttg ttctacaaaa atgcatcccg agagcgctat tttctaaca    2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttca agataaaggc atccccgatt atattctata ccgatgtgga ttgcgcatac    2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca atttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
```

-continued

```
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttctttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
ccccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggccccaca aaccttcaaa ttaacgaatc aaattaacaa ccataggatg   5940
ataatgcgat tagtttttta gccttatttc tggggtaatt aatcagcgaa gcgatgattt   6000
ttgatctatt aacagatata taaatggaaa agctgcataa ccactttaac taatactttc   6060
aacattttca gtttgtatta cttcttattc aaatgtcata aaagtatcaa caaaaaattg   6120
ttaatatacc tctatacttt aacgtcaagg agaaaaaatgt ccaatttact gcccgtacac   6180
caaaatttgc ctgcattacc ggtcgatgca acgagtgatg aggttcgcaa gaacctgatg   6240
gacatgttca gggatcgcca ggcgttttct gagcatacct ggaaaatgct tctgtccgtt   6300
tgccggtcgt gggcggcatg gtgcaagttg aataaccgga aatggtttcc cgcagaacct   6360
gaagatgttc gcgattatct tctatatctt caggcgcgcg gtctggcagt aaaaactatc   6420
cagcaacatt tgggccagct aaacatgctt catcgtcggt ccgggctgcc acgaccaagt   6480
gacagcaatg ctgtttcact ggttatgcgg cggatccgaa aagaaaacgt tgatgccggt   6540
gaacgtgcaa aacaggctct agcgttcgaa cgcactgatt tcgaccaggt tcgttcactc   6600
atggaaaata gcgatcgctg ccaggatata cgtaatctgg catttctggg gattgcttat   6660
aacaccctgt tacgtatagc cgaaattgcc aggatcaggg ttaaagatat ctcacgtact   6720
gacggtggga gaatgttaat ccatattggc agaacgaaaa cgctggttag caccgcaggt   6780
gtagagaagg cacttagcct gggggtaact aaactggtcg agcgatggat ttccgtctct   6840
ggtgtagctg atgatccgaa taactacctg ttttgccggg tcagaaaaaa tggtgttgcc   6900
gcgccatctg ccaccagcca gctatcaact cgcgccctgg aagggatttt tgaagcaact   6960
catcgattga tttacggcgc taaggatgac tctggtcaga gatacctggc ctggtctgga   7020
cacagtgccc gtgtcggagc cgcgcgagat atggcccgcg ctggagtttc aataccggag   7080
atcatgcaag ctggtggctg gaccaatgta aatattgtca tgaactatat ccgtaacctg   7140
gatagtgaaa caggggcaat ggtgcgcctg ctggaagatg gcgattagga gtaagcgaat   7200
```

ttcttatgat ttatgatttt tattattaaa taagttataa aaaaaataag tgtatacaaa 7260
ttttaaagtg actcttaggt tttaaaacga aaattcttat tcttgagtaa ctctttcctg 7320
taggtcaggt tgctttctca ggtatagcat gaggtcgctc ttattgacca cacctctacc 7380
ggcatgccga gcaaatgcct gcaaatcgct ccccatttca cccaattgta gatatgctaa 7440
ctccagcaat gagttgatga atctcggtgt gtattttatg tcctcagagg acaacacctg 7500
tggtccgcca ccgcggtgga gct 7523

<210> SEQ ID NO 67
<211> LENGTH: 15456
<212> TYPE: DNA
<213> ORGANISM: Artificial Sequence
<220> FEATURE:
<223> OTHER INFORMATION: Template

<400> SEQUENCE: 67
aaagagtaat actagagata aacataaaaa atgtagaggt cgagtttaga tgcaagttca 60
aggagcgaaa ggtggatggg taggttatat agggatatag cacagagata tatagcaaag 120
agatactttt gagcaatgtt tgtggaagcg gtattcgcaa tattttagta gctcgttaca 180
gtccggtgcg tttttggttt tttgaaagtg cgtcttcaga gcgcttttgg ttttcaaaag 240
cgctctgaag ttcctatact ttctagagaa taggaacttc ggaataggaa cttcaaagcg 300
tttccgaaaa cgagcgcttc cgaaaatgca acgcgagctg cgcacataca gctcactgtt 360
cacgtcgcac ctatatctgc gtgttgcctg tatatatata tacatgagaa gaacggcata 420
gtgcgtgttt atgcttaaat gcgtacttat atgcgtctat ttatgtagga tgaaaggtag 480
tctagtacct cctgtgatat tatcccattc catgcggggt atcgtatgct tccttcagca 540
ctacccttta gctgttctat atgctgccac tcctcaattg gattagtctc atccttcaat 600
gctatcattt cctttgatat tggatcatac taagaaacca ttattatcat gacattaacc 660
tataaaaata ggcgtatcac gaggcccttt cgtctcgcgc gtttcggtga tgacggtgaa 720
aacctctgac acatgcagct cccggagacg gtcacagctt gtctgtaagc ggatgccggg 780
agcagacaag cccgtcaggg cgcgtcagcg ggtgttggcg ggtgtcgggg ctggcttaac 840
tatgcggcat cagagcagat tgtactgaga gtgcaccata aattcccgtt ttaagagctt 900
ggtgagcgct aggagtcact gccaggtatc gtttgaacac ggcattagtc agggaagtca 960
taacacagtc ctttcccgca attttctttt tctattactc ttggcctcct ctagtacact 1020
ctatattttt ttatgcctcg gtaatgattt tcattttttt ttttccacct agcggatgac 1080 tcttttttttt tcttagcgat tggcattatc acataatgaa ttatacatta tataaagtaa 1140
tgtgatttct tcgaagaata tactaaaaaa tgagcaggca agataaacga aggcaaagat 1200
gacagagcag aaagccctag taaagcgtat tacaaatgaa accaagattc agattgcgat 1260
ctctttaaag ggtggtcccc tagcgataga gcactcgatc ttcccagaaa aagaggcaga 1320
agcagtagca gaacaggcca cacaatcgca agtgattaac gtccacacag gtatagggtt 1380
tctggaccat atgatacatg ctctggccaa gcattccggc tggtcgctaa tcgttgagtg 1440
cattggtgac ttacacatag acgaccatca caccactgaa gactgcggga ttgctctcgg 1500
tcaagctttt aaagaggccc taggggccgt gcgtggagta aaaaggtttg gatcaggatt 1560
tgcgcctttg gatgaggcac tttccagagc ggtggtagat ctttcgaaca ggccgtacgc 1620
agttgtcgaa cttggtttgc aaagggagaa agtaggagat ctctcttgcg agatgatccc 1680
gcattttctt gaaagctttg cagaggctag cagaattacc ctccacgttg attgtctgcg 1740

-continued

```
aggcaagaat gatcatcacc gtagtgagag tgcgttcaag gctcttgcgg ttgccataag   1800

agaagccacc tcgcccaatg gtaccaacga tgttccctcc accaaaggtg ttcttatgta   1860

gtgacaccga ttatttaaag ctgcagcata cgatatatat acatgtgtat atatgtatac   1920

ctatgaatgt cagtaagtat gtatacgaac agtatgatac tgaagatgac aaggtaatgc   1980

atcattctat acgtgtcatt ctgaacgagg cgcgctttcc tttttttcttt ttgctttttc   2040

ttttttttc tcttgaactc gacggatcta tgcggtgtga aataccgcac agatgcgtaa   2100

ggagaaaata ccgcatcagg aaattgtaag cgttaatatt ttgttaaaat tcgcgttaaa   2160

tttttgttaa atcagctcat ttttaacca ataggccgaa atcggcaaaa tcccttataa   2220

atcaaaagaa tagaccgaga tagggttgag tgttgttcca gtttggaaca agagtccact   2280

attaaagaac gtggactcca acgtcaaagg gcgaaaaacc gtctatcagg gcgatggccc   2340

actacgtgaa ccatcaccct aatcaagttt tttggggtcg aggtgccgta aagcactaaa   2400

tcggaaccct aaagggagcc cccgatttag agcttgacgg ggaaagccgg cgaacgtggc   2460

gagaaaggaa gggaagaaag cgaaaggagc gggcgctagg gcgctggcaa gtgtagcggt   2520

cacgctgcgc gtaaccacca cacccgccgc gcttaatgcg ccgctacagg gcgcgtccat   2580

tcgccattca ggctgcgcaa ctgttgggaa gggcgcggtg cgggcctctt cgctattacg   2640

ccagctggcg aaagggggat gtgctgcaag gcgattaagt tgggtaacgc cagggttttc   2700

ccagtcacga cgttgtaaaa cgacggccag tgagcgcgcg taatacgact cactataggg   2760

cgaattgggt accgggcccc ccctcgaggt cgacggcgcg ccactggtag agagcgactt   2820

tgtatgcccc aattgcgaaa cccgcgatat ccttctcgat tctttagtac ccgaccagga   2880

caaggaaaag gaggtcgaaa cgtttttgaa gaaacaagag gaactacacg gaagctctaa   2940

agatggcaac cagccagaaa ctaagaaaat gaagttgatg gatccaactg gcaccgctgg   3000

cttgaacaac aataccagcc ttccaacttc tgtaaataac ggcggtacgc cagtgccacc   3060

agtaccgtta cctttcggta tacctccttt ccccatgttt ccaatgccct tcatgcctcc   3120

aacggctact atcacaaatc ctcatcaagc tgacgcaagc cctaagaaat gaataacaat   3180

actgacagta ctaaataatt gcctacttgg cttcacatac gttgcatacg tcgatataga   3240

taataatgat aatgacagca ggattatcgt aatacgtaat agctgaaaat ctcaaaaatg   3300

tgtgggtcat tacgtaaata atgataggaa tgggattctt ctatttttcc tttttccatt   3360

ctagcagccg tcgggaaaac gtggcatcct ctctttcggg ctcaattgga gtcacgctgc   3420

cgtgagcatc ctctctttcc atatctaaca actgagcacg taaccaatgg aaaagcatga   3480

gcttagcgtt gctccaaaaa agtattggat ggttaatacc atttgtctgt tctcttctga   3540

ctttgactcc tcaaaaaaaa aaatctacaa tcaacagatc gcttcaatta cgccctcaca   3600

aaaacttttt tccttcttct tcgcccacgt taaattttat ccctcatgtt gtctaacgga   3660

tttctgcact tgatttatta taaaaagaca aagacataat acttctctat caatttcagt   3720

tattgttctt ccttgcgtta ttcttctgtt cttctttttc ttttgtcata tataaccata   3780

accaagtaat acatattcaa actagtatga ctgacaaaaa aactcttaaa gacttaagaa   3840

atcgtagttc tgtttacgat tcaatggtta aatcacctaa tcgtgctatg ttgcgtgcaa   3900

ctggtatgca agatgaagac tttgaaaaac ctatcgtcgg tgtcatttca acttgggctg   3960

aaaacacacc ttgtaatatc cacttacatg actttggtaa actagccaaa gtcggtgtta   4020

aggaagctgg tgcttggcca gttcagttcg gaacaatcac ggtttctgat ggaatcgcca   4080

tgggaaccca aggaatgcgt ttctccttga catctcgtga tattattgca gattctattg   4140
```

-continued

```
aagcagccat gggaggtcat aatgcggatg cttttgtagc cattggcggt tgtgataaaa   4200
acatgcccgg ttctgttatc gctatggcta acatggatat cccagccatt tttgcttacg   4260
gcggaacaat tgcacctggt aatttagacg gcaaagatat cgatttagtc tctgtctttg   4320
aaggtgtcgg ccattggaac cacggcgata tgaccaaaga agaagttaaa gctttggaat   4380
gtaatgcttg tcccggtcct ggaggctgcg gtggtatgta tactgctaac acaatggcga   4440
cagctattga agttttggga cttagccttc cgggttcatc ttctcacccg gctgaatccg   4500
cagaaaagaa agcagatatt gaagaagctg gtcgcgctgt tgtcaaaatg ctcgaaatgg   4560
gcttaaaacc ttctgacatt ttaacgcgtg aagcttttga agatgctatt actgtaacta   4620
tggctctggg aggttcaacc aactcaaccc ttcacctctt agctattgcc catgctgcta   4680
atgtggaatt gacacttgat gatttcaata ctttccaaga aaaagttcct catttggctg   4740
atttgaaacc ttctggtcaa tatgtattcc aagaccttta caaggtcgga ggggtaccag   4800
cagttatgaa atatctcctt aaaaatggct tccttcatgg tgaccgtatc acttgtactg   4860
gcaaaacagt cgctgaaaat ttgaaggctt ttgatgattt aacacctggt caaaaggtta   4920
ttatgccgct tgaaaatcct aaacgtgaag atggtccgct cattattctc catggtaact   4980
tggctccaga cggtgccgtt gccaaagttt ctggtgtaaa agtgcgtcgt catgtcggtc   5040
ctgctaaggt ctttaattct gaagaagaag ccattgaagc tgtcttgaat gatgatattg   5100
ttgatggtga tgttgttgtc gtacgttttg taggaccaaa gggcggtcct ggtatgcctg   5160
aaatgctttc cctttcatca atgattgttg gtaaagggca aggtgaaaaa gttgcccttc   5220
tgacagatgg ccgcttctca ggtggtactt atggtcttgt cgtgggtcat atcgctcctg   5280
aagcacaaga tggcggtcca atcgcctacc tgcaaacagg agacatagtc actattgacc   5340
aagacactaa ggaattacac tttgatatct ccgatgaaga gttaaaacat cgtcaagaga   5400
ccattgaatt gccaccgctc tattcacgcg gtatccttgg taaatatgct cacatcgttt   5460
cgtctgcttc taggggagcc gtaacagact tttggaagcc tgaagaaact ggcaaaaaat   5520
gttgtcctgg ttgctgtggt taagcggccg cgttaattca aattaattga tatagttttt   5580
taatgagtat tgaatctgtt tagaaataat ggaatattat ttttatttat ttatttatat   5640
tattggtcgg ctcttttctt ctgaaggtca atgacaaaat gatatgaagg aaataatgat   5700
ttctaaaatt ttacaacgta agatattttt acaaaagcct agctcatctt ttgtcatgca   5760
ctattttact cacgcttgaa attaacggcc agtccactgc ggagtcattt caaagtcatc   5820
ctaatcgatc tatcgttttt gatagctcat tttggagttc gcgattgtct tctgttattc   5880
acaactgttt taatttttat ttcattctgg aactcttcga gttctttgta aagtctttca   5940
tagtagctta ctttatcctc caacatattt aacttcatgt caatttcggc tcttaaattt   6000
tccacatcat caagttcaac atcatctttt aacttgaatt tattctctag ctcttccaac   6060
caagcctcat tgctccttga tttactggtg aaaagtgata cactttgcgc gcaatccagg   6120
tcaaaacttt cctgcaaaga attcaccaat ttctcgacat catagtacaa tttgttttgt   6180
tctcccatca caatttaata tacctgatgg attcttatga agcgctgggt aatggacgtg   6240
tcactctact tcgccttttt ccctactcct tttagtacgg aagacaatgc taataaataa   6300
gagggtaata ataatattat taatcggcaa aaaagattaa acgccaagcg tttaattatc   6360
agaaagcaaa cgtcgtacca atccttgaat gcttcccaat tgtatattaa gagtcatcac   6420
agcaacatat tcttgttatt aaattaatta ttattgattt ttgatattgt ataaaaaaac   6480
caaatatgta taaaaaaagt gaataaaaaa taccaagtat ggagaaatat attagaagtc   6540
```

```
tatacgttaa accacccggg cccccctcg aggtcgacgg tatcgataag cttgatatcg   6600
aattcctgca gcccggggga tccactagtt ctagagcggc cgctctagaa ctagtaccac   6660
aggtgttgtc ctctgaggac ataaaataca caccgagatt catcaactca ttgctggagt   6720
tagcatatct acaattgggt gaaatgggga gcgatttgca ggcatttgct cggcatgccg   6780
gtagaggtgt ggtcaataag agcgacctca tgctatacct gagaaagcaa cctgacctac   6840
aggaaagagt tactcaagaa taagaatttt cgttttaaaa cctaagagtc actttaaaat   6900
ttgtatacac ttattttttt tataacttat ttaataataa aaatcataaa tcataagaaa   6960
ttcgcttact cttaattaat caggcagcgc ctgcgttcga gaggatgatc ttcatcgcct   7020
tctccttggc gccattgagg aatacctgat aggcgtgctc gatctcggcc agctcgaagc   7080
gatgggtaat catcttcttc aacggaagct tgtcggtcga ggcgaccttc atcagcatgg   7140
gcgtcgtgtt cgtgttcacc agtcccgtgg tgatcgtcag gttcttgatc cagagcttct   7200
gaatctcgaa gtcaaccttg acgccatgca cgccgacgtt ggcgatgtgc gcgccgggct   7260
tgacgatctc ctggcagatg tcccaagtcg ccggtatgcc caccgcctcg atcgcaacat   7320
cgactccctc tgccgcaatc ctatgcacgg cttcgacaac gttctccgtg ccggagttga   7380
tggtgtgcgt tgccccgagc tccttggcga gctggaggcg attctcgtcc atgtcgatca   7440
cgatgatggt cgagggggag tagaactggg cggtcaacag tacggacatg ccgacggggc   7500
ccgcgccgac aatagccacc gcatcgcccg gctggacatt cccatactgg acgccgattt   7560
cgtggccggt gggcaggatg tcgctcagca ggacggcgat ttcgtcgtca attgtctggg   7620
ggatcttgta gaggctgttg tcggcatgcg ggatgcggac gtattcggcc tgcacgccat   7680
cgatcatgta acccaggatc cacccgccgt cgcggcaatg ggagtaaagc tgcttcttgc   7740
agtagtcgca cgagccgcaa gaagtgacgc aggaaatcag gaccttgtcg cctttcttga   7800
actgcgtgac actctcgccc acttcctcga tgacgcctac cccttcatgg cccaggatgc   7860
gcccgtcggc gacctctgga ttcttgcctt tgtagatgcc gagatccgtg ccgcagatcg   7920
tggtcttcaa aacccgtact actacatccg tgggcttttg aagggtgggc ttgggcttgt   7980
cttcaagcga gatcttgtgg tcaccgtgat aaaccagagc tttcatcctc agctattgta   8040
atatgtgtgt ttgtttggat tattaagaag aataattaca aaaaaaatta caaaggaagg   8100
taattacaac agaattaaga aaggacaaga aggaggaaga gaatcagttc attatttctt   8160
ctttgttata taacaaaccc aagtagcgat ttggccatac attaaaagtt gagaaccacc   8220
ctccctggca acagccacaa ctcgttacca ttgttcatca cgatcatgaa actcgctgtc   8280
agctgaaatt tcacctcagt ggatctctct ttttattctt catcgttcca ctaacctttt   8340
tccatcagct ggcagggaac ggaaagtgga atcccattta gcgagcttcc tcttttcttc   8400
aagaaaagac gaagcttgtg tgtgggtgcg cgcgctagta tctttccaca ttaagaaata   8460
taccataaag gttacttaga catcactatg gctatatata tatatatata tatatatgta   8520
acttagcacc atcgcgcgtg catcactgca tgtgttaacc gaaaagtttg gcgaacactt   8580
caccgacacg gtcatttaga tctgtcgtct gcattgcacg tcccttagcc ttaaatccta   8640
ggcgggagca ttctcgtgta attgtgcagc ctgcgtagca actcaacata gcgtagtcta   8700
cccagttttt caagggttta tcgttagaag attctccctt ttcttcctgc tcacaaatct   8760
taaagtcata cattgcacga ctaaatgcaa gcatgcggat cccccgggct gcaggaattc   8820
gatatcaagc ttatcgatac cgtcgactgg ccattaatct ttcccatatt agatttcgcc   8880
aagccatgaa agttcaagaa aggtctttag acgaattacc cttcatttct caaactggcg   8940
```

-continued

```
tcaagggatc ctggtatggt tttatcgttt tatttctggt tcttatagca tcgttttgga   9000
cttctctgtt cccattaggc ggttcaggag ccagcgcaga atcattcttt gaaggatact   9060
tatcctttcc aattttgatt gtctgttacg ttggacataa actgtatact agaaattgga   9120
ctttgatggt gaaactagaa gatatggatc ttgataccgg cagaaaacaa gtagatttga   9180
ctcttcgtag ggaagaaatg aggattgagc gagaaacatt agcaaaaaga tccttcgtaa   9240
caagattttt acatttctgg tgttgaaggg aaagatatga gctatacagc ggaatttcca   9300
tatcactcag attttgttat ctaatttttt ccttcccacg tccgcgggaa tctgtgtata   9360
ttactgcatc tagatatatg ttatcttatc ttggcgcgta catttaattt tcaacgtatt   9420
ctataagaaa ttgcgggagt ttttttcatg tagatgatac tgactgcacg caaatatagg   9480
catgatttat aggcatgatt tgatggctgt accgatagga acgctaagag taacttcaga   9540
atcgttatcc tggcggaaaa aattcatttg taaactttaa aaaaaaaagc caatatcccc   9600
aaaattatta agagcgcctc cattattaac taaaatttca ctcagcatcc acaatgtatc   9660
aggtatctac tacagatatt acatgtggcg aaaaagacaa gaacaatgca atagcgcatc   9720
aagaaaaaac acaaagcttt caatcaatga atcgaaaatg tcattaaaat agtatataaa   9780
ttgaaactaa gtcataaagc tataaaaaga aaatttattt aaatgcaaga tttaaagtaa   9840
attcacggcc ctgcaggcct cagctcttgt tttgttctgc aaataactta cccatctttt   9900
tcaaaacttt aggtgcaccc tcctttgcta gaataagttc tatccaatac atcctatttg   9960
gatctgcttg agcttctttc atcacggata cgaattcatt ttctgttctc acaattttgg  10020
acacaactct gtcttccgtt gccccgaaac tttctggcag ttttgagtaa ttccacatag  10080
gaatgtcatt ataactctgg ttcggaccat gaatttccct ctcaaccgtg taaccatcgt  10140
tattaatgat aaagcagatt gggtttatct tctctctaat ggctagtcct aattcttgga  10200
cagtcagttg caatgatcca tctccgataa acaataaatg tctagattct ttatctgcaa  10260
tttggctgcc tagagctgcg gggaaagtgt atcctataga tccccacaag ggttgaccaa  10320
taaaatgtga tttcgatttc agaaatatag atgaggcacc gaagaaagaa gtgccttgtt  10380
cagccacgat cgtctcatta ctttgggtca aattttcgac agcttgccac agtctatctt  10440
gtgacaacag cgcgttagaa ggtacaaaat cttcttgctt tttatctatg tacttgcctt  10500
tatattcaat ttcggacaag tcaagaagag atgatatcag ggattcgaag tcgaaatttt  10560
ggattctttc gttgaaaatt ttaccttcat cgatattcaa ggaaatcatt ttattttcat  10620
taagatggtg agtaaatgca cccgtactag aatcggtaag ctttacaccc aacataagaa  10680
taaaatcagc agattccaca aattccttca agtttggctc tgacagagta ccgttgtaaa  10740
tccccaaaaa tgagggcaat gcttcatcaa cagatgattt accaaagttc aaagtagtaa  10800
taggtaactt agtctttgaa ataaactgag taacagtctt ctctaggccg aacgatataa  10860
tttcatggcc tgtgattaca attggtttct tggcattctt cagactttcc tgtattttgt  10920
tcagaatctc ttgatcagat gtattcgacg tggaattttc cttcttaaga ggcaaggatg  10980
gtttttcagc cttagcggca gctacatcta caggtaaatt gatgtaaacc ggctttcttt  11040
cctttagtaa ggcagacaac actctatcaa tttcaacagt tgcattctcg gctgtcaata  11100
aagtcctggc agcagtaacc ggttcgtgca tcttcataaa gtgcttgaaa tcaccatcag  11160
ccaacgtatg gtgaacaaac ttaccttcgt tctgcacttt cgaggtagga gatcccacga  11220
tctcaacaac aggcaggttc tcagcatagg agcccgctaa gccattaact gcggataatt  11280
cgccaacacc aaatgtagtc aagaatgccg cagccttttt cgttcttgcg tacccgtcgg  11340
```

```
ccatatagga ggcatttaac tcattagcat ttcccaccca tttcatatct ttgtgtgaaa  11400
taatttgatc tagaaattgc aaattgtagt cacctggtac tccgaatatt tcttctatac  11460
ctaattcgtg taatctgtcc aacagatagt cacctactgt atacattttg tttactagtt  11520
tatgtgtgtt tattcgaaac taagttcttg gtgttttaaa actaaaaaaa agactaacta  11580
taaaagtaga atttaagaag tttaagaaat agatttacag aattacaatc aatacctacc  11640
gtctttatat acttattagt caagtagggg aataatttca gggaactggt ttcaaccttt  11700
tttttcagct ttttccaaat cagagagagc agaaggtaat agaaggtgta agaaaatgag  11760
atagatacat gcgtgggtca attgccttgt gtcatcattt actccaggca ggttgcatca  11820
ctccattgag gttgtgcccg ttttttgcct gtttgtgccc ctgttctctg tagttgcgct  11880
aagagaatgg acctatgaac tgatggttgg tgaagaaaac aatattttgg tgctgggatt  11940
cttttttttt ctggatgcca gcttaaaaag cgggctccat tatatttagt ggatgccagg  12000
aataaactgt tcacccagac acctacgatg ttatatattc tgtgtaaccc gccccctatt  12060
ttgggcatgt acgggttaca gcagaattaa aaggctaatt ttttgactaa ataaagttag  12120
gaaaatcact actattaatt atttacgtat tctttgaaat ggcagtattg ataatgataa  12180
actcgaactg aaaaagcgtg ttttttattc aaaatgattc taactccctt acgtaatcaa  12240
ggaatctttt tgccttggcc tccgcgtcat taaacttctt gttgttgacg ctaacattca  12300
acgctagtat atattcgttt ttttcaggta agttcttttc aacgggtctt actgatgagg  12360
cagtcgcgtc tgaacctgtt aagaggtcaa atatgtcttc ttgaccgtac gtgtcttgca  12420
tgttattagc tttgggaatt tgcatcaagt cataggaaaa tttaaatctt ggctctcttg  12480
ggctcaaggt gacaaggtcc tcgaaaatag ggcgcgcccc accgcggtgg agctccagct  12540
tttgttccct ttagtgaggg ttaattgcgc gcttggcgta atcatggtca tagctgtttc  12600
ctgtgtgaaa ttgttatccg ctcacaattc cacacaacat acgagccgga agcataaagt  12660
gtaaagcctg gggtgcctaa tgagtgagct aactcacatt aattgcgttg cgctcactgc  12720
ccgctttcca gtcgggaaac ctgtcgtgcc agctgcatta atgaatcggc caacgcgcgg  12780
ggagaggcgg tttgcgtatt gggcgctctt ccgcttcctc gctcactgac tcgctgcgct  12840
cggtcgttcg gctgcggcga gcggtatcag ctcactcaaa ggcggtaata cggttatcca  12900
cagaatcagg ggataacgca ggaaagaaca tgtgagcaaa aggccagcaa aaggccagga  12960
accgtaaaaa ggccgcgttg ctggcgtttt tccataggct ccgcccccct gacgagcatc  13020
acaaaaatcg acgctcaagt cagaggtggc gaaacccgac aggactataa agataccagg  13080
cgtttccccc tggaagctcc ctcgtgcgct ctcctgttcc gaccctgccg cttaccggat  13140
acctgtccgc ctttctccct tcgggaagcg tggcgctttc tcatagctca cgctgtaggt  13200
atctcagttc ggtgtaggtc gttcgctcca agctgggctg tgtgcacgaa ccccccgttc  13260
agcccgaccg ctgcgcctta tccggtaact atcgtcttga gtccaacccg gtaagacacg  13320
acttatcgcc actggcagca gccactggta acaggattag cagagcgagg tatgtaggcg  13380
gtgctacaga gttcttgaag tggtggccta actacggcta cactagaaga acagtatttg  13440
gtatctgcgc tctgctgaag ccagttacct tcggaaaaag agttggtagc tcttgatccg  13500
gcaaacaaac caccgctggt agcggtggtt tttttgtttg caagcagcag attacgcgca  13560
gaaaaaaagg atctcaagaa gatcctttga tcttttctac ggggtctgac gctcagtgga  13620
acgaaaactc acgttaaggg attttggtca tgagattatc aaaaaggatc ttcacctaga  13680
tccttttaaa ttaaaaatga agttttaaat caatctaaag tatatatgag taaacttggt  13740
```

```
ctgacagtta ccaatgctta atcagtgagg cacctatctc agcgatctgt ctatttcgtt  13800

catccatagt tgcctgactc cccgtcgtgt agataactac gatacgggag ggcttaccat  13860

ctggccccag tgctgcaatg ataccgcgag acccacgctc accggctcca gatttatcag  13920

caataaacca gccagccgga agggccgagc gcagaagtgg tcctgcaact ttatccgcct  13980

ccatccagtc tattaattgt tgccgggaag ctagagtaag tagttcgcca gttaatagtt  14040

tgcgcaacgt tgttgccatt gctacaggca tcgtggtgtc acgctcgtcg tttggtatgg  14100

cttcattcag ctccggttcc caacgatcaa ggcgagttac atgatccccc atgttgtgca  14160

aaaaagcggt tagctccttc ggtcctccga tcgttgtcag aagtaagttg gccgcagtgt  14220

tatcactcat ggttatggca gcactgcata attctcttac tgtcatgcca tccgtaagat  14280

gcttttctgt gactggtgag tactcaacca agtcattctg agaatagtgt atgcggcgac  14340

cgagttgctc ttgcccggcg tcaatacggg ataataccgc gccacatagc agaactttaa  14400

aagtgctcat cattggaaaa cgttcttcgg ggcgaaaact ctcaaggatc ttaccgctgt  14460

tgagatccag ttcgatgtaa cccactcgtg cacccaactg atcttcagca tcttttactt  14520

tcaccagcgt ttctgggtga gcaaaaacag gaaggcaaaa tgccgcaaaa aagggaataa  14580

gggcgacacg gaaatgttga atactcatac tcttcctttt tcaatattat tgaagcattt  14640

atcagggtta ttgtctcatg agcggataca tatttgaatg tatttagaaa aataaacaaa  14700

taggggttcc gcgcacattt ccccgaaaag tgccacctga acgaagcatc tgtgcttcat  14760

tttgtagaac aaaaatgcaa cgcgagagcg ctaatttttc aaacaaagaa tctgagctgc  14820

atttttacag aacagaaatg caacgcgaaa gcgctatttt accaacgaag aatctgtgct  14880

tcatttttgt aaaacaaaaa tgcaacgcga gagcgctaat ttttcaaaca aagaatctga  14940

gctgcatttt tacagaacag aaatgcaacg cgagagcgct attttaccaa caaagaatct  15000

atacttcttt tttgttctac aaaaatgcat cccgagagcg ctatttttct aacaaagcat  15060

cttagattac tttttttctc ctttgtgcgc tctataatgc agtctcttga taactttttg  15120

cactgtaggt ccgttaaggt tagaagaagg ctactttggt gtctattttc tcttccataa  15180

aaaaagcctg actccacttc ccgcgtttac tgattactag cgaagctgcg ggtgcatttt  15240

ttcaagataa aggcatcccc gattatattc tataccgatg tggattgcgc atactttgtg  15300

aacagaaagt gatagcgttg atgattcttc attggtcaga aaattatgaa cggtttcttc  15360

tattttgtct ctatatacta cgtataggaa atgtttacat ttcgtattg ttttcgattc  15420

actctatgaa tagttcttac tacaattttt ttgtct                          15456
```

<210> SEQ ID NO 68
<211> LENGTH: 1559
<212> TYPE: DNA
<213> ORGANISM: Artificial Sequence
<220> FEATURE:
<223> OTHER INFORMATION: Template

<400> SEQUENCE: 68

```
gcattgcgga ttacgtattc taatgttcag taccgttcgt ataatgtatg ctatacgaag     60

ttatgcagat tgtactgaga gtgcaccata ccaccttttc aattcatcat ttttttttta    120

ttcttttttt tgatttcggt ttccttgaaa tttttttgat tcggtaatct ccgaacagaa    180

ggaagaacga aggaaggagc acagacttag attggtatat atacgcatat gtagtgttga    240

agaaacatga aattgcccag tattcttaac ccaactgcac agaacaaaaa cctgcaggaa    300

acgaagataa atcatgtcga aagctacata taaggaacgt gctgctactc atcctagtcc    360
```

```
tgttgctgcc aagctattta atatcatgca cgaaaagcaa acaaacttgt gtgcttcatt    420

ggatgttcgt accaccaagg aattactgga gttagttgaa gcattaggtc ccaaaatttg    480

tttactaaaa acacatgtgg atatcttgac tgatttttcc atggagggca cagttaagcc    540

gctaaaggca ttatccgcca agtacaattt tttactcttc gaagacagaa aatttgctga    600

cattggtaat acagtcaaat tgcagtactc tgcgggtgta tacagaatag cagaatgggc    660

agacattacg aatgcacacg gtgtggtggg cccaggtatt gttagcggtt tgaagcaggc    720

ggcagaagaa gtaacaaagg aacctagagg ccttttgatg ttagcagaat tgtcatgcaa    780

gggctcccta tctactggag aatatactaa gggtactgtt gacattgcga agagcgacaa    840

agattttgtt atcggcttta ttgctcaaag agacatgggt ggaagagatg aaggttacga    900

ttggttgatt atgacacccg gtgtgggttt agatgacaag ggagacgcat tgggtcaaca    960

gtatagaacc gtggatgatg tggtctctac aggatctgac attattattg ttggaagagg   1020

actatttgca aagggaaggg atgctaaggt agagggtgaa cgttacagaa aagcaggctg   1080

ggaagcatat ttgagaagat gcggccagca aaactaaaaa actgtattat aagtaaatgc   1140

atgtatacta aactcacaaa ttagagcttc aatttaatta tatcagttat taccctatgc   1200

ggtgtgaaat accgcacaga tgcgtaagga gaaaataccg catcaggaaa ttgtaaacgt   1260

taatattttg ttaaaattcg cgttaaattt ttgttaaatc agctcatttt ttaaccaata   1320

ggccgaaatc ggcaaaatcc cttataaatc aaaagaatag accgagatag ggttgagtgt   1380

tgttccagtt tggaacaaga gtccactatt aaagaacgtg gactccaacg tcaaagggcg   1440

aaaaaccgtc tatcagggcg atggcccact acgtgaacca tcaccctaat caagataact   1500

tcgtataatg tatgctatac gaacggtacc agtgatgata caacgagtta gccaaggtg    1559
```

<210> SEQ ID NO 69
<211> LENGTH: 1047
<212> TYPE: DNA
<213> ORGANISM: Alcaligenes xylosoxydans

<400> SEQUENCE: 69

```
atgaaagctc tggtttatca cggtgaccac aagatctcgc ttgaagacaa gcccaagccc     60

acccttcaaa agcccacgga tgtagtagta cgggttttga agaccacgat ctgcggcacg    120

gatctcggca tctacaaagg caagaatcca gaggtcgccg acgggcgcat cctgggccat    180

gaaggggtag gcgtcatcga ggaagtgggc gagagtgtca cgcagttcaa gaaaggcgac    240

aaggtcctga tttcctgcgt cacttcttgc ggctcgtgcg actactgcaa gaagcagctt    300

tactcccatt gccgcgacgg cgggtggatc ctgggttaca tgatcgatgg cgtgcaggcc    360

gaatacgtcc gcatcccgca tgccgacaac agcctctaca agatccccca gacaattgac    420

gacgaaatcg ccgtcctgct gagcgacatc ctgcccaccg gccacgaaat cggcgtccag    480

tatgggaatg tccagccggg cgatgcggtg gctattgtcg gcgcgggccc cgtcggcatg    540

tccgtactgt tgaccgccca gttctactcc ccctcgacca tcatcgtgat cgacatggac    600

gagaatcgcc tccagctcgc caaggagctc ggggcaacgc acaccatcaa ctccggcacg    660

gagaacgttg tcgaagccgt gcataggatt gcggcagagg gagtcgatgt tgcgatcgag    720

gcggtgggca taccggcgac ttgggacatc tgccaggaga tcgtcaagcc cggcgcgcac    780

atcgccaacg tcggcgtgca tggcgtcaag gttgacttcg agattcagaa gctctggatc    840

aagaacctga cgatcaccac gggactggtg aacacgaaca cgacgcccat gctgatgaag    900

gtcgcctcga ccgacaagct tccgttgaag aagatgatta cccatcgctt cgagctggcc    960
```

```
gagatcgagc acgcctatca ggtattcctc aatggcgcca aggagaaggc gatgaagatc   1020

atcctctcga acgcaggcgc tgcctga                                        1047


<210> SEQ ID NO 70
<211> LENGTH: 348
<212> TYPE: PRT
<213> ORGANISM: Alcaligenes xylosoxydans

<400> SEQUENCE: 70

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 71
```

<211> LENGTH: 1644
<212> TYPE: DNA
<213> ORGANISM: Artificial Sequence
<220> FEATURE:
<223> OTHER INFORMATION: codon optimized L. lactis kivD coding region for S. cerevisiae expression

<400> SEQUENCE: 71

```
atgtatacag taggtgacta tctgttggac agattacacg aattaggtat agaagaaata     60
ttcggagtac caggtgacta caatttgcaa tttctagatc aaattatttc acacaaagat    120
atgaaatggg tgggaaatgc taatgagtta aatgcctcct atatggccga cgggtacgca    180
agaacgaaaa aggctgcggc attcttgact acatttggtg ttggcgaatt atccgcagtt    240
aatggcttag cgggctccta tgctgagaac ctgcctgttg ttgagatcgt gggatctcct    300
acctcgaaag tgcagaacga aggtaagttt gttcaccata cgttggctga tggtgatttc    360
aagcacttta tgaagatgca cgaaccggtt actgctgcca ggactttatt gacagccgag    420
aatgcaactg ttgaaattga tagagtgttg tctgccttac taaaggaaag aaagccggtt    480
tacatcaatt tacctgtaga tgtagctgcc gctaaggctg aaaaaccatc cttgcctctt    540
aagaaggaaa attccacgtc gaatacatct gatcaagaga ttctgaacaa aatacaggaa    600
agtctgaaga atgccaagaa accaattgta atcacaggcc atgaaattat atcgttcggc    660
ctagagaaga ctgttactca gtttatttca aagactaagt tacctattac tactttgaac    720
tttggtaaat catctgttga tgaagcattg ccctcatttt tggggattta caacggtact    780
ctgtcagagc caaacttgaa ggaatttgtg gaatctgctg attttattct tatgttgggt    840
gtaaagctta ccgattctag tacgggtgca tttactcacc atcttaatga aaataaaatg    900
atttccttga atatcgatga aggtaaaatt ttcaacgaaa gaatccaaaa tttcgacttc    960
gaatccctga tatcatctct tcttgacttg tccgaaattg aatataaagg caagtacata   1020
gataaaaagc aagaagattt tgtaccttct aacgcgctgt tgtcacaaga tagactgtgg   1080
caagctgtcg aaaatttgac ccaaagtaat gagacgatcg tggctgaaca aggcacttct   1140
ttcttcggtg cctcatctat atttctgaaa tcgaaatcac attttattgg tcaacccttg   1200
tggggatcta taggatacac tttccccgca gctctaggca gccaaattgc agataaagaa   1260
tctagacatt tattgtttat cggagatgga tcattgcaac tgactgtcca agaattagga   1320
ctagccatta gagagaagat aaacccaatc tgctttatca ttaataacga tggttacacg   1380
gttgagaggg aaattcatgg tccgaaccag agttataatg acattcctat gtggaattac   1440
tcaaaactgc cagaaagttt cggggcaacg gaagacagag ttgtgtccaa aattgtgaga   1500
acagaaaatg aattcgtatc cgtgatgaaa gaagctcaag cagatccaaa taggatgtat   1560
tggatagaac ttattctagc aaaggagggt gcacctaaag ttttgaaaaa gatgggtaag   1620
ttatttgcag aacaaaacaa gagc                                          1644
```

<210> SEQ ID NO 72
<211> LENGTH: 753
<212> TYPE: DNA
<213> ORGANISM: Saccharomyces cerevisiae

<400> SEQUENCE: 72

```
gcatgcttgc atttagtcgt gcaatgtatg actttaagat ttgtgagcag gaagaaaagg     60
gagaatcttc taacgataaa cccttgaaaa actgggtaga ctacgctatg ttgagttgct    120
acgcaggctg cacaattaca cgagaatgct cccgcctagg atttaaggct aagggacgtg    180
caatgcagac gacagatcta aatgaccgtg tcggtgaagt gttcgccaaa cttttcggtt    240
```

aacacatgca gtgatgcacg cgcgatggtg ctaagttaca tatatatata tatagccata 300
gtgatgtcta agtaaccttt atggtatatt tcttaatgtg gaaagatact agcgcgcgca 360
cccacacaca agcttcgtct ttcttgaag aaaagaggaa gctcgctaaa tgggattcca 420
ctttccgttc cctgccagct gatggaaaaa ggttagtgga acgatgaaga ataaaaagag 480
agatccactg aggtgaaatt tcagctgaca gcgagtttca tgatcgtgat gaacaatggt 540
aacgagttgt ggctgttgcc agggagggtg gttctcaact tttaatgtat ggccaaatcg 600
ctacttgggt ttgttatata acaaagaaga aataatgaac tgattctctt cctccttctt 660
gtcctttctt aattctgttg taattacctt cctttgtaat tttttttgta attattcttc 720
ttaataatcc aaacaaacac acatattaca ata 753

<210> SEQ ID NO 73
<211> LENGTH: 316
<212> TYPE: DNA
<213> ORGANISM: Saccharomyces cerevisiae

<400> SEQUENCE: 73
gagtaagcga atttcttatg atttatgatt tttattatta aataagttat aaaaaaaata 60
agtgtataca aattttaaag tgactcttag gttttaaaac gaaaattctt attcttgagt 120
aactctttcc tgtaggtcag gttgctttct caggtatagc atgaggtcgc tcttattgac 180
cacacctcta ccggcatgcc gagcaaatgc ctgcaaatcg ctccccattt cacccaattg 240
tagatatgct aactccagca atgagttgat gaatctcggt gtgtatttta tgtcctcaga 300
ggacaacacc tgtggt 316

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
ggaattcaca catgaaagct ctggtttatc 30

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
gcgtccaggg cgtcaaagat caggcagc 28

<210> SEQ ID NO 76
<211> LENGTH: 55
<212> TYPE: DNA
<213> ORGANISM: Artificial Sequence
<220> FEATURE:
<223> OTHER INFORMATION: Primer

<400> SEQUENCE: 76
aaacaaacac acatattaca atagctgagg atgaaagctc tggtttatca cggtg 55

<210> SEQ ID NO 77
<211> LENGTH: 55
<212> TYPE: DNA
<213> ORGANISM: Artificial Sequence
<220> FEATURE:
<223> OTHER INFORMATION: primer

<400> SEQUENCE: 77
atcataagaa attcgcttac tcttaattaa tcaggcagcg cctgcgttcg agagg 55

<210> SEQ ID NO 78
<211> LENGTH: 8994
<212> TYPE: DNA
<213> ORGANISM: Artificial Sequence
<220> FEATURE:
<223> OTHER INFORMATION: constructed plasmid

<400> SEQUENCE: 78
ctagttctag agcggccgcc accgcggtgg agctccagct tttgttccct ttagtgaggg 60
ttaattgcgc gcttggcgta atcatggtca tagctgtttc ctgtgtgaaa ttgttatccg 120
ctcacaattc cacacaacat aggagccgga agcataaagt gtaaagcctg gggtgcctaa 180
tgagtgaggt aactcacatt aattgcgttg cgctcactgc ccgctttcca gtcgggaaac 240
ctgtcgtgcc agctgcatta atgaatcggc caacgcgcgg ggagaggcgg tttgcgtatt 300
gggcgctctt ccgcttcctc gctcactgac tcgctgcgct cggtcgttcg gctgcggcga 360
gcggtatcag ctcactcaaa ggcggtaata cggttatcca cagaatcagg ggataacgca 420
ggaaagaaca tgtgagcaaa aggccagcaa aaggccagga accgtaaaaa ggccgcgttg 480
ctggcgtttt tccataggct ccgcccccct gacgagcatc acaaaaatcg acgctcaagt 540
cagaggtggc gaaacccgac aggactataa agataccagg cgtttccccc tggaagctcc 600
ctcgtgcgct ctcctgttcc gaccctgccg cttaccggat acctgtccgc ctttctccct 660
tcgggaagcg tggcgctttc tcatagctca cgctgtaggt atctcagttc ggtgtaggtc 720
gttcgctcca agctgggctg tgtgcacgaa ccccccgttc agcccgaccg ctgcgcctta 780
tccggtaact atcgtcttga gtccaacccg gtaagacacg acttatcgcc actggcagca 840
gccactggta acaggattag cagagcgagg tatgtaggcg gtgctacaga gttcttgaag 900
tggtggccta actacggcta cactagaagg acagtatttg gtatctgcgc tctgctgaag 960
ccagttacct tcggaaaaag agttggtagc tcttgatccg gcaaacaaac caccgctggt 1020
agcggtggtt tttttgtttg caagcagcag attacgcgca gaaaaaaagg atctcaagaa 1080
gatcctttga tcttttctac ggggtctgac gctcagtgga acgaaaactc acgttaaggg 1140
attttggtca tgagattatc aaaaaggatc ttcacctaga tccttttaaa ttaaaaatga 1200
agttttaaat caatctaaag tatatatgag taaacttggt ctgacagtta ccaatgctta 1260
atcagtgagg cacctatctc agcgatctgt ctatttcgtt catccatagt tgcctgactc 1320
cccgtcgtgt agataactac gatacgggag ggcttaccat ctggccccag tgctgcaatg 1380
ataccgcgag acccacgctc accggctcca gatttatcag caataaacca gccagccgga 1440
agggccgagc gcagaagtgg tcctgcaact ttatccgcct ccatccagtc tattaattgt 1500
tgccgggaag ctagagtaag tagttcgcca gttaatagtt tgcgcaacgt tgttgccatt 1560
gctacaggca tcgtggtgtc acgctcgtcg tttggtatgg cttcattcag ctccggttcc 1620
caacgatcaa ggcgagttac atgatccccc atgttgtgca aaaaagcggt tagctccttc 1680
ggtcctccga tcgttgtcag aagtaagttg gccgcagtgt tatcactcat ggttatggca 1740
gcactgcata attctcttac tgtcatgcca tccgtaagat gcttttctgt gactggtgag 1800
tactcaacca agtcattctg agaatagtgt atgcggcgac cgagttgctc ttgcccggcg 1860
tcaatacggg ataataccgc gccacatagc agaactttaa aagtgctcat cattggaaaa 1920

```
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaatttttc aaacaaagaa tctgagctgc atttttacag aacagaaatg   2340
caacgcgaaa gcgctatttt accaacgaag aatctgtgct tcatttttgt aaaacaaaaa   2400
tgcaacgcga gagcgctaat ttttcaaaca aagaatctga gctgcatttt tacagaacag   2460
aaatgcaacg cgagagcgct attttaccaa caaagaatct atacttcttt tttgttctac   2520
aaaaatgcat cccgagagcg ctatttttct aacaaagcat cttagattac tttttttctc   2580
ctttgtgcgc tctataatgc agtctcttga taactttttg cactgtaggt ccgttaaggt   2640
tagaagaagg ctactttggt gtctattttc tcttccataa aaaaagcctg actccacttc   2700
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt tttttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct tttccttat cacgttgagc cattagtatc aatttgctta   4140
cctgtattcc tttactatcc tcctttttct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
```

```
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca tttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaatttttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
aagggggatg tgctgcaagg cgattaagtt gggtaacgcc agggttttcc cagtcacgac   6720
```

```
gttgtaaaac gacggccagt gagcgcgcgt aatacgactc actatagggc gaattgggta   6780
ccgggccccc cctcgaggtc gacggtatcg ataagcttga tatcgaattc ctgcagcccg   6840
ggggatccgc atgcttgcat ttagtcgtgc aatgtatgac tttaagattt gtgagcagga   6900
agaaaaggga gaatcttcta acgataaacc cttgaaaaac tgggtagact acgctatgtt   6960
gagttgctac gcaggctgca caattacacg agaatgctcc cgcctaggat ttaaggctaa   7020
gggacgtgca atgcagacga cagatctaaa tgaccgtgtc ggtgaagtgt tcgccaaact   7080
tttcggttaa cacatgcagt gatgcacgcg cgatggtgct aagttacata tatatatata   7140
tatatatata tagccatagt gatgtctaag taacctttat ggtatatttc ttaatgtgga   7200
aagatactag cgcgcgcacc cacacacaag cttcgtcttt tcttgaagaa aagaggaagc   7260
tcgctaaatg ggattccact ttccgttccc tgccagctga tggaaaaagg ttagtggaac   7320
gatgaagaat aaaaagagag atccactgag gtgaaatttc agctgacagc gagtttcatg   7380
atcgtgatga acaatggtaa cgagttgtgg ctgttgccag ggagggtggt tctcaacttt   7440
taatgtatgg ccaaatcgct acttgggttt gttatataac aaagaagaaa taatgaactg   7500
attctcttcc tccttcttgt cctttcttaa ttctgttgta attaccttcc tttgtaattt   7560
tttttgtaat tattcttctt aataatccaa acaaacacac atattacaat agctagctga   7620
ggatgaaggc attagtttat catggggatc acaaaatttc gttagaagac aaaccaaaac   7680
ccactctgca gaaaccaaca gacgttgtgg ttagggtgtt gaaaacaaca atttgcggta   7740
ctgacttggg aatatacaaa ggtaagaatc ctgaagtggc agatggcaga atcctgggtc   7800
atgagggcgt tggcgtcatt gaagaagtgg gcgaatccgt gacacaattc aaaaaggggg   7860
ataaagtttt aatctcctgc gttactagct gtggatcgtg tgattattgc aagaagcaac   7920
tgtattcaca ctgtagagac ggtggctgga ttttaggtta catgatcgac ggtgtccaag   7980
ccgaatacgt cagaatacca catgctgaca attcattgta taagatcccg caaactatcg   8040
atgatgaaat tgcagtacta ctgtccgata ttttacctac tggacatgaa attggtgttc   8100
aatatggtaa cgttcaacca ggcgatgctg tagcaattgt aggagcaggt cctgttggaa   8160
tgtcagtttt gttaactgct caattttact cgcctagtac cattattgtt atcgacatgg   8220
acgaaaaccg tttacaatta gcgaaggagc ttggggccac acacactatt aactccggta   8280
ctgaaaatgt tgtcgaagct gtgcatcgta tagcagccga aggagtggat gtagcaatag   8340
aagctgttgg tatacccgca acctgggaca tctgtcagga aattgtaaaa cccggcgctc   8400
atattgccaa cgtgggagtt catggtgtta aggtggactt tgaaattcaa aagttgtgga   8460
ttaagaatct aaccatcacc actggtttgg ttaacactaa tactacccca atgttgatga   8520
aggtagcctc tactgataaa ttgcctttaa agaaaatgat tactcacagg tttgagttag   8580
ctgaaatcga acacgcatat caggttttct tgaatggcgc taaagaaaaa gctatgaaga   8640
ttattctatc taatgcaggt gccgcctaat taattaagag taagcgaatt tcttatgatt   8700
tatgattttt attattaaat aagttataaa aaaaataagt gtatacaaat tttaaagtga   8760
ctcttaggtt ttaaaacgaa aattcttatt cttgagtaac tctttcctgt aggtcaggtt   8820
gctttctcag gtatagcatg aggtcgctct tattgaccac acctctaccg gcatgccgag   8880
caaatgcctg caaatcgctc cccatttcac ccaattgtag atatgctaac tccagcaatg   8940
agttgatgaa tctcggtgtg tattttatgt cctcagagga caacacctgt ggta         8994
```

<210> SEQ ID NO 79
<211> LENGTH: 2145

<212> TYPE: DNA
<213> ORGANISM: Artificial Sequence
<220> FEATURE:
<223> OTHER INFORMATION: constructed chimeric gene

<400> SEQUENCE: 79

```
gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatatatata    300

tatagccata gtgatgtcta agtaaccttt atggtatatt tcttaatgtg gaaagatact    360

agcgcgcgca cccacacaca agcttcgtct tttcttgaag aaaagaggaa gctcgctaaa    420

tgggattcca ctttccgttc cctgccagct gatggaaaaa ggttagtgga acgatgaaga    480

ataaaaagag agatccactg aggtgaaatt tcagctgaca gcgagtttca tgatcgtgat    540

gaacaatggt aacgagttgt ggctgttgcc agggagggtg gttctcaact tttaatgtat    600

ggccaaatcg ctacttgggt ttgttatata acaaagaaga aataatgaac tgattctctt    660

cctccttctt gtcctttctt aattctgttg taattacctt cctttgtaat ttttttgta     720

attattcttc ttaataatcc aaacaaacac acatattaca atagctagct gaggatgaag    780

gcattagttt atcatgggga tcacaaaatt tcgttagaag acaaaccaaa acccactctg    840

cagaaaccaa cagacgttgt ggttagggtg ttgaaaacaa caatttgcgg tactgacttg    900

ggaatataca aaggtaagaa tcctgaagtg gcagatggca gaatcctggg tcatgagggc    960

gttggcgtca ttgaagaagt gggcgaatcc gtgacacaat tcaaaaaggg ggataaagtt   1020

ttaatctcct gcgttactag ctgtggatcg tgtgattatt gcaagaagca actgtattca   1080

cactgtagag acggtggctg gattttaggt tacatgatcg acggtgtcca agccgaatac   1140

gtcagaatac cacatgctga caattcattg tataagatcc cgcaaactat cgatgatgaa   1200

attgcagtac tactgtccga tattttacct actggacatg aaattggtgt tcaatatggt   1260

aacgttcaac caggcgatgc tgtagcaatt gtaggagcag gtcctgttgg aatgtcagtt   1320

ttgttaactg ctcaatttta ctcgcctagt accattattg ttatcgacat ggacgaaaac   1380

cgtttacaat tagcgaagga gcttggggcc acacacacta ttaactccgg tactgaaaat   1440

gttgtcgaag ctgtgcatcg tatagcagcc gaaggagtgg atgtagcaat agaagctgtt   1500

ggtatacccg caacctggga catctgtcag gaaattgtaa aacccggcgc tcatattgcc   1560

aacgtgggag ttcatggtgt taaggtggac tttgaaattc aaaagttgtg gattaagaat   1620

ctaaccatca ccactggttt ggttaacact aatactaccc caatgttgat gaaggtagcc   1680

tctactgata aattgccttt aaagaaaatg attactcaca ggtttgagtt agctgaaatc   1740

gaacacgcat atcaggtttt cttgaatggc gctaaagaaa aagctatgaa gattattcta   1800

tctaatgcag gtgccgccta attaattaag agtaagcgaa tttcttatga tttatgattt   1860

ttattattaa ataagttata aaaaaaataa gtgtatacaa attttaaagt gactcttagg   1920

ttttaaaacg aaaattctta ttcttgagta actctttcct gtaggtcagg ttgctttctc   1980

aggtatagca tgaggtcgct cttattgacc acacctctac cggcatgccg agcaaatgcc   2040

tgcaaatcgc tccccatttc acccaattgt agatatgcta actccagcaa tgagttgatg   2100

aatctcggtg tgtattttat gtcctcagag gacaacacct gtggt                   2145
```

<210> SEQ ID NO 80
<211> LENGTH: 4280
<212> TYPE: DNA
<213> ORGANISM: Artificial Sequence
<220> FEATURE:
<223> OTHER INFORMATION: vector

<400> SEQUENCE: 80

```
ggggatcctc tagagtcgac ctgcaggcat gcaagcttgg cgtaatcatg gtcatagctg     60
tttcctgtgt gaaattgtta tccgctcaca attccacaca acatacgagc cggaagcata    120
aagtgtaaag cctggggtgc ctaatgagtg agctaactca cattaattgc gttgcgctca    180
ctgcccgctt tccagtcggg aaacctgtcg tgccagctgc attaatgaat cggccaacgc    240
gcggggagag gcggtttgcg tattgggcgc tcttccgctt cctcgctcac tgactcgctg    300
cgctcggtcg ttcggctgcg gcgagcggta tcagctcact caaaggcggt aatacggtta    360
tccacagaat caggggataa cgcaggaaag aacatgtgag caaaaggcca gcaaaaggcc    420
aggaaccgta aaaaggccgc gttgctggcg tttttccata ggctccgccc ccctgacgag    480
catcacaaaa atcgacgctc aagtcagagg tggcgaaacc cgacaggact ataaagatac    540
caggcgtttc cccctggaag ctccctcgtg cgctctcctg ttccgaccct gccgcttacc    600
ggatacctgt ccgcctttct cccttcggga agcgtggcgc tttctcatag ctcacgctgt    660
aggtatctca gttcggtgta ggtcgttcgc tccaagctgg gctgtgtgca cgaacccccc    720
gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct tcggggcgaa aactctcaag gatcttaccg   1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040
ataagggcga cacggaaatg ttgaatactc atactcttcc tttttcaata ttattgaagc   2100
atttatcagg gttattgtct catgagcgga tacatatttg aatgtattta gaaaaataaa   2160
```

caaatagggg ttccgcgcac atttccccga aaagtgccac ctgacgtcta agaaaccatt 2220
attatcatga cattaaccta taaaaatagg cgtatcacga ggccctttcg tctcgcgcgt 2280
ttcggtgatg acggtgaaaa cctctgacac atgcagctcc cggagacggt cacagcttgt 2340
ctgtaagcgg atgccgggag cagacaagcc cgtcagggcg cgtcagcggg tgttggcggg 2400
tgtcggggct ggcttaacta tgcggcatca gagcagattg tactgagagt gcaccatatg 2460
cggtgtgaaa taccgcacag atgcgtaagg agaaaatacc gcatcaggcg ccattcgcca 2520
ttcaggctgc gcaactgttg ggaagggcga tcggtgcggg cctcttcgct attacgccag 2580
ctggcgaaag ggggatgtgc tgcaaggcga ttaagttggg taacgccagg gttttcccag 2640
tcacgacgtt gtaaaacgac ggccagtgaa ttcgagctcg gtacccccgg ctctgagaca 2700
gtagtaggtt agtcatcgct ctaccgacgc gcaggaaaag aaagaagcat tgcggattac 2760
gtattctaat gttcagcccg cggaacgcca gcaaatcacc acccatgcgc atgatactga 2820
gtcttgtaca cgctgggctt ccagtgtact gagagtgcac cataccacag cttttcaatt 2880
caattcatca tttttttttt attctttttt ttgatttcgg tttctttgaa atttttttga 2940
ttcggtaatc tccgaacaga aggaagaacg aaggaaggag cacagactta gattggtata 3000
tatacgcata tgtagtgttg aagaaacatg aaattgccca gtattcttaa cccaactgca 3060
cagaacaaaa acctgcagga aacgaagata aatcatgtcg aaagctacat ataaggaacg 3120
tgctgctact catcctagtc ctgttgctgc caagctattt aatatcatgc acgaaaagca 3180
aacaaacttg tgtgcttcat tggatgttcg taccaccaag gaattactgg agttagttga 3240
agcattaggt cccaaaattt gtttactaaa aacacatgtg gatatcttga ctgatttttc 3300
catggagggc acagttaagc cgctaaaggc attatccgcc aagtacaatt ttttactctt 3360
cgaagacaga aaatttgctg acattggtaa tacagtcaaa ttgcagtact ctgcgggtgt 3420
atacagaata gcagaatggg cagacattac gaatgcacac ggtgtggtgg gcccaggtat 3480
tgttagcggt ttgaagcagg cggcagaaga agtaacaaag gaacctagag gccttttgat 3540
gttagcagaa ttgtcatgca agggctccct atctactgga gaatatacta agggtactgt 3600
tgacattgcg aagagcgaca aagattttgt tatcggcttt attgctcaaa gagacatggg 3660
tggaagagat gaaggttacg attggttgat tatgacaccc ggtgtgggtt tagatgacaa 3720
gggagacgca ttgggtcaac agtatagaac cgtggatgat gtggtctcta caggatctga 3780
cattattatt gttggaagag gactatttgc aaagggaagg gatgctaagg tagagggtga 3840
acgttacaga aaagcaggct gggaagcata tttgagaaga tgcggccagc aaaactaaaa 3900
aactgtatta taagtaaatg catgtatact aaactcacaa attagagctt caatttaatt 3960
atatcagtta ttaccctatg cggtgtgaaa taccgcacag atgcgtaagg agaaaatacc 4020
gcatcaggaa attgtaaacg ttaatatttt gttaaaattc gcgttaaatt tttgttaaat 4080
cagctcattt tttaaccaat aggccgaaat cggcaaaatc ttcagcccgc ggaacgccag 4140
caaatcacca cccatgcgca tgatactgag tcttgtacac gctgggcttc cagtgatgat 4200
acaacgagtt agccaaggtg agcacggatg tctaaattag aattacgttt taatatcttt 4260
ttttccatat ctagggctag 4280

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
gcatgcttgc atttagtcgt gcaatgtatg 30

<210> SEQ ID NO 82
<211> LENGTH: 54
<212> TYPE: DNA
<213> ORGANISM: Artificial Sequence
<220> FEATURE:
<223> OTHER INFORMATION: primer

<400> SEQUENCE: 82
gaacattaga atacgtaatc cgcaatgcac tagtaccaca ggtgttgtcc tctg 54

<210> SEQ ID NO 83
<211> LENGTH: 54
<212> TYPE: DNA
<213> ORGANISM: Artificial Sequence
<220> FEATURE:
<223> OTHER INFORMATION: primer

<400> SEQUENCE: 83
cagaggacaa cacctgtggt actagtgcat tgcggattac gtattctaat gttc 54

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
caccttggct aactcgttgt atcatcac 28

<210> SEQ ID NO 85
<211> LENGTH: 100
<212> TYPE: DNA
<213> ORGANISM: Artificial Sequence
<220> FEATURE:
<223> OTHER INFORMATION: primer

<400> SEQUENCE: 85
ttttaagccg aatgagtgac agaaaaagcc cacaacttat caagtgatat tgaacaaagg 60
gcgaaacttc gcatgcttgc atttagtcgt gcaatgtatg 100

<210> SEQ ID NO 86
<211> LENGTH: 98
<212> TYPE: DNA
<213> ORGANISM: Artificial Sequence
<220> FEATURE:
<223> OTHER INFORMATION: primer

<400> SEQUENCE: 86
cccaattggt aaatattcaa caagagacgc gcagtacgta acatgcgaat tgcgtaattc 60
acggcgataa caccttggct aactcgttgt atcatcac 98

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
caaaagccca tgtcccacac caaaggatg 29

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
caccatcgcg cgtgcatcac tgcatg 26

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
tcggtttttg caatatgacc tgtgggcc 28

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
gagaagatgc ggccagcaaa ac 22

<210> SEQ ID NO 91
<211> LENGTH: 2745
<212> TYPE: DNA
<213> ORGANISM: Artificial Sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480
gacggcaaag atatcgattt agtctctgtc tttgaaggtg tcggccattg gaaccacggc 540
gatatgacca aagaagaagt taaagctttg gaatgtaatg cttgtcccgg tcctggaggc 600
tgcggtggta tgtatactgc taacacaatg gcgacagcta ttgaagtttt gggacttagc 660
cttccgggtt catcttctca cccggctgaa tccgcagaaa agaaagcaga tattgaagaa 720
gctggtcgcg ctgttgtcaa aatgctcgaa atgggcttaa aaccttctga cattttaacg 780
cgtgaagctt ttgaagatgc tattactgta actatggctc tgggaggttc aaccaactca 840
acccttcacc tcttagctat tgcccatgct gctaatgtgg aattgacact tgatgatttc 900
aatactttcc aagaaaaagt tcctcatttg gctgatttga aaccttctgg tcaatatgta 960
ttccaagacc tttacaaggt cggaggggta ccagcagtta tgaaatatct ccttaaaaat 1020

```
ggcttccttc atggtgaccg tatcacttgt actggcaaaa cagtcgctga aaatttgaag   1080

gcttttgatg atttaacacc tggtcaaaag gttattatgc cgcttgaaaa tcctaaacgt   1140

gaagatggtc cgctcattat tctccatggt aacttggctc cagacggtgc cgttgccaaa   1200

gtttctggtg taaaagtgcg tcgtcatgtc ggtcctgcta aggtctttaa ttctgaagaa   1260

gaagccattg aagctgtctt gaatgatgat attgttgatg gtgatgttgt tgtcgtacgt   1320

tttgtaggac caaagggcgg tcctggtatg cctgaaatgc tttccctttc atcaatgatt   1380

gttggtaaag ggcaaggtga aaaagttgcc cttctgacag atggccgctt ctcaggtggt   1440

acttatggtc ttgtcgtggg tcatatcgct cctgaagcac aagatggcgg tccaatcgcc   1500

tacctgcaaa caggagacat agtcactatt gaccaagaca ctaaggaatt acactttgat   1560

atctccgatg aagagttaaa acatcgtcaa gagaccattg aattgccacc gctctattca   1620

cgcggtatcc ttggtaaata tgctcacatc gtttcgtctg cttctagggg agccgtaaca   1680

gacttttgga agcctgaaga aactggcaaa aaatgttgtc ctggttgctg tggttaagcg   1740

gccgcgttaa ttcaaattaa ttgatatagt tttttaatga gtattgaatc tgtttagaaa   1800

taatggaata ttatttttat ttatttattt atattattgg tcggctcttt tcttctgaag   1860

gtcaatgaca aaatgatatg aaggaaataa tgatttctaa aattttacaa cgtaagatat   1920

ttttacaaaa gcctagctca tcttttgtca tgcactattt tactcacgct tgaaattaac   1980

ggccagtcca ctgcggagtc atttcaaagt catcctaatc gatctatcgt ttttgatagc   2040

tcattttgga gttcgcgatt gtcttctgtt attcacaact gttttaattt ttatttcatt   2100

ctggaactct tcgagttctt tgtaaagtct ttcatagtag cttactttat cctccaacat   2160

atttaacttc atgtcaattt cggctcttaa attttccaca tcatcaagtt caacatcatc   2220

ttttaacttg aatttattct ctagctcttc caaccaagcc tcattgctcc ttgatttact   2280

ggtgaaaagt gatacacttt gcgcgcaatc caggtcaaaa ctttcctgca aagaattcac   2340

caatttctcg acatcatagt acaatttgtt ttgttctccc atcacaattt aatatacctg   2400

atggattctt atgaagcgct gggtaatgga cgtgtcactc tacttcgcct tttccctac    2460

tcctttagt acggaagaca atgctaataa ataagagggt aataataata ttattaatcg    2520

gcaaaaaaga ttaaacgcca agcgtttaat tatcagaaag caaacgtcgt accaatcctt   2580

gaatgcttcc caattgtata ttaagagtca tcacagcaac atattcttgt tattaaatta   2640

attattattg atttttgata ttgtataaaa aaaccaaata tgtataaaaa aagtgaataa   2700

aaaataccaa gtatggagaa atatattaga agtctatacg ttaaa                   2745
```

<210> SEQ ID NO 92
<211> LENGTH: 27
<212> TYPE: DNA
<213> ORGANISM: Artificial Sequence
<220> FEATURE:
<223> OTHER INFORMATION: primer

<400> SEQUENCE: 92

```
gacttttgga agcctgaaga aactggc                                         27
```

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
cttggcagca acaggactag 20

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ccaggccaat tcaacagact gtcggc 26

<210> SEQ ID NO 95
<211> LENGTH: 2347
<212> TYPE: DNA
<213> ORGANISM: Artificial Sequence
<220> FEATURE:
<223> OTHER INFORMATION: constructed URA3 marker with flanking homologous repeat sequences for HIS gene replacement and marker excision

<400> SEQUENCE: 95
gcattgcgga ttacgtattc taatgttcag gtgctggaag aagagctgct taaccgccgc 60
gcccagggtg aagatccacg ctactttacc ctgcgtcgtc tggatttcgg cggctgtcgt 120
ctttcgctgg caacgccggt tgatgaagcc tgggacggtc cgctctcctt aaacggtaaa 180
cgtatcgcca cctcttatcc tcacctgctc aagcgttatc tcgaccagaa aggcatctct 240
tttaaatcct gcttactgaa cggttctgtt gaagtcgccc cgcgtgccgg actggcggat 300
gcgatttgcg atctggtttc caccggtgcc acgctggaag ctaacggcct gcgcgaagtc 360
gaagttatct atcgctcgaa agcctgcctg attcaacgcg atggcgaaat ggaagaatcc 420
aaacagcaac tgatcgacaa actgctgacc cgtattcagg gtgtgatcca ggcgcgcgaa 480
tcaaaataca tcatgatgca cgcaccgacc gaacgtctgg atgaagtcat ggtacctact 540
gagagtgcac cataccacag cttttcaatt caattcatca tttttttttt attctttttt 600
ttgatttcgg tttctttgaa atttttttga ttcggtaatc tccgaacaga aggaagaacg 660
aaggaaggag cacagactta gattggtata tatacgcata tgtagtgttg aagaaacatg 720
aaattgccca gtattcttaa cccaactgca cagaacaaaa acctgcagga aacgaagata 780
aatcatgtcg aaagctacat ataaggaacg tgctgctact catcctagtc ctgttgctgc 840
caagctattt aatatcatgc acgaaaagca aacaaacttg tgtgcttcat tggatgttcg 900
taccaccaag gaattactgg agttagttga agcattaggt cccaaaattt gtttactaaa 960
aacacatgtg gatatcttga ctgatttttc catggagggc acagttaagc cgctaaaggc 1020
attatccgcc aagtacaatt ttttactctt cgaagacaga aaatttgctg acattggtaa 1080
tacagtcaaa ttgcagtact ctgcgggtgt atacagaata gcagaatggg cagacattac 1140
gaatgcacac ggtgtggtgg gcccaggtat tgttagcggt ttgaagcagg cggcagaaga 1200
agtaacaaag gaacctagag gccttttgat gttagcagaa ttgtcatgca agggctccct 1260
atctactgga gaatatacta agggtactgt tgacattgcg aagagcgaca aagattttgt 1320
tatcggcttt attgctcaaa gagacatggg tggaagagat gaaggttacg attggttgat 1380
tatgacaccc ggtgtgggtt tagatgacaa gggagacgca ttgggtcaac agtatagaac 1440
cgtggatgat gtggtctcta caggatctga cattattatt gttggaagag gactatttgc 1500
aaagggaagg gatgctaagg tagagggtga acgttacaga aaagcaggct gggaagcata 1560
tttgagaaga tgcggccagc aaaactaaaa aactgtatta taagtaaatg catgtatact 1620

```
aaactcacaa attagagctt caatttaatt atatcagtta ttaccctatg cggtgtgaaa   1680

taccgcacag atgcgtaagg agaaaatacc gcatcaggaa attgtaaacg ttaatatttt   1740

gttaaaattc gcgttaaatt tttgttaaat cagctcattt tttaaccaat aggccgaaat   1800

cggcaaaatc tctagagtgc tggaagaaga gctgcttaac cgccgcgccc agggtgaaga   1860

tccacgctac tttaccctgc gtcgtctgga tttcggcggc tgtcgtcttt cgctggcaac   1920

gccggttgat gaagcctggg acggtccgct ctccttaaac ggtaaacgta tcgccacctc   1980

ttatcctcac ctgctcaagc gttatctcga ccagaaaggc atctctttta aatcctgctt   2040

actgaacggt tctgttgaag tcgccccgcg tgccggactg gcggatgcga tttgcgatct   2100

ggtttccacc ggtgccacgc tggaagctaa cggcctgcgc gaagtcgaag ttatctatcg   2160

ctcgaaagcc tgcctgattc aacgcgatgg cgaaatggaa gaatccaaac agcaactgat   2220

cgacaaactg ctgacccgta ttcagggtgt gatccaggcg cgcgaatcaa aatacatcat   2280

gatgcacgca ccgaccgaac gtctggatga agtcatccag tgatgataca acgagttagc   2340

caaggtg                                                             2347
```

<210> SEQ ID NO 96
<211> LENGTH: 80
<212> TYPE: DNA
<213> ORGANISM: Artificial Sequence
<220> FEATURE:
<223> OTHER INFORMATION: primer

<400> SEQUENCE: 96

```
cttcgaagaa tatactaaaa aatgagcagg caagataaac gaaggcaaag gcattgcgga     60

ttacgtattc taatgttcag                                                 80
```

<210> SEQ ID NO 97
<211> LENGTH: 81
<212> TYPE: DNA
<213> ORGANISM: Artificial Sequence
<220> FEATURE:
<223> OTHER INFORMATION: primer

<400> SEQUENCE: 97

```
tatacacatg tatatatatc gtatgctgca gctttaaata atcggtgtca caccttggct     60

aactcgttgt atcatcactg g                                               81
```

<210> SEQ ID NO 98
<211> LENGTH: 26
<212> TYPE: DNA
<213> ORGANISM: Artificial Sequence
<220> FEATURE:
<223> OTHER INFORMATION: primer

<400> SEQUENCE: 98

```
gacttgaata atgcagcggc gcttgc                                          26
```

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99

```
ccaccctctt caattagcta agatcatagc                                      30
```

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
aaaaattgat tctcatcgta aatgc 25

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
ctgcagcgag gagccgtaat 20

<210> SEQ ID NO 102
<211> LENGTH: 90
<212> TYPE: DNA
<213> ORGANISM: Artificial Sequence
<220> FEATURE:
<223> OTHER INFORMATION: primer

<400> SEQUENCE: 102
atggttcatt taggtccaaa aaaaccacaa gccagaaagg gttccatggc cgatgtgcca 60
gcattgcgga ttacgtattc taatgttcag 90

<210> SEQ ID NO 103
<211> LENGTH: 91
<212> TYPE: DNA
<213> ORGANISM: Artificial Sequence
<220> FEATURE:
<223> OTHER INFORMATION: primer

<400> SEQUENCE: 103
ttaagcaccg atgataccaa cggacttacc ttcagcaatt ctttttttggg ccaaagcagc 60 caccttggct aactcgttgt atcatcactg g 91

<210> SEQ ID NO 104
<211> LENGTH: 24
<212> TYPE: DNA
<213> ORGANISM: Artificial Sequence
<220> FEATURE:
<223> OTHER INFORMATION: primer

<400> SEQUENCE: 104
ctaggatgag tagcagcacg ttcc 24

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ccaattccgt gatgtctctt tgttgc 26

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gtgaacgagt tcacaaccgc 20

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
gttcgttcca gaattatcac gc 22

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
ggatccgcat gcttgcattt agtcgtgc 28

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gggatgcgga cgtattcggc 20

<210> SEQ ID NO 110
<211> LENGTH: 4506
<212> TYPE: DNA
<213> ORGANISM: Saccharomyces cerevisiae

<400> SEQUENCE: 110
atgtcgaata ccccttataa ttcatctgtg ccttccattg catccatgac ccagtcttcg 60
gtctcaagaa gtcctaacat gcatacagca actacgcccg gtgccaacac cagctctaac 120
tctccaccct tgcacatgtc ttcagattcg tccaagatca agaggaagcg taacagaatt 180
ccgctcagtt gcaccatttg tcggaaaagg aaagtcaaat gtgacaaact cagaccacac 240
tgccagcagt gcactaaaac tggggtagcc catctctgcc actacatgga acagacctgg 300
gcagaagagg cagagaaaga attgctgaag gacaacgaat taaagaagct tagggagcgc 360
gtaaaatctt tagaaaagac tctttctaag gtgcactctt ctccttcgtc taactccttg 420
aaaagttaca acactcccga gagcagcaac ctgtttatgg gtagcgatga acacaccacc 480
cttgttaatg caaatacagg ctctgcttcc tctgcctcgc atatgcatca gcaacaacag 540
caacagcagc aacaggaaca acaacaagac ttttccagaa gtgcgaacgc caacgcgaat 600
tcctcgtccc tttctatctc aaataaatat gacaacgatg agctggactt aactaaggac 660
tttgatcttt tgcatatcaa aagtaacgga accatccact taggtgccac ccactggttg 720
tctatcatga aaggtgaccc gtacctaaaa cttttgtggg gtcatatctt cgctatgagg 780
gaaaagttaa atgaatggta ctaccaaaaa aattcgtact ctaagctgaa gtcaagcaaa 840
tgtcccatca atcacgcgca agcgccgcct tctgccgctg ccgccgctac cagaaaatgt 900

```
cctgttgatc actccgcgtt ttcgtctggc atggtggccc caaaggagga gactcctctt    960
cctaggaaat gtccagttga ccacaccatg ttctcttcgg gaatgattcc tcccagagag   1020
gacacttcgt cccagaagag gtgtcccgtt gaccacacca tgtattccgc aggaatgatg   1080
ccgcccaagg acgagacacc ttccccattt tccactaaag ctatgataga ccataacaag   1140
catacaatga atccgcctca gtcaaaatgt cctgtggacc atagaaacta tatgaaggat   1200
tatccctctg acatggcaaa ttcttcttcg aacccggcaa gtcgttgccc cattgaccat   1260
tcaagcatga aaaatacagc ggccttacca gcttcaacgc acaataccat cccacaccac   1320
caaccacagt ccggatctca tgctcgttcg catcccgcac aaagcaggaa acatgattcc   1380
tacatgacag aatctgaagt cctcgcaaca ctttgtgaga tgttgccacc aaagcgcgtc   1440
atcgcattat tcatcgagaa attcttcaaa catttatacc ctgccattcc aatcttagat   1500
gaacagaatt tcaaaaatca cgtgaatcaa atgctttcgt tgtcttcgat gaatcccaca   1560
gttaacaact ttggtatgag catgccatct tcatctacac tagagaacca acccataaca   1620
caaatcaatc ttccaaaact ttccgattct tgtaacttag gtattctgat aataatcttg   1680
agattgacat ggctatccat accttctaat tcctgcgaag tcgacctggg agaagaaagt   1740
ggctcatttt tagtgcccaa cgaatctagc aatatgtctg catctgcatt gacctcgatg   1800
gctaaagaag aatcacttct gctaaagcat gagacaccgg tcgaggcact ggagctatgt   1860
caaaaatact tgattaaatt cgatgaactt tctagtattt ccaataacaa cgttaattta   1920
accacggtgc agtttgccat tttttacaac ttctatatga aaagtgcctc taatgatttg   1980
actaccttga caaataccaa caacactggc atggccaatc ctggtcacga ttccgagtct   2040
caccagatcc tattgtccaa tattactcaa atggccttta gttgtgggtt acacagagac   2100
cctgataatt ttcctcaatt aaacgctacc attccagcaa ccagccagga cgtgtctaac   2160
aacgggagca aaaaggcaaa ccctagcacc aatccaactt tgaataacaa catgtctgct   2220
gccactacca acagcagtag cagatctggc agtgctgatt caagaagtgg ttctaaccct   2280
gtgaacaaga aggaaaatca ggttagtatc gaaagattta aacacacttg gaggaaaatt   2340
tggtattaca ttgttagcat ggatgttaac caatctcttt ccctggggag ccctcgacta   2400
ctaagaaatc tgagggattt cagcgataca aagctaccaa gtgcgtcaag gattgattat   2460
gttcgcgata tcaaagagtt aatcattgtg aagaatttta ctcttttttt ccaaattgat   2520
ttgtgtatta ttgctgtatt aaatcacatt ttgaatgttt ctttagcaag aagcgtgaga   2580
aaatttgaac tggattcatt gattaattta ttgaaaaatc tgacctatgg tactgagaat   2640
gtcaatgatg tagtgagctc cttgatcaac aaagggttat taccaacttc ggaaggtggt   2700
tctgtagatt caaataatga tgaaatttac ggtctaccga aactacccga tattctaaac   2760
catggtcaac ataaccaaaa cttgtatgct gatggaagaa atacttctag tagtgatata   2820
gataagaaat tggaccttcc tcacgaatct acaacgagag ctctattctt ttccaagcat   2880
atgacaatta gaatgttgct gtacttattg aactacattt tgtttactca ttatgaacca   2940
atgggcagtg aagatcctgg tactaatatc ctagctaagg agtacgctca agaggcatta   3000
aattttgcca tggatggcta cagaaactgc atgattttct tcaacaatat cagaaacacc   3060
aattcactat tcgattacat gaatgttatc ttgtcttacc cttgtttgga cattggacat   3120
cgttctttac aatttatcgt ttgtttgatc ctgagagcta aatgtggccc attgactggt   3180
atgcgtgaat catcgatcat tactaatggt acatcaagtg gatttaatag ttcggtagaa   3240
gatgaggacg tcaaagttaa acaagaatct tctgatgaat tgaaaaaaga cgatttcatg   3300
```

```
aaagatgtaa atttggattc aggcgattca ttagcagaga ttctaatgtc aagaatgctg   3360

ctatttcaaa aactaacaaa acaactatca aagaagtaca actacgctat tcgtatgaac   3420

aaatccactg gattctttgt ctctttacta gatacacctt caaagaaatc agactcgaaa   3480

tcgggtggta gttcattcat gttgggtaat tggaaacatc caaaggtttc aaacatgagc   3540

ggatttcttg ctggtgacaa agaccaatta cagaaatgcc ccgtgtacca agatgcgctg   3600

gggtttgtta gtccaaccgg tgctaatgaa ggttctgctc cgatgcaagg catgtcctta   3660

cagggctcta ctgctaggat gggagggacc cagttgccac caattagatc atacaaacct   3720

atcacgtaca caagtagtaa tctacgtcgt atgaatgaaa cgggtgaggc agaagctaag   3780

agaagaagat ttaatgatgg ctatattgat aataatagta acaacgatat acctagagga   3840

atcagcccaa aaccttcaaa tgggctatca tcggtgcagc cactattatc gtcattttcc   3900

atgaaccagc taaacggggg taccattcca acggttccat cgttaaccaa cattacttca   3960

caaatgggag ctttaccatc tttagatagg atcaccacta atcaaataaa tttgccagac   4020

ccatctagag atgaagcatt tgacaactcc atcaagcaaa tgacgcctat gacaagtgca   4080

ttcatgaatg ctaatactac aattccaagt tcaactttaa acgggaatat gaacatgaat   4140

ggagctggaa ctgcgaatac agatacaagt gccaacggca gtgctttatc gacactgaca   4200

agcccacaag gctcagactt agcatccaat tctgctacac agtataaacc tgacttagaa   4260

gactttttga tgcaaaattc taactttaat gggctaatga taaatccttc cagtctggta   4320

gaagttgttg gtggatacaa cgatcctaat aaccttggaa gaaatgacgc ggttgatttt   4380

ctacccgttg ataatgttga aattgatggt gttggaataa aaatcaacta tcatctacta   4440

actagtattt acgttactag tatattatca tatacggtgt tagaagatga cgcaaatgat   4500

gagaaa                                                              4506
```

<210> SEQ ID NO 111
<211> LENGTH: 99
<212> TYPE: DNA
<213> ORGANISM: Artificial Sequence
<220> FEATURE:
<223> OTHER INFORMATION: primer

<400> SEQUENCE: 111

```
tcctttctca attattattt tctactcata acctcacgca aaataacaca gtcaaatcaa     60

tcaaagtatg actgacaaaa aaactcttaa agacttaag                            99
```

<210> SEQ ID NO 112
<211> LENGTH: 77
<212> TYPE: DNA
<213> ORGANISM: Artificial Sequence
<220> FEATURE:
<223> OTHER INFORMATION: primer

<400> SEQUENCE: 112

```
gaacattaga atacgtaatc cgcaatgctt ctttcttttc cgtttaacgt atagacttct     60

aatatatttc tccatac                                                    77
```

<210> SEQ ID NO 113
<211> LENGTH: 45
<212> TYPE: DNA
<213> ORGANISM: Artificial Sequence
<220> FEATURE:
<223> OTHER INFORMATION: primer

<400> SEQUENCE: 113
aaacggaaaa gaaagaagca ttgcggatta cgtattctaa tgttc 45

<210> SEQ ID NO 114
<211> LENGTH: 88
<212> TYPE: DNA
<213> ORGANISM: Artificial Sequence
<220> FEATURE:
<223> OTHER INFORMATION: primer

<400> SEQUENCE: 114
tatttttcgt tacataaaaa tgcttataaa actttaacta ataattagag attaaatcgc 60
caccttggct aactcgttgt atcatcac 88

<210> SEQ ID NO 115
<211> LENGTH: 1713
<212> TYPE: DNA
<213> ORGANISM: Streptococcus mutans

<400> SEQUENCE: 115
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480
gacggcaaag atatcgattt agtctctgtc tttgaaggtg tcggccattg gaaccacggc 540
gatatgacca aagaagaagt taaagctttg gaatgtaatg cttgtcccgg tcctggaggc 600
tgcggtggta tgtatactgc taacacaatg gcgacagcta ttgaagtttt gggacttagc 660
cttccgggtt catcttctca cccggctgaa tccgcagaaa agaaagcaga tattgaagaa 720
gctggtcgcg ctgttgtcaa aatgctcgaa atgggcttaa aaccttctga cattttaacg 780
cgtgaagctt ttgaagatgc tattactgta actatggctc tgggaggttc aaccaactca 840
acccttcacc tcttagctat tgcccatgct gctaatgtgg aattgacact tgatgatttc 900
aatactttcc aagaaaaagt tcctcatttg gctgatttga aaccttctgg tcaatatgta 960
ttccaagacc tttacaaggt cggaggggta ccagcagtta tgaaatatct ccttaaaaat 1020
ggcttccttc atggtgaccg tatcacttgt actggcaaaa cagtcgctga aaatttgaag 1080
gcttttgatg atttaacacc tggtcaaaag gttattatgc cgcttgaaaa tcctaaacgt 1140
gaagatggtc cgctcattat tctccatggt aacttggctc cagacggtgc cgttgccaaa 1200
gtttctggtg taaaagtgcg tcgtcatgtc ggtcctgcta aggtctttaa ttctgaagaa 1260
gaagccattg aagctgtctt gaatgatgat attgttgatg gtgatgttgt tgtcgtacgt 1320
tttgtaggac caaagggcgg tcctggtatg cctgaaatgc tttccctttc atcaatgatt 1380
gttggtaaag ggcaaggtga aaaagttgcc cttctgacag atggccgctt ctcaggtggt 1440
acttatggtc ttgtcgtggg tcatatcgct cctgaagcac aagatggcgg tccaatcgcc 1500
tacctgcaaa caggagacat agtcactatt gaccaagaca ctaaggaatt acactttgat 1560
atctccgatg aagagttaaa acatcgtcaa gagaccattg aattgccacc gctctattca 1620
cgcggtatcc ttggtaaata tgctcacatc gtttcgtctg cttctagggg agccgtaaca 1680

```
gacttttgga agcctgaaga aactggcaaa aaa                              1713


<210> SEQ ID NO 116
<211> LENGTH: 571
<212> TYPE: PRT
<213> ORGANISM: Streptococcus mutans

<400> SEQUENCE: 116

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365
```

```
Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570


<210> SEQ ID NO 117
<211> LENGTH: 548
<212> TYPE: PRT
<213> ORGANISM: Lactococcus lactis

<400> SEQUENCE: 117

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175
```

```
Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 118
<211> LENGTH: 1125
<212> TYPE: DNA
<213> ORGANISM: Artificial Sequence
<220> FEATURE:
<223> OTHER INFORMATION: horse ADH coding region codon optimized for S. cerevisiae expression

<400> SEQUENCE: 118

```
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg ttcgtcctgg tgataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
ttccttggta cttctacatt ttcccaatac acagtggtgg acgagatatc tgtcgctaaa     480
atcgatgcag cttcaccact ggaaaaagtt tgcttgatag ggtgcggatt ttccaccggt     540
tacggttccg cagttaaagt tgcaaaggtt acacagggtt cgacttgtgc agtattcggt     600
ttaggaggag taggactaag cgttattatg ggtgtaaaag ctgcaggcgc agcgaggatt     660
ataggtgtag acatcaataa ggacaaattt gcaaaagcta aggaggtcgg ggctactgaa     720
tgtgttaacc ctcaagatta taagaaacca atacaagaag tccttactga aatgtcaaac     780
ggtggagttg atttctcttt tgaagttata ggccgtcttg atactatggt aactgcgttg     840
tcctgctgtc aagaggcata tggagtcagt gtgatcgtag gtgttcctcc tgattcacaa     900
aatttgtcga tgaatcctat gctgttgcta agcggtcgta catggaaggg agctatattt     960
ggcggtttta agagcaagga tagtgttcca aaacttgttg ccgactttat ggcgaagaag    1020
tttgctcttg atcctttaat tacacatgta ttgccattcg agaaaatcaa tgaagggttt    1080
gatttgttaa gaagtggtga atctattcgt acaattttaa ctttt                    1125
```

<210> SEQ ID NO 119
<211> LENGTH: 375
<212> TYPE: PRT
<213> ORGANISM: Equus caballus

<400> SEQUENCE: 119

```
Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
```

```
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375
```

<210> SEQ ID NO 120
<211> LENGTH: 643
<212> TYPE: DNA
<213> ORGANISM: Saccharomyces cerevisiae

<400> SEQUENCE: 120

```
gaaatgaata acaatactga cagtactaaa taattgccta cttggcttca catacgttgc     60

atacgtcgat atagataata atgataatga cagcaggatt atcgtaatac gtaatagttg    120

aaaatctcaa aaatgtgtgg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360

tctgttctct tctgactttg actcctcaaa aaaaaaaaat ctacaatcaa cagatcgctt    420

caattacgcc ctcacaaaaa ctttttttcct tcttcttcgc ccacgttaaa ttttatccct    480

catgttgtct aacggatttc tgcacttgat ttattataaa aagacaaaga cataatactt    540

ctctatcaat ttcagttatt gttcttcctt gcgttattct tctgttcttc tttttctttt    600

gtcatatata accataacca agtaatacat attcaaatct aga                      643
```

<210> SEQ ID NO 121
<211> LENGTH: 9089
<212> TYPE: DNA
<213> ORGANISM: Artificial Sequence
<220> FEATURE:
<223> OTHER INFORMATION: constructed plasmid

<400> SEQUENCE: 121

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggcccccct cgaggtcgac tggccattaa   2040
tctttcccat attagatttc gccaagccat gaaagttcaa gaaaggtctt tagacgaatt   2100
acccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
```

```
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttc atgtagatga   2640
tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
caagaacaat gcaatagcgc atcaagaaaa aacacaaagc tttcaatcaa tgaatcgaaa   2940
atgtcattaa aatagtatat aaattgaaac taagtcataa agctataaaa agaaaattta   3000
tttaaatgca agatttaaag taaattcacg gccctgcagg ccctaacctg ctaggacaca   3060
acgtctttgc ctggtaaagt ttctagctga cgtgattcct tcacctgtgg atccggcaat   3120
tgtaaaggtt gtgaaaccct cagcttcata accgacacct gcaaatgact ttgcattctt   3180
aacaaagata gttgtatcaa tttcacgttc gaatctatta aggttatcga tgttcttaga   3240
ataaatgtag gcggaatgtt ttctattctg ctcagctatc ttggcgtatt taatggcttc   3300
atcaatgtcc ttcactctaa ctataggcaa aattggcatc atcaactccg tcataacgaa   3360
cggatggttt gcgttgactt cacaaataat acactttaca ttacttggtg actctacatc   3420
tatttcatcc aaaaacagtt tagcgtcctt accaacccac ttcttattaa tgaaatattc   3480
ttgagtttca ttgttctttt gaagaacaag gtctatcagc ttggatactt ggtcttcatt   3540
gataatgacg gcgttgtttt tcaacatgtt agagatcaga tcatctgcaa cgttttcaaa   3600
cacgaacact tctttttccg cgatacaagg aagattgttg tcaaacgaac aaccttcaat   3660
aatgcttctg ccggccttct cgatatctgc tgtatcgtct acaataaccg gaggattacc   3720
cgcgccagct ccgatggcct tttaccaga attaagaagg gtttttacca tacccgggcc   3780
acccgtaccg cacaacaatt ttatggatgg atgtttgata atagcgtcta aactttccat   3840
agttgggttc tttatagtag tgacaaggtt ttcaggtcca ccacagctaa ttatggcttt   3900
gtttatcatt tctactgcga aagcgacaca ctttttggcg catgggtgac cattaaatac   3960
aactgcattc cccgcagcta tcatacctat agaattgcag ataacggttt ctgttggatt   4020
cgtgcttgga gttatagcgc cgataactcc gtatggactc atttcaacca ctgttagtcc   4080
attatcgccg gaccatgctg ttgttgtcag atcttcagtg cctggggtat acttggccac   4140
taattcatgt ttcaagattt tatcctcata ccttcccatg tgggtttcct ccaggatcat   4200
tgtggctaag acctctttat tctgtaatgc ggcttttctt atttcggtga ttattttctc   4260
tctttgttcc tttgtgtagt gtagggaaag aatcttttgt gcatgtactg cagaagaaat   4320
ggcattctca acattttcaa atactccaaa acatgaagag ttatctttgt aattctttaa   4380
gttgatgttt tcaccattag tcttcacttt caagtctttg gtggttggga ttaaggtatc   4440
tttatccatg gtgtttgttt atgtgtgttt attcgaaact aagttcttgg tgttttaaaa   4500
ctaaaaaaaa gactaactat aaaagtagaa tttaagaagt ttaagaaata gatttacaga   4560
attacaatca atacctaccg tctttatata cttattagtc aagtagggga ataatttcag   4620
ggaactggtt tcaacctttt ttttcagctt tttccaaatc agagagagca gaaggtaata   4680
gaaggtgtaa gaaaatgaga tagatacatg cgtgggtcaa ttgccttgtg tcatcattta   4740
ctccaggcag gttgcatcac tccattgagg ttgtgcccgt tttttgcctg tttgtgcccc   4800
```

```
tgttctctgt agttgcgcta agagaatgga cctatgaact gatggttggt gaagaaaaca   4860
atattttggt gctgggattc ttttttttc tggatgccag cttaaaaagc gggctccatt   4920
atatttagtg gatgccagga ataaactgtt cacccagaca cctacgatgt tatatattct   4980
gtgtaacccg ccccctattt tgggcatgta cgggttacag cagaattaaa aggctaattt   5040
tttgactaaa taaagttagg aaaatcacta ctattaatta tttacgtatt ctttgaaatg   5100
gcagtattga taatgataaa ctcgaactga aaaagcgtgt tttttattca aaatgattct   5160
aactccctta cgtaatcaag gaatcttttt gccttggcct ccgcgtcatt aaacttcttg   5220
ttgttgacgc taacattcaa cgctagtata tattcgtttt tttcaggtaa gttcttttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat   5400
ttaaatcttg gctctcttgg gctcaaggtg acaaggtcct cgaaaatagg gcgcgcccca   5460
ccgcggtgga gctccagctt ttgttccctt tagtgagggt taattgcgcg cttggcgtaa   5520
tcatggtcat agctgtttcc tgtgtgaaat tgttatccgc tcacaattcc acacaacata   5580
ggagccggaa gcataaagtg taaagcctgg ggtgcctaat gagtgaggta actcacatta   5640
attgcgttgc gctcactgcc cgctttccag tcgggaaacc tgtcgtgcca gctgcattaa   5700
tgaatcggcc aacgcgcggg gagaggcggt ttgcgtattg ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaaagaacat gtgagcaaaa   5880
ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac cccccgttca gcccgaccgc tgcgccttat ccggtaacta tcgtcttgag   6240
tccaacccgg taagacacga cttatcgcca ctggcagcag ccactggtaa caggattagc   6300
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gagattatca   6600
aaaaggatct tcacctagat ccttttaaat taaaaatgaa gttttaaatc aatctaaagt   6660
atatatgagt aaacttggtc tgacagttac caatgcttaa tcagtgaggc acctatctca   6720
gcgatctgtc tatttcgttc atccatagtt gcctgactcc ccgtcgtgta gataactacg   6780
atacgggagg gcttaccatc tggccccagt gctgcaatga taccgcgaga cccacgctca   6840
ccggctccag atttatcagc aataaaccag ccagccggaa gggccgagcg cagaagtggt   6900
cctgcaactt tatccgcctc catccagtct attaattgtt gccgggaagc tagagtaagt   6960
agttcgccag ttaatagttt gcgcaacgtt gttgccattg ctacaggcat cgtggtgtca   7020
cgctcgtcgt ttggtatggc ttcattcagc tccggttccc aacgatcaag gcgagttaca   7080
tgatccccca tgttgtgcaa aaaagcggtt agctccttcg gtcctccgat cgttgtcaga   7140
agtaagttgg ccgcagtgtt atcactcatg gttatggcag cactgcataa ttctcttact   7200
```

```
gtcatgccat ccgtaagatg cttttctgtg actggtgagt actcaaccaa gtcattctga   7260
gaatagtgta tgcggcgacc gagttgctct tgcccggcgt caatacggga taataccgcg   7320
ccacatagca gaactttaaa agtgctcatc attggaaaac gttcttcggg gcgaaaactc   7380
tcaaggatct taccgctgtt gagatccagt tcgatgtaac ccactcgtgc acccaactga   7440
tcttcagcat cttttacttt caccagcgtt tctgggtgag caaaaacagg aaggcaaaat   7500
gccgcaaaaa agggaataag ggcgacacgg aaatgttgaa tactcatact cttccttttt   7560
caatattatt gaagcattta tcagggttat tgtctcatga gcggatacat atttgaatgt   7620
atttagaaaa ataaacaaat aggggttccg cgcacatttc cccgaaaagt gccacctgaa   7680
cgaagcatct gtgcttcatt ttgtagaaca aaaatgcaac gcgagagcgc taatttttca   7740
aacaaagaat ctgagctgca tttttacaga acagaaatgc aacgcgaaag cgctatttta   7800
ccaacgaaga atctgtgctt catttttgta aaacaaaaat gcaacgcgag agcgctaatt   7860
tttcaaacaa agaatctgag ctgcattttt acagaacaga aatgcaacgc gagagcgcta   7920
ttttaccaac aaagaatcta tacttctttt ttgttctaca aaaatgcatc ccgagagcgc   7980
tatttttcta acaaagcatc ttagattact ttttttctcc tttgtgcgct ctataatgca   8040
gtctcttgat aactttttgc actgtaggtc cgttaaggtt agaagaaggc tactttggtg   8100
tctattttct cttccataaa aaaagcctga ctccacttcc cgcgtttact gattactagc   8160
gaagctgcgg gtgcattttt tcaagataaa ggcatccccg attatattct ataccgatgt   8220
ggattgcgca tactttgtga acagaaagtg atagcgttga tgattcttca ttggtcagaa   8280
aattatgaac ggtttcttct attttgtctc tatatactac gtataggaaa tgtttacatt   8340
ttcgtattgt tttcgattca ctctatgaat agttcttact acaatttttt tgtctaaaga   8400
gtaatactag agataaacat aaaaaatgta gaggtcgagt ttagatgcaa gttcaaggag   8460
cgaaaggtgg atgggtaggt tatataggga tatagcacag agatatatag caaagagata   8520
cttttgagca atgtttgtgg aagcggtatt cgcaatattt tagtagctcg ttacagtccg   8580
gtgcgttttt ggtttttga aagtgcgtct tcagagcgct tttggttttc aaaagcgctc   8640
tgaagttcct atactttcta gagaatagga acttcggaat aggaacttca aagcgtttcc   8700
gaaaacgagc gcttccgaaa atgcaacgcg agctgcgcac atacagctca ctgttcacgt   8760
cgcacctata tctgcgtgtt gcctgtatat atatatacat gagaagaacg gcatagtgcg   8820
tgtttatgct taaatgcgta cttatatgcg tctatttatg taggatgaaa ggtagtctag   8880
tacctcctgt gatattatcc cattccatgc ggggtatcgt atgcttcctt cagcactacc   8940
ctttagctgt tctatatgct gccactcctc aattggatta gtctcatcct tcaatgctat   9000
catttccttt gatattggat catactaaga aaccattatt atcatgacat taacctataa   9060
aaataggcgt atcacgaggc cctttcgtc                                     9089
```

```
<210> SEQ ID NO 122
<211> LENGTH: 1023
<212> TYPE: DNA
<213> ORGANISM: Saccharomyces cerevisiae

<400> SEQUENCE: 122

caccgcggtg gggcgcgccc tattttcgag gaccttgtca ccttgagccc aagagagcca     60
agatttaaat tttcctatga cttgatgcaa attcccaaag ctaataacat gcaagacacg    120
tacggtcaag aagacatatt tgacctctta acaggttcag acgcgactgc ctcatcagta    180
agacccgttg aaaagaactt acctgaaaaa aacgaatata tactagcgtt gaatgttagc    240
```

gtcaacaaca agaagtttaa tgacgcggag gccaaggcaa aaagattcct tgattacgta 300
agggagttag aatcattttg aataaaaaac acgctttttc agttcgagtt tatcattatc 360
aatactgcca tttcaaagaa tacgtaaata attaatagta gtgattttcc taactttatt 420
tagtcaaaaa attagccttt taattctgct gtaacccgta catgcccaaa atagggggcg 480
ggttacacag aatatataac atcgtaggtg tctgggtgaa cagtttattc ctggcatcca 540
ctaaatataa tggagcccgc tttttaagct ggcatccaga aaaaaaaaga atcccagcac 600
caaaatattg ttttcttcac caaccatcag ttcataggtc cattctctta gcgcaactac 660
agagaacagg ggcacaaaca ggcaaaaaac gggcacaacc tcaatggagt gatgcaacct 720
gcctggagta aatgatgaca caaggcaatt gacccacgca tgtatctatc tcattttctt 780
acaccttcta ttaccttctg ctctctctga tttggaaaaa gctgaaaaaa aaggttgaaa 840
ccagttccct gaaattattc ccctacttga ctaataagta tataaagacg gtaggtattg 900
attgtaattc tgtaaatcta tttcttaaac ttcttaaatt ctacttttat agttagtctt 960 tttttagtt ttaaaacacc aagaacttag tttcgaataa acacacataa actagtaaac 1020
aaa 1023

<210> SEQ ID NO 123
<211> LENGTH: 21
<212> TYPE: DNA
<213> ORGANISM: Artificial Sequence
<220> FEATURE:
<223> OTHER INFORMATION: primer

<400> SEQUENCE: 123
caaaagctga gctccaccgc g 21

<210> SEQ ID NO 124
<211> LENGTH: 44
<212> TYPE: DNA
<213> ORGANISM: Artificial Sequence
<220> FEATURE:
<223> OTHER INFORMATION: primer

<400> SEQUENCE: 124
gtttactagt ttatgtgtgt ttattcgaaa ctaagttctt ggtg 44

<210> SEQ ID NO 125

<400> SEQUENCE: 125

000

<210> SEQ ID NO 126
<211> LENGTH: 39
<212> TYPE: DNA
<213> ORGANISM: Artificial Sequence
<220> FEATURE:
<223> OTHER INFORMATION: primer

<400> SEQUENCE: 126
cacacatatt acaatagcta gctgaggatg aaagctctg 39

<210> SEQ ID NO 127
<211> LENGTH: 39
<212> TYPE: DNA
<213> ORGANISM: Artificial Sequence
<220> FEATURE:
<223> OTHER INFORMATION: primer

<400> SEQUENCE: 127
cagagctttc atcctcagct agctattgta atatgtgtg 39

<210> SEQ ID NO 128
<211> LENGTH: 9491
<212> TYPE: DNA
<213> ORGANISM: Artificial Sequence
<220> FEATURE:
<223> OTHER INFORMATION: constructed plasmid

<400> SEQUENCE: 128
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat attttttat gcctcggtaa tgattttcat 360
tttttttttt ccccctagcgg atgactcttt tttttcttta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgat acatgctctg gccaagcatt 720
ccggctggtc gctaatcgtt gagtgcattg gtgacttaca catagacgac catcacacca 780
ctgaagactg cgggattgct ctcggtcaag cttttaaaga ggccctactg gcgcgtggag 840
taaaaaggtt tggatcagga tttgcgcctt tggatgaggc actttccaga gcggtggtag 900
atctttcgaa caggccgtac gcagttgtcg aacttggttt gcaaagggag aaagtaggag 960
atctctcttg cgagatgatc ccgcattttc ttgaaagctt tgcagaggct agcagaatta 1020
ccctccacgt tgattgtctg cgaggcaaga atgatcatca ccgtagtgag agtgcgttca 1080
aggctcttgc ggttgccata agagaagcca cctcgcccaa tggtaccaac gatgttccct 1140
ccaccaaagg tgttcttatg tagtgacacc gattatttaa agctgcagca tacgatatat 1200
atacatgtgt atatatgtat acctatgaat gtcagtaagt atgtatacga acagtatgat 1260
actgaagatg acaaggtaat gcatcattct atacgtgtca ttctgaacga ggcgcgcttt 1320 cctttttttct ttttgctttt tcttttttttt tctcttgaac tcgacggatc tatgcggtgt 1380
gaaataccgc acagatgcgt aaggagaaaa taccgcatca ggaaattgta aacgttaata 1440
ttttgttaaa attcgcgtta aatttttgtt aaatcagctc attttttaac caataggccg 1500
aaatcggcaa aatcccttat aaatcaaaag aatagaccga gatagggttg agtgttgttc 1560
cagtttggaa caagagtcca ctattaaaga acgtggactc caacgtcaaa gggcgaaaaa 1620
ccgtctatca gggcgatggc ccactacgtg aaccatcacc ctaatcaagt tttttggggt 1680
cgaggtgccg taaagcacta aatcggaacc ctaaagggag cccccgattt agagcttgac 1740
ggggaaagcc ggcgaacgtg gcgagaaagg aagggaagaa agcgaaagga gcgggcgcta 1800
gggcgctggc aagtgtagcg gtcacgctgc gcgtaaccac cacacccgcc gcgcttaatg 1860
cgccgctaca gggcgcgtcg cgccattcgc cattcaggct gcgcaactgt tgggaagggc 1920
gatcggtgcg ggcctcttcg ctattacgcc agctggcgaa aggggggatgt gctgcaaggc 1980

-continued

```
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggcgcgcc actggtagag agcgactttg tatgccccaa ttgcgaaacc cgcgatatcc   2160
ttctcgattc tttagtaccc gaccaggaca aggaaaagga ggtcgaaacg tttttgaaga   2220
aacaagagga actacacgga agctctaaag atggcaacca gccagaaact aagaaaatga   2280
agttgatgga tccaactggc accgctggct tgaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat gataggaatg   2640
ggattcttct atttttcctt tttccattct agcagccgtc gggaaaacgt ggcatcctct   2700
ctttcgggct caattggagt cacgctgccg tgagcatcct ctctttccat atctaacaac   2760
tgagcacgta accaatggaa aagcatgagc ttagcgttgc tccaaaaaag tattggatgg   2820
ttaataccat ttgtctgttc tcttctgact ttgactcctc aaaaaaaaaa aatctacaat   2880
caacagatcg cttcaattac gccctcacaa aaactttttt ccttcttctt cgcccacgtt   2940
aaattttatc cctcatgttg tctaacggat ttctgcactt gatttattat aaaaagacaa   3000
agacataata cttctctatc aatttcagtt attgttcttc cttgcgttat tcttctgttc   3060
ttcttttctt tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
tatcgtcggt gtcatttcaa cttgggctga aaacacacct tgtaatatcc acttacatga   3300
ctttggtaaa ctagccaaag tcggtgttaa ggaagctggt gcttggccag ttcagttcgg   3360
aacaatcacg gtttctgatg gaatcgccat gggaacccaa ggaatgcgtt tctccttgac   3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaaagaaa gcagatattg aagaagctgg   3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag ggtaccagc agttatgaaa tatctcctta aaaatggctt   4140
ccttcatggt gaccgtatca cttgtactgg caaaacagtc gctgaaaatt tgaaggcttt   4200
tgatgattta acacctggtc aaaaggttat tatgccgctt gaaaatccta aacgtgaaga   4260
tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
```

-continued

```
cattgaagct gtcttgaatg atgatattgt tgatggtgat gttgttgtcg tacgttttgt   4440
aggaccaaag ggcggtcctg gtatgcctga aatgctttcc ctttcatcaa tgattgttgg   4500
taaagggcaa ggtgaaaaag ttgcccttct gacagatggc cgcttctcag gtggtactta   4560
tggtcttgtc gtgggtcata tcgctcctga agcacaagat ggcggtccaa tcgcctacct   4620
gcaaacagga gacatagtca ctattgacca agacactaag gaattacact ttgatatctc   4680
cgatgaagag ttaaaacatc gtcaagagac cattgaattg ccaccgctct attcacgcgg   4740
tatccttggt aaatatgctc acatcgtttc gtctgcttct aggggagccg taacagactt   4800
ttggaagcct gaagaaactg gcaaaaaatg ttgtcctggt tgctgtggtt aagcggccgc   4860
gttaattcaa attaattgat atagtttttt aatgagtatt gaatctgttt agaaataatg   4920
gaatattatt tttatttatt tatttatatt attggtcggc tcttttcttc tgaaggtcaa   4980
tgacaaaatg atatgaagga aataatgatt tctaaaattt tacaacgtaa gatattttta   5040
caaaagccta gctcatcttt tgtcatgcac tattttactc acgcttgaaa ttaacggcca   5100
gtccactgcg gagtcatttc aaagtcatcc taatcgatct atcgtttttg atagctcatt   5160
ttggagttcg cgattgtctt ctgttattca caactgtttt aatttttatt tcattctgga   5220
actcttcgag ttctttgtaa agtctttcat agtagcttac tttatcctcc aacatattta   5280
acttcatgtc aatttcggct cttaaatttt ccacatcatc aagttcaaca tcatctttta   5340
acttgaattt attctctagc tcttccaacc aagcctcatt gctccttgat ttactggtga   5400
aaagtgatac actttgcgcg caatccaggt caaaactttc ctgcaaagaa ttcaccaatt   5460
tctcgacatc atagtacaat ttgttttgtt ctcccatcac aatttaatat acctgatgga   5520
ttcttatgaa gcgctgggta atggacgtgt cactctactt cgcctttttc cctactcctt   5580
ttagtacgga agacaatgct aataaataag agggtaataa taatattatt aatcggcaaa   5640
aaagattaaa cgccaagcgt ttaattatca gaaagcaaac gtcgtaccaa tccttgaatg   5700
cttcccaatt gtatattaag agtcatcaca gcaacatatt cttgttatta aattaattat   5760
tattgatttt tgatattgta taaaaaaacc aaatatgtat aaaaaaagtg aataaaaaat   5820
accaagtatg gagaaatata ttagaagtct atacgttaaa ccaccgcggt ggagctccag   5880
cttttgttcc ctttagtgag ggttaattgc gcgcttggcg taatcatggt catagctgtt   5940
tcctgtgtga aattgttatc cgctcacaat tccacacaac ataggagccg gaagcataaa   6000
gtgtaaagcc tggggtgcct aatgagtgag gtaactcaca ttaattgcgt tgcgctcact   6060
gcccgctttc cagtcgggaa acctgtcgtg ccagctgcat taatgaatcg gccaacgcgc   6120
ggggagaggc ggtttgcgta ttgggcgctc ttccgcttcc tcgctcactg actcgctgcg   6180
ctcggtcgtt cggctgcggc gagcggtatc agctcactca aaggcggtaa tacggttatc   6240
cacagaatca ggggataacg caggaaagaa catgtgagca aaaggccagc aaaaggccag   6300
gaaccgtaaa aaggccgcgt tgctggcgtt tttccatagg ctccgccccc ctgacgagca   6360
tcacaaaaat cgacgctcaa gtcagaggtg gcgaaacccg acaggactat aaagatacca   6420
ggcgtttccc cctggaagct ccctcgtgcg ctctcctgtt ccgaccctgc cgcttaccgg   6480
atacctgtcc gcctttctcc cttcgggaag cgtggcgctt tctcatagct cacgctgtag   6540
gtatctcagt tcggtgtagg tcgttcgctc caagctgggc tgtgtgcacg aaccccccgt   6600
tcagcccgac cgctgcgcct tatccggtaa ctatcgtctt gagtccaacc cggtaagaca   6660
cgacttatcg ccactggcag cagccactgg taacaggatt agcagagcga ggtatgtagg   6720
cggtgctaca gagttcttga agtggtggcc taactacggc tacactagaa ggacagtatt   6780
```

```
tggtatctgc gctctgctga agccagttac cttcggaaaa agagttggta gctcttgatc   6840
cggcaaacaa accaccgctg gtagcggtgg tttttttgtt tgcaagcagc agattacgcg   6900
cagaaaaaaa ggatctcaag aagatccttt gatcttttct acggggtctg acgctcagtg   6960
gaacgaaaac tcacgttaag ggattttggt catgagatta tcaaaaagga tcttcaccta   7020
gatcctttta aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc cagatttatc   7260
agcaataaac cagccagccg gaagggccga gcgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
ggcttcattc agctccggtt cccaacgatc aaggcgagtt acatgatccc ccatgttgtg   7500
caaaaaagcg gttagctcct tcggtcctcc gatcgttgtc agaagtaagt tggccgcagt   7560
gttatcactc atggttatgg cagcactgca taattctctt actgtcatgc catccgtaag   7620
atgcttttct gtgactggtg agtactcaac caagtcattc tgagaatagt gtatgcggcg   7680
accgagttgc tcttgcccgg cgtcaatacg ggataatacc gcgccacata gcagaacttt   7740
aaaagtgctc atcattggaa aacgttcttc ggggcgaaaa ctctcaagga tcttaccgct   7800
gttgagatcc agttcgatgt aacccactcg tgcacccaac tgatcttcag catcttttac   7860
tttcaccagc gtttctgggt gagcaaaaac aggaaggcaa aatgccgcaa aaaagggaat   7920
aagggcgaca cggaaatgtt gaatactcat actcttcctt tttcaatatt attgaagcat   7980
ttatcagggt tattgtctca tgagcggata catatttgaa tgtatttaga aaaataaaca   8040
aataggggtt ccgcgcacat ttccccgaaa agtgccacct gaacgaagca tctgtgcttc   8100
attttgtaga acaaaaatgc aacgcgagag cgctaatttt tcaaacaaag aatctgagct   8160
gcatttttac agaacagaaa tgcaacgcga aagcgctatt ttaccaacga agaatctgtg   8220
cttcattttt gtaaaacaaa aatgcaacgc gagagcgcta atttttcaaa caaagaatct   8280
gagctgcatt tttacagaac agaaatgcaa cgcgagagcg ctattttacc aacaaagaat   8340
ctatacttct tttttgttct acaaaaatgc atcccgagag cgctattttt ctaacaaagc   8400
atcttagatt actttttttc tcctttgtgc gctctataat gcagtctctt gataactttt   8460
tgcactgtag gtccgttaag gttagaagaa ggctactttg gtgtctattt tctcttccat   8520
aaaaaaagcc tgactccact tcccgcgttt actgattact agcgaagctg cgggtgcatt   8580
ttttcaagat aaaggcatcc ccgattatat tctataccga tgtggattgc gcatactttg   8640
tgaacagaaa gtgatagcgt tgatgattct tcattggtca gaaaattatg aacggtttct   8700
tctattttgt ctctatatac tacgtatagg aaatgtttac attttcgtat tgttttcgat   8760
tcactctatg aatagttctt actacaattt ttttgtctaa agagtaatac tagagataaa   8820
cataaaaaat gtagaggtcg agtttagatg caagttcaag gagcgaaagg tggatgggta   8880
ggttatatag ggatatagca cagagatata tagcaaagag atacttttga gcaatgtttg   8940
tggaagcggt attcgcaata ttttagtagc tcgttacagt ccggtgcgtt tttggttttt   9000
tgaaagtgcg tcttcagagc gcttttggtt ttcaaaagcg ctctgaagtt cctatacttt   9060
ctagagaata ggaacttcgg aataggaact tcaaagcgtt tccgaaaacg agcgcttccg   9120
aaaatgcaac gcgagctgcg cacatacagc tcactgttca cgtcgcacct atatctgcgt   9180
```

```
gttgcctgta tatatatata catgagaaga acggcatagt gcgtgtttat gcttaaatgc   9240

gtacttatat gcgtctattt atgtaggatg aaaggtagtc tagtacctcc tgtgatatta   9300

tcccattcca tgcggggtat cgtatgcttc cttcagcact accctttagc tgttctatat   9360

gctgccactc ctcaattgga ttagtctcat ccttcaatgc tatcatttcc tttgatattg   9420

gatcatctaa gaaaccatta ttatcatgac attaacctat aaaaataggc gtatcacgag   9480

gccctttcgt c                                                         9491
```

<210> SEQ ID NO 129
<211> LENGTH: 1000
<212> TYPE: DNA
<213> ORGANISM: Saccharomyces cerevisiae

<400> SEQUENCE: 129

```
gttaattcaa attaattgat atagtttttt aatgagtatt gaatctgttt agaaataatg     60

gaatattatt tttatttatt tatttatatt attggtcggc tcttttcttc tgaaggtcaa    120

tgacaaaatg atatgaagga aataatgatt tctaaaattt tacaacgtaa gatattttta    180

caaaagccta gctcatcttt tgtcatgcac tattttactc acgcttgaaa ttaacggcca    240

gtccactgcg gagtcatttc aaagtcatcc taatcgatct atcgtttttg atagctcatt    300

ttggagttcg cgattgtctt ctgttattca caactgtttt aatttttatt tcattctgga    360

actcttcgag ttctttgtaa agtctttcat agtagcttac tttatcctcc aacatattta    420

acttcatgtc aatttcggct cttaaatttt ccacatcatc aagttcaaca tcatctttta    480

acttgaattt attctctagc tcttccaacc aagcctcatt gctccttgat ttactggtga    540

aaagtgatac actttgcgcg caatccaggt caaaactttc ctgcaaagaa ttcaccaatt    600

tctcgacatc atagtacaat ttgttttgtt ctcccatcac aatttaatat acctgatgga    660

ttcttatgaa gcgctgggta atggacgtgt cactctactt cgcctttttc cctactcctt    720

ttagtacgga agacaatgct aataaataag agggtaataa taatattatt aatcggcaaa    780

aaagattaaa cgccaagcgt ttaattatca gaaagcaaac gtcgtaccaa tccttgaatg    840

cttcccaatt gtatattaag agtcatcaca gcaacatatt cttgttatta aattaattat    900

tattgatttt tgatattgta taaaaaaacc aaatatgtat aaaaaaagtg aataaaaaat    960

accaagtatg gagaaatata ttagaagtct atacgttaaa                         1000
```

<210> SEQ ID NO 130
<211> LENGTH: 16387
<212> TYPE: DNA
<213> ORGANISM: Artificial Sequence
<220> FEATURE:
<223> OTHER INFORMATION: Plasmid

<400> SEQUENCE: 130

```
gatcctctag tttctcggta ctatgcatat gatccaatat caaaggaaat gatagcattg     60

aaggatgaga ctaatccaat tgaggagtgg cagcatatag aacagctaaa gggtagtgct    120

gaaggaagca tacgataccc cgcatggaat gggataatat cacaggaggt actagactac    180

ctttcatcct acataaatag acgcatataa gtacgcattt aagcataaac acgcactatg    240

ccgttcttct catgtatata tatatacagg caacacgcag atataggtgc gacgtgaaca    300

gtgagctgta tgtgcgcagc tcgcgttgca ttttcggaag cgctcgtttt cggaaacgct    360

ttgaagttcc tattccgaag ttcctattct ctagaaagta taggaacttc agagcgcttt    420

tgaaaaccaa aagcgctctg aagacgcact ttcaaaaaac caaaaacgca ccggactgta    480
```

```
acgagctact aaaatattgc gaataccgct tccacaaaca ttgctcaaaa gtatctcttt    540
gctatatatc tctgtgctat atccctatat aacctaccca tccacctttc gctccttgaa    600
cttgcatcta aactcgacct ctacattttt tatgtttatc tctagtatta ctctttagac    660
aaaaaaattg tagtaagaac tattcataga gtgaatcgaa aacaatacga aaatgtaaac    720
atttcctata cgtagtatat agagacaaaa tagaagaaac cgttcataat tttctgacca    780
atgaagaatc atcaacgcta tcactttctg ttcacaaagt atgcgcaatc cacatcggta    840
tagaatataa tcggggatgc ctttatcttg aaaaaatgca cccgcagctt cgctagtaat    900
cagtaaacgc gggaagtgga gtcaggcttt ttttatggaa gagaaaatag acaccaaagt    960
agccttcttc taaccttaac ggacctacag tgcaaaaagt tatcaagaga ctgcattata   1020
gagcgcacaa aggagaaaaa aagtaatcta agatgctttg ttagaaaaat agcgctctcg   1080
ggatgcattt ttgtagaaca aaaaagaagt atagattctt tgttggtaaa atagcgctct   1140
cgcgttgcat ttctgttctg taaaaatgca gctcagattc tttgtttgaa aaattagcgc   1200
tctcgcgttg catttttgtt ttacaaaaat gaagcacaga ttcttcgttg gtaaaatagc   1260
gctttcgcgt tgcatttctg ttctgtaaaa atgcagctca gattctttgt ttgaaaaatt   1320
agcgctctcg cgttgcattt ttgttctaca aaatgaagca cagatgcttc gttaacaaag   1380
atatgctatt gaagtgcaag atggaaacgc agaaaatgaa ccggggatgc gacgtgcaag   1440
attacctatg caatagatgc aatagtttct ccaggaaccg aaatacatac attgtcttcc   1500
gtaaagcgct agactatata ttattataca ggttcaaata tactatctgt ttcagggaaa   1560
actcccaggt tcggatgttc aaaattcaat gatgggtaac aagtacgatc gtaaatctgt   1620
aaaacagttt gtcggatatt aggctgtatc tcctcaaagc gtattcgaat atcattgaga   1680
agctgcattt tttttttttt tttttttttt ttttttata tatatttcaa ggatatacca    1740
ttgtaatgtc tgcccctaag aagatcgtcg ttttgccagg tgaccacgtt ggtcaagaaa   1800
tcacagccga agccattaag gttcttaaag ctatttctga tgttcgttcc aatgtcaagt   1860
tcgatttcga aaatcattta attggtggtg ctgctatcga tgctacaggt gttccacttc   1920
cagatgaggc gctggaagcc tccaagaagg ctgatgccgt tttgttaggt gctgtgggtg   1980
gtcctaaatg gggtaccggt agtgttagac ctgaacaagg tttactaaaa atccgtaaag   2040
aacttcaatt gtacgccaac ttaagaccat gtaactttgc atccgactct cttttagact   2100
tatctccaat caagccacaa tttgctaaag gtactgactt cgttgttgtt agagaattag   2160
tgggaggtat ttactttggt aagagaaagg aagacgatgg tgatggtgtc gcttgggata   2220
gtgaacaata caccgttcca gaagtgcaaa gaatcacaag aatggccgct ttcatggccc   2280
tacaacatga gccaccattg cctatttggt ccttggataa agctaatgtt ttggcctctt   2340
caagattatg gagaaaaact gtggaggaaa ccatcaagaa cgaattccct acattgaaag   2400
ttcaacatca attgattgat tctgccgcca tgatcctagt taagaaccca acccacctaa   2460
atggtattat aatcaccagc aacatgtttg gtgatatcat ctccgatgaa gcctccgtta   2520
tcccaggctc cttgggtttg ttgccatctg cgtccttggc ctctttgcca gacaagaaca   2580
ccgcatttgg tttgtacgaa ccatgccatg gttccgctcc agatttgcca aagaataagg   2640
tcaaccctat cgccactatc ttgtctgctg caatgatgtt gaaattgtca ttgaacttgc   2700
ctgaagaagg taaagccatt gaagatgcag ttaaaaaggt tttggatgca ggtatcagaa   2760
ctggtgattt aggtggttcc aacagtacca ccgaagtcgg tgatgctgtc gccgaagaag   2820
ttaagaaaat ccttgcttaa aaagattctc ttttttatg atatttgtac aaaaaaaaaa    2880
```

-continued

```
aaaaaaaaaa aaaaaaaaaa aaaaaaaaaa aaaaaaaaaa aatgcagcgt cacatcggat   2940
aataatgatg gcagccattg tagaagtgcc ttttgcattt ctagtctctt tctcggtcta   3000
gctagtttta ctacatcgcg aagatagaat cttagatcac actgcctttg ctgagctgga   3060
tcaatagagt aacaaaagag tggtaaggcc tcgttaaagg acaaggacct gagcggaagt   3120
gtatcgtaca gtagacggag tatactagag tcgacctgca ggcatgcaag cttttcaatt   3180
catcattttt tttttattct ttttttgat ttcggtttcc ttgaaatttt tttgattcgg    3240
taatctccga acagaaggaa gaacgaagga aggagcacag acttagattg gtatatatac   3300
gcatatgtag tgttgaagaa acatgaaatt gcccagtatt cttaacccaa ctgcacagaa   3360
caaaaacctg caggaaacga agataaatca tgtcgaaagc tacatataag gaacgtgctg   3420
ctactcatcc tagtcctgtt gctgccaagc tatttaatat catgcacgaa aagcaaacaa   3480
acttgtgtgc ttcattggat gttcgtacca ccaaggaatt actggagtta gttgaagcat   3540
taggtcccaa aatttgttta ctaaaaacac atgtggatat cttgactgat ttttccatgg   3600
agggcacagt taagccgcta aaggcattat ccgccaagta caatttttta ctcttcgaag   3660
acagaaaatt tgctgacatt ggtaatacag tcaaattgca gtactctgcg ggtgtataca   3720
gaatagcaga atgggcagac attacgaatg cacacggtgt ggtgggccca ggtattgtta   3780
gcggtttgaa gcaggcggca gaagaagtaa caaaggaacc tagaggcctt ttgatgttag   3840
cagaattgtc atgcaagggc tccctatcta ctggagaata tactaagggt actgttgaca   3900
ttgcgaagag cgacaaagat tttgttatcg gctttattgc tcaaagagac atgggtggaa   3960
gagatgaagg ttacgattgg ttgattatga cacccggtgt gggtttagat gacaagggag   4020
acgcattggg tcaacagtat agaaccgtgg atgatgtggt ctctacagga tctgacatta   4080
ttattgttgg aagaggacta tttgcaaagg gaagggatgc taaggtagag ggtgaacgtt   4140
acagaaaagc aggctgggaa gcatatttga gaagatgcgg ccagcaaaac taaaaaactg   4200
tattataagt aaatgcatgt atactaaact cacaaattag agcttcaatt taattatatc   4260
agttattacc cgggaatctc ggtcgtaatg atttttataa tgacgaaaaa aaaaaaattg   4320
gaaagaaaaa gcttggcgta atcatggtca tagctgtttc ctgtgtgaaa ttgttatccg   4380
ctcacaattc cacacaacat acgagccgga agcataaagt gtaaagcctg gggtgcctaa   4440
tgagtgagct aactcacatt aattgcgttg cgctcactgc ccgctttcca gtcgggaaac   4500
ctgtcgtgcc agctgcatta atgaatcggc caacgcgcgg ggagaggcgg tttgcgtatt   4560
gggcgctctt ccgcttcctc gctcactgac tcgctgcgct cggtcgttcg gctgcggcga   4620
gcggtatcag ctcactcaaa ggcggtaata cggttatcca cagaatcagg ggataacgca   4680
ggaaagaaca tgtgagcaaa aggccagcaa aaggccagga accgtaaaaa ggccgcgttg   4740
ctggcgtttt tccataggct ccgcccccct gacgagcatc acaaaaatcg acgctcaagt   4800
cagaggtggc gaaacccgac aggactataa agataccagg cgtttccccc tggaagctcc   4860
ctcgtgcgct ctcctgttcc gaccctgccg cttaccggat acctgtccgc ctttctccct   4920
tcgggaagcg tggcgctttc tcatagctca cgctgtaggt atctcagttc ggtgtaggtc   4980
gttcgctcca agctgggctg tgtgcacgaa ccccccgttc agcccgaccg ctgcgcctta   5040
tccggtaact atcgtcttga gtccaacccg gtaagacacg acttatcgcc actggcagca   5100
gccactggta acaggattag cagagcgagg tatgtaggcg gtgctacaga gttcttgaag   5160
tggtggccta actacggcta cactagaaga acagtatttg gtatctgcgc tctgctgaag   5220
ccagttacct tcggaaaaag agttggtagc tcttgatccg gcaaacaaac caccgctggt   5280
```

```
agcggtggtt tttttgtttg caagcagcag attacgcgca gaaaaaaagg atctcaagaa   5340

gatcctttga tcttttctac ggggtctgac gctcagtgga acgaaaactc acgttaaggg   5400

attttggtca tgagattatc aaaaaggatc ttcacctaga tccttttaaa ttaaaaatga   5460

agttttaaat caatctaaag tatatatgag taaacttggt ctgacagtta ccaatgctta   5520

atcagtgagg cacctatctc agcgatctgt ctatttcgtt catccatagt tgcctgactc   5580

cccgtcgtgt agataactac gatacgggag ggcttaccat ctggccccag tgctgcaatg   5640

ataccgcgag acccacgctc accggctcca gatttatcag caataaacca gccagccgga   5700

agggccgagc gcagaagtgg tcctgcaact ttatccgcct ccatccagtc tattaattgt   5760

tgccgggaag ctagagtaag tagttcgcca gttaatagtt tgcgcaacgt tgttgccatt   5820

gctacaggca tcgtggtgtc acgctcgtcg tttggtatgg cttcattcag ctccggttcc   5880

caacgatcaa ggcgagttac atgatccccc atgttgtgca aaaaagcggt tagctccttc   5940

ggtcctccga tcgttgtcag aagtaagttg gccgcagtgt tatcactcat ggttatggca   6000

gcactgcata attctcttac tgtcatgcca tccgtaagat gcttttctgt gactggtgag   6060

tactcaacca agtcattctg agaatagtgt atgcggcgac cgagttgctc ttgcccggcg   6120

tcaatacggg ataataccgc gccacatagc agaactttaa aagtgctcat cattggaaaa   6180

cgttcttcgg ggcgaaaact ctcaaggatc ttaccgctgt tgagatccag ttcgatgtaa   6240

cccactcgtg cacccaactg atcttcagca tcttttactt tcaccagcgt ttctgggtga   6300

gcaaaaacag gaaggcaaaa tgccgcaaaa aagggaataa gggcgacacg gaaatgttga   6360

atactcatac tcttcctttt tcaatattat tgaagcattt atcagggtta ttgtctcatg   6420

agcggataca tatttgaatg tatttagaaa aataaacaaa taggggttcc gcgcacattt   6480

ccccgaaaag tgccacctga cgtctaagaa accattatta tcatgacatt aacctataaa   6540

aataggcgta tcacgaggcc ctttcgtctc gcgcgtttcg gtgatgacgg tgaaaacctc   6600

tgacacatgc agctcccgga gacggtcaca gcttgtctgt aagcggatgc cgggagcaga   6660

caagcccgtc agggcgcgtc agcgggtgtt ggcgggtgtc ggggctggct taactatgcg   6720

gcatcagagc agattgtact gagagtgcac cataaaattg taaacgttaa tattttgtta   6780

aaattcgcgt taaatttttg ttaaatcagc tcatttttta accaatagac cgaaatcggc   6840

aaaatccctt ataaatcaaa agaatagccc gagatagagt tgagtgttgt tccagtttgg   6900

aacaagagtc cactattaaa gaacgtggac tccaacgtca aagggcgaaa aaccgtctat   6960

cagggcgatg gcccactacg tgaaccatca cccaaatcaa gtttttttggg gtcgaggtgc   7020

cgtaaagcac taaatcggaa ccctaaaggg agcccccgat ttagagcttg acggggaaag   7080

ccggcgaacg tggcgagaaa ggaagggaag aaagcgaaag gagcgggcgc taaggcgctg   7140

gcaagtgtag cggtcacgct gcgcgtaacc accacacccg ccgcgcttaa tgcgccgcta   7200

cagggcgcgt actatggttg ctttgacgta tgcggtgtga aataccgcac agatgcgtaa   7260

ggagaaaata ccgcatcagg cgccattcgc cattcaggct gcgcaactgt tgggaagggc   7320

gatcggtgcg ggcctcttcg ctattacgcc agctggcgaa agggggatgt gctgcaaggc   7380

gattaagttg ggtaacgcca gggttttccc agtcacgacg ttgtaaaacg acggccagtg   7440

aattcgagct ccaccgcgga tagatctgaa atgaataaca atactgacag tactaaataa   7500

ttgcctactt ggcttcacat acgttgcata cgtcgatata gataataatg ataatgacag   7560

caggattatc gtaatacgta atagttgaaa atctcaaaaa tgtgtgggtc attacgtaaa   7620

taatgatagg aatgggattc ttctattttt cctttttcca ttctagcagc cgtcgggaaa   7680
```

```
acgtggcatc ctctctttcg ggctcaattg gagtcacgct gccgtgagca tcctctcttt   7740
ccatatctaa caactgagca cgtaaccaat ggaaaagcat gagcttagcg ttgctccaaa   7800
aaagtattgg atggttaata ccatttgtct gttctcttct gactttgact cctcaaaaaa   7860
aaaaaatcta caatcaacag atcgcttcaa ttacgccctc acaaaaactt ttttccttct   7920
tcttcgccca cgttaaattt tatccctcat gttgtctaac ggatttctgc acttgattta   7980
ttataaaaag acaaagacat aatacttctc tatcaatttc agttattgtt cttccttgcg   8040
ttattcttct gttcttcttt ttcttttgtc atatataacc ataaccaagt aatacatatt   8100
caaatctaga gctgaggatg ttgaagcaaa tcaacttcgg tggtactgtt gaaaccgtct   8160
acgaaagagc tgactggcca agagaaaagt tgttggacta cttcaagaac gacacttttg   8220
ctttgatcgg ttacggttcc caaggttacg gtcaaggttt gaacttgaga gacaacggtt   8280
tgaacgttat cattggtgtc cgtaaagatg gtgcttcttg gaaggctgcc atcgaagacg   8340
gttgggttcc aggcaagaac ttgttcactg ttgaagatgc tatcaagaga ggtagttacg   8400
ttatgaactt gttgtccgat gccgctcaat cagaaacctg gcctgctatc aagccattgt   8460
tgaccaaggg taagactttg tacttctccc acggtttctc cccagtcttc aaggacttga   8520
ctcacgttga accaccaaag gacttagatg ttatcttggt tgctccaaag ggttccggta   8580
gaactgtcag atctttgttc aaggaaggtc gtggtattaa ctcttcttac gccgtctgga   8640
acgatgtcac cggtaaggct cacgaaaagg cccaagcttt ggccgttgcc attggttccg   8700
gttacgttta ccaaaccact ttcgaaagag aagtcaactc tgacttgtac ggtgaaagag   8760
gttgtttaat gggtggtatc cacggtatgt tcttggctca atacgacgtc ttgagagaaa   8820
acggtcactc cccatctgaa gctttcaacg aaaccgtcga agaagctacc caatctctat   8880
acccattgat cggtaagtac ggtatggatt acatgtacga tgcttgttcc accaccgcca   8940
gaagaggtgc tttggactgg tacccaatct tcaagaatgc tttgaagcct gttttccaag   9000
acttgtacga atctaccaag aacggtaccg aaaccaagag atctttggaa ttcaactctc   9060
aacctgacta cagagaaaag ctagaaaagg aattagacac catcagaaac atggaaatct   9120
ggaaggttgg taaggaagtc agaaagttga gaccagaaaa ccaataatta attaatcatg   9180
taattagtta tgtcacgctt acattcacgc cctcccccca catccgctct aaccgaaaag   9240
gaaggagtta gacaacctga agtctaggtc cctatttatt tttttatagt tatgttagta   9300
ttaagaacgt tatttatatt tcaaattttt cttttttttc tgtacagacg cgtgtacgca   9360
tgtaacatta tactgaaaac cttgcttgag aaggttttgg gacgctcgaa ggctttaatt   9420
tgcgggcggc cgctctagag agttgttagc aacctttgt ttcttttgag ctggttcaga   9480
cattatgtac acgtatatgt gacgagttcg agaagtattt tactatcgta ctaaatttta   9540
cctgaaaaat tatatactcg agaaagagga agccaagaat tgagaaaaaa gaaaaacccg   9600
cgagtaagga aattaaatac aggtgtacac atacacgcac acatatatat atatatatat   9660
atgtatatgt gtatatagga agcgcgcgca tgttagtata tacgattcgt tggaaagggg   9720
ccgtccacca aacgtgactt gacgagttga caaattgacc tcaatatggc tcagtcagta   9780
atttttagtt ccgctttatt cccgccatct ttcaggccac gagggtagct cataacgccg   9840
cgctaatgcc gctgcgtcac agcaaccagt agctcagcca aaaccgaaag agaaatcgta   9900
gctgtcccga tgaggactta tacacttgtc accatctaaa taaattattt attcgcgttt   9960
cggttcttgt tttcgattta attagattgt tcattgaatc ataataaata tgtaaaaaat  10020
atatatattt gaagctgctt cagaaaaaca gggcttccta gtgtacagat gtatgtcgga  10080
```

-continued

```
tgaaaaaaaa aaaatcttaa atgtgaaatt gggtcaattc aattgactat gacttgatgt  10140
tgcaaaaatt ccaagagaaa aagtttccag cacttgatat tattttcctc tttaattttt  10200
cgccttgtct acgatcttat tagcaccgat ccagggcatc atagacctta actgttcacc  10260
aataatttcg ataccatgtg ctgcattgtt tcttctttta gcagtcatac tcgggtaacc  10320
cgtagcgcct tcacttatga acatcttagc gtattcaccg tcctggatac gtttcaaggc  10380
atttctcatg gcttgtcttg attctgcgtt aatgacttca ggtccggtga catactcacc  10440
atattctgca ttatttgaaa tggaatagtt catattagct ataccacctt catacattaa  10500
gtctactatc aacttcaatt catgtagaca ttcgaagtat gccatttcgg gagcgtaccc  10560
tgcttcgaca agcgtctcaa agcctgcttt aaccaattca acagttcctc cgcacagaac  10620
cgcttgttct ccaaataaat ctgtctcagt ctcgtcttta aaagtggttt ctattatacc  10680
cgttctcccg ccaccaactc ctgctgcgta gcttaaagct acattcttag cgtttccgct  10740
tgcgtcttgg tatatagcga tcaaatctgg aataccacca cccttaacaa attcgctcct  10800
aacagtatgc cccggagcct taggtgcaat cataataacg tccaaatctg ccctggggac  10860
tacttgattg taatgaatgg caaatccatg actgaaggcc aaggtagcgc ccttcttaat  10920
gtttggttct atttcatttt tgtacaattg cgattgaaat tcatctggcg ttaaaatcat  10980
gactaaatca gcgccggcaa cagccgctgc aacatctgtg actttcaagc catgtgcttc  11040
agcctttgca acggtagcac taccttttct cagacctact gtcacgtcga ccccagaatc  11100
tttcaagtta caggcttgtg cgtgtccttg ggaaccatat cctataatag caaccttctt  11160
tccctggatg atgctcagat cgcagtcttt atcgtaaaac accttcatgt tttatttttt  11220
acttatattg ctggtagggt aaaaaaatat aactcctagg aataggttgt ctatatgttt  11280
ttgtcttgct tctataattg taacaaacaa ggaaagggaa aatactgggt gtaaaagcca  11340
ttgagtcaag ttaggtcatc ccttttatac aaaatttttc aattttttt ccaagattct  11400
tgtacgatta attattttt ttttgcgtcc tacagcgtga tgaaaatttc cgcctgctgc  11460
aagatgagcg ggaacgggcg aaatgtgcac gcgcacaact tacgaaacgc ggatgagtca  11520
ctgacagcca ccgcagaggt tctgactcct actgagctct attggaggtg gcagaaccgg  11580
taccggagga gaccgctata accggtttga atttattgtc acagtgtcac atcagcggca  11640
actcagaagt ttgacagcaa gcaagttcat cattcgaact agccttattg ttttagttca  11700
gtgacagcga actgccgtac tcgatgcttt atttctcacg gtagagcgga agaacagata  11760
ggggcagcgt gagaagagtt agaaagtaaa tttttatcac gtctgaagta ttcttattca  11820
taggaaattt tgcaaggttt tttagctcaa taacgggcta agttatataa ggtgttcacg  11880
cgattttctt gttatgtata cctcttctct gaggaatggt actactgtcc tgatgtaggc  11940
tccttaaatt ggtgggcaag aataacttat cgatattttg tatattggtc ttggagttca  12000
ccacgtaatg cctgtttaag accatcagtt aactctagta ttatttggtc ttggctactg  12060
gccgtttgct attattcaag tcttttgtgc cttcccgtcg ggtaagggag ttatttaggg  12120
atacagaatc taacgaaaac taaatctcaa tgattaactc catttaatcc ttttttgaaa  12180
ggcaaaagag gtcccttgtt cacttacaac gttcttagcc aaattcgctt atcacttact  12240
acttcacgat atacagaagt aaaaacatat aaaaagatgt ctgtttgttt agccatcaca  12300
aaaggtatcg cagtttcttc tataggcctc tactctggtc ttttggcttc cgcttcattg  12360
attacatcta ctactccact agaggtttta acaggatctc taaaaacatc gatatcgtct  12420
ctgcgttcca atcctacggt gaatatattt ccaagcaatt cactgaagaa gaaagagaag  12480
```

```
atgttgtgga acatgcatgc ccaggtcctg gttcttgtgg tggtatgtat actgccaaca  12540
caatggcttc tgccgctgaa gtgctaggtt tgaccattcc aaactcctct tccttcccag  12600
ccgtttccaa ggagaagtta gctgagtgtg acaacattgg tgaatacatc aagaagacaa  12660
tggaattggg tattttacct cgtgatatcc tcacaaaaga ggcttttgaa aacgccatta  12720
cttatgtcgt tgcaaccggt gggtccacta atgctgtttt gcatttggtg gctgttgctc  12780
actctgcggg tgtcaagttg tcaccagatg atttccaaag aatcagtgat actacaccat  12840
tgatcggtga cttcaaacct tctggtaaat acgtcatggc cgatttgatt aacgttggtg  12900
gtacccaatc tgtgattaag tatctatatg aaaacaacat gttgcacggt aacacaatga  12960
ctgttaccgg tgacactttg gcagaacgtg caaagaaagc accaagccta cctgaaggac  13020
aagagattat taagccactc tcccacccaa tcaaggccaa cggtcacttg caaattctgt  13080
acggttcatt ggcaccaggt ggagctgtgg gtaaaattac cggtaaggaa ggtacttact  13140
tcaagggtag agcacgtgtg ttcgaagagg aaggtgcctt tattgaagcc ttggaaagag  13200
gtgaaatcaa gaagggtgaa aaaaccgttg ttgttatcag atatgaaggt ccaagaggtg  13260
caccaggtat gcctgaaatg ctaaagcctt cctctgctct gatgggttac ggtttgggta  13320
aagatgttgc attgttgact gatggtagat tctctggtgg ttctcacggg ttcttaatcg  13380
gccacattgt tcccgaagcc gctgaaggtg gtcctatcgg gttggtcaga gacggcgatg  13440
agattatcat tgatgctgat aataacaaga ttgacctatt agtctctgat aaggaaatgg  13500
ctcaacgtaa acaaagttgg gttgcacctc cacctcgtta cacaagaggt actctatcca  13560
agtatgctaa gttggtttcc aacgcttcca acggttgtgt tttagatgct tgattaatta  13620
agagtaagcg aatttcttat gatttatgat ttttattatt aaataagtta taaaaaaaat  13680
aagtgtatac aaattttaaa gtgactctta ggttttaaaa cgaaaattct tattcttgag  13740
taactctttc ctgtaggtca ggttgctttc tcaggtatag catgaggtcg ctcttattga  13800
ccacacctct accggcatgc cgagcaaatg cctgcaaatc gctccccatt tcacccaatt  13860
gtagatatgc taactccagc aatgagttga tgaatctcgg tgtgtatttt atgtcctcag  13920
aggacaacac ctgtggtact agttctagag cggccgcccg caaattaaag ccttcgagcg  13980
tcccaaaacc ttctcaagca aggttttcag tataatgtta catgcgtaca cgcgtctgta  14040
cagaaaaaaa agaaaaattt gaaatataaa taacgttctt aatactaaca taactataaa  14100
aaaataaata gggacctaga cttcaggttg tctaactcct tccttttcgg ttagagcgga  14160
tgtggggggga gggcgtgaat gtaagcgtga cataactaat tacatgatta attaactaga  14220
gagctttcgt tttcatgagt tccccgaatt ctttcggaag cttgtcactt gctaaattaa  14280
tgttatcact gtagtcaacc gggacatcga tgatgacagg accttcagcg ttcatgcctt  14340
gacgcagaac atctgccagc tggtctggtg attctacgcg caagccagtt gctccgaagc  14400
tttccgcata tttcacgata tcgatatttc cgaaatcgac cgcagatgta cggttatatt  14460
ttttcaattg ctggaatgca accatgtcat atgtgctgtc gttccataca atgtgtacaa  14520
ttggtgcttt tagtcgaact gctgtctcta attccattgc tgagaataag aaaccgccgt  14580
caccagagac agaaaccact ttttctcccg gtttcaccaa tgaagcgccg attgcccaag  14640
gaagcgcaac gccgagtgtt tgcataccgt tactgatcat taatgttaac ggctcgtagc  14700
tgcggaaata acgtgacatc caaatggcgt gcgaaccgat atcgcaagtt actgtaacat  14760
gatcatcgac tgcattacgc aactctttaa cgatttcaag agggtgcgct ctgtctgatt  14820
tccaatctgc aggcacctgc tcaccttcat gcatatattg ttttaaatca gaaaggattt  14880
```

```
tctgctcacg ctctgcaaat tccactttca cagcatcgtg ttcgatatga ttgatcgtgg  14940

acggaatgtc accgatcaat tcaagatcag gctggtaagc atgatcaatg tcagcgataa  15000

tctcgtctaa atggataatt gtccggtctc cattgatatt ccagaatttc ggatcatatt  15060

caatcgggtc atagccgatc gtcagaacaa catctgcctg ctctagcagt aaatcgccag  15120

gctggttgcg gaacaaaccg atacggccaa aatattgatc ctctaaatct ctagaaaggg  15180

taccggcagc ttgatatgtt tcaacaaatg gaagctgaac ctttttcaaa agcttgcgaa  15240

ccgctttaat tgcttccggt cttccgcctt tcatgccgac caaaacgaca ggaagttttg  15300

ctgtttggat ttttgctatg gccgcactga ttgcatcatc tgctgcagga ccgagttttg  15360

gcgctgcaac agcacgcacg tttttcgtat ttgtgacttc attcacaaca tcttgcggaa  15420

agctcacaaa agcggcccca gcctgccctg ctgacgctat cctaaatgca tttgtaacag  15480

cttccggtat attttttaca tcttgaactt ctacactgta ttttgtaatc ggctggaata  15540

gcgccgcatt atccaaagat tgatgtgtcc gttttaaacg atctgcacgg atcacgtttc  15600

cagcaagcgc aacgacaggg tctccttcag tgttcgctgt cagcaggcct gttgccaagt  15660

tagaggcacc cggtcctgat gtgactaaca cgactcccgg ttttccagtt aaacggccga  15720

ctgcttgggc catgaatgct gcgttttgtt cgtgccgggc aacgataatt tcaggtcctt  15780

tatcttgtaa agcgtcaaat accgcatcaa tttttgcacc tggaatgcca aatacatgtg  15840

tgacaccttg ctccactaag caatcaacaa caagctccgc ccctctgttt ttcacaaggg  15900

atttttgttc ttttgttgct tttgtcaaca tcctcagcga tgattgattg attgattgta  15960

cagtttgttt ttcttaatat ctatttcgat gacttctata tgatattgca ctaacaagaa  16020

gatattataa tgcaattgat acaagacaag gagttatttg cttctctttt atatgattct  16080

gacaatccat attgcgttgg tagtcttttt tgctggaacg gttcagcgga aaagacgcat  16140

cgctcttttt gcttctagaa gaaatgccag caaaagaatc tcttgacagt gactgacagc  16200

aaaaatgtct ttttctaact agtaacaagg ctaagatatc agcctgaaat aaagggtggt  16260

gaagtaataa ttaaatcatc cgtataaacc tatacacata tatgaggaaa aataatacaa  16320

aagtgtttta aatacagata catacatgaa catatgcacg tatagcgccc aaatgtcggt  16380

aatggga                                                            16387
```

<210> SEQ ID NO 131
<211> LENGTH: 1188
<212> TYPE: DNA
<213> ORGANISM: Saccharomyces cerevisiae

<400> SEQUENCE: 131

```
atgttgagaa ctcaagccgc cagattgatc tgcaactccc gtgtcatcac tgctaagaga     60

acctttgctt tggccacccg tgctgctgct tacagcagac cagctgcccg tttcgttaag    120

ccaatgatca ctacccgtgg tttgaagcaa atcaacttcg gtggtactgt tgaaaccgtc    180

tacgaaagag ctgactggcc aagagaaaag ttgttggact acttcaagaa cgacactttt    240

gctttgatcg gttacggttc ccaaggttac ggtcaaggtt tgaacttgag agacaacggt    300

ttgaacgtta tcattggtgt ccgtaaagat ggtgcttctt ggaaggctgc catcgaagac    360

ggttgggttc caggcaagaa cttgttcact gttgaagatg ctatcaagag aggtagttac    420

gttatgaact tgttgtccga tgccgctcaa tcagaaacct ggcctgctat caagccattg    480

ttgaccaagg gtaagacttt gtacttctcc cacggtttct ccccagtctt caaggacttg    540

actcacgttg aaccaccaaa ggacttagat gttatcttgg ttgctccaaa gggttccggt    600
```

agaactgtca gatctttgtt caaggaaggt cgtggtatta actcttctta cgccgtctgg 660
aacgatgtca ccggtaaggc tcacgaaaag gcccaagctt tggccgttgc cattggttcc 720
ggttacgttt accaaaccac tttcgaaaga gaagtcaact ctgacttgta cggtgaaaga 780
ggttgtttaa tgggtggtat ccacggtatg ttcttggctc aatacgacgt cttgagagaa 840
aacggtcact ccccatctga agctttcaac gaaaccgtcg aagaagctac ccaatctcta 900
tacccattga tcggtaagta cggtatggat tacatgtacg atgcttgttc caccaccgcc 960
agaagaggtg ctttggactg gtacccaatc ttcaagaatg ctttgaagcc tgttttccaa 1020
gacttgtacg aatctaccaa gaacggtacc gaaaccaaga gatctttgga attcaactct 1080
caacctgact acagagaaaa gctagaaaag gaattagaca ccatcagaaa catggaaatc 1140
tggaaggttg gtaaggaagt cagaaagttg agaccagaaa accaataa 1188

<210> SEQ ID NO 132
<211> LENGTH: 1014
<212> TYPE: DNA
<213> ORGANISM: Pseudomonas fluorescens

<400> SEQUENCE: 132
atgaaagttt tctacgataa agactgcgac ctgtcgatca tccaaggtaa gaaagttgcc 60
atcatcggct acggttccca gggccacgct caagcatgca acctgaagga ttccggcgta 120
gacgtgactg ttggcctgcg taaaggctcg gctaccgttg ccaaggctga agcccacggc 180
ttgaaagtga ccgacgttgc tgcagccgtt gccggtgccg acttggtcat gatcctgacc 240
ccggacgagt tccagtccca gctgtacaag aacgaaatcg agccgaacat caagaagggc 300
gccactctgg ccttctccca cggcttcgcg atccactaca accaggttgt gcctcgtgcc 360
gacctcgacg tgatcatgat cgcgccgaag gctccaggcc acaccgtacg ttccgagttc 420
gtcaagggcg gtggtattcc tgacctgatc gcgatctacc aggacgcttc cggcaacgcc 480
aagaacgttg ccctgtccta cgccgcaggc gtgggcggcg gccgtaccgg catcatcgaa 540
accaccttca aggacgagac tgaaaccgac ctgttcggtg agcaggctgt tctgtgtggc 600
ggtaccgtcg agctggtcaa agccggtttc gaaaccctgg ttgaagctgg ctacgctcca 660
gaaatggcct acttcgagtg cctgcacgaa ctgaagctga tcgttgacct catgtacgaa 720
ggcggtatcg ccaacatgaa ctactcgatc tccaacaacg ctgaatacgg cgagtacgtg 780
actggtccag aagtcatcaa cgccgaatcc cgtcaggcca tgcgcaatgc tctgaagcgc 840
atccaggacg gcgaatacgc gaagatgttc atcagcgaag gcgctaccgg ctacccatcg 900
atgaccgcca agcgtcgtaa caacgctgct cacggtatcg aaatcatcgg cgagcaactg 960
cgctcgatga tgccttggat cggtgccaac aaaatcgtcg acaaagccaa gaac 1014

<210> SEQ ID NO 133
<211> LENGTH: 250
<212> TYPE: DNA
<213> ORGANISM: Saccharomyces cerevisiae

<400> SEQUENCE: 133
ccgcaaatta aagccttcga gcgtcccaaa accttctcaa gcaaggtttt cagtataatg 60
ttacatgcgt acacgcgtct gtacagaaaa aaaagaaaaa tttgaaatat aaataacgtt 120
cttaatacta acataactat aaaaaaataa atagggacct agacttcagg ttgtctaact 180
ccttcctttt cggttagagc ggatgtgggg ggagggcgtg aatgtaagcg tgacataact 240
aattacatga 250

<210> SEQ ID NO 134
<211> LENGTH: 1181
<212> TYPE: DNA
<213> ORGANISM: Saccharomyces cerevisiae

<400> SEQUENCE: 134

```
taaaacctct agtggagtag tagatgtaat caatgaagcg gaagccaaaa gaccagagta     60
gaggcctata gaagaaactg cgataccttt tgtgatggct aaacaaacag acatcttttt    120
atatgttttt acttctgtat atcgtgaagt agtaagtgat aagcgaattt ggctaagaac    180
gttgtaagtg aacaagggac ctcttttgcc tttcaaaaaa ggattaaatg gagttaatca    240
ttgagattta gttttcgtta gattctgtat ccctaaataa ctcccttacc cgacgggaag    300
gcacaaaaga cttgaataat agcaaacggc cagtagccaa gaccaaataa tactagagtt    360
aactgatggt cttaaacagg cattacgtgg tgaactccaa gaccaatata caaaatatcg    420
ataagttatt cttgcccacc aatttaagga gcctacatca ggacagtagt accattcctc    480
agagaagagg tatacataac aagaaaatcg cgtgaacacc ttatataact tagcccgtta    540
ttgagctaaa aaaccttgca aaatttccta tgaataagaa tacttcagac gtgataaaaa    600
tttactttct aactcttctc acgctgcccc tatctgttct tccgctctac cgtgagaaat    660
aaagcatcga gtacggcagt tcgctgtcac tgaactaaaa caataaggct agttcgaatg    720
atgaacttgc ttgctgtcaa acttctgagt tgccgctgat gtgacactgt gacaataaat    780
tcaaaccggt tatagcggtc tcctccggta ccggttctgc cacctccaat agagctcagt    840
aggagtcaga acctctgcgg tggctgtcag tgactcatcc gcgtttcgta agttgtgcgc    900
gtgcacattt cgcccgttcc cgctcatctt gcagcaggcg gaaattttca tcacgctgta    960
ggacgcaaaa aaaaaataat taatcgtaca agaatcttgg aaaaaaaatt gaaaaatttt   1020
gtataaaagg gatgacctaa cttgactcaa tggcttttac acccagtatt ttccctttcc   1080
ttgtttgtta caattataga agcaagacaa aaacatatag acaacctatt cctaggagtt   1140
atattttttt accctaccag caatataagt aaaaaactag t                       1181
```

<210> SEQ ID NO 135
<211> LENGTH: 759
<212> TYPE: DNA
<213> ORGANISM: Saccharomyces cerevisiae

<400> SEQUENCE: 135

```
ggccctgcag gcctatcaag tgctggaaac tttttctctt ggaatttttg caacatcaag     60
tcatagtcaa ttgaattgac ccaatttcac atttaagatt tttttttttt catccgacat    120
acatctgtac actaggaagc cctgtttttc tgaagcagct tcaaatatat atattttta    180
catatttatt atgattcaat gaacaatcta attaaatcga aaacaagaac cgaaacgcga    240
ataaataatt tatttagatg gtgacaagtg tataagtcct catcgggaca gctacgattt    300
ctctttcggt tttggctgag ctactggttg ctgtgacgca gcggcattag cgcggcgtta    360
tgagctaccc tcgtggcctg aaagatggcg ggaataaagc ggaactaaaa attactgact    420
gagccatatt gaggtcaatt tgtcaactcg tcaagtcacg tttggtggac ggcccctttc    480
caacgaatcg tatatactaa catgcgcgcg cttcctatat acacatatac atatatatat    540
atatatatat gtgtgcgtgt atgtgtacac ctgtatttaa tttccttact cgcgggtttt    600
tctttttct caattcttgg cttcctcttt ctcgagtata taatttttca ggtaaaattt    660
agtacgatag taaaatactt ctcgaactcg tcacatatac gtgtacataa tgtctgaacc    720
```

agctcaaaag aaacaaaagg ttgctaacaa ctctctaga 759

<210> SEQ ID NO 136
<211> LENGTH: 643
<212> TYPE: DNA
<213> ORGANISM: Saccharomyces cerevisiae

<400> SEQUENCE: 136
gaaatgaata acaatactga cagtactaaa taattgccta cttggcttca catacgttgc 60
atacgtcgat atagataata atgataatga cagcaggatt atcgtaatac gtaatagttg 120
aaaatctcaa aaatgtgtgg gtcattacgt aaataatgat aggaatggga ttcttctatt 180
tttccttttt ccattctagc agccgtcggg aaaacgtggc atcctctctt tcgggctcaa 240
ttggagtcac gctgccgtga gcatcctctc tttccatatc taacaactga gcacgtaacc 300
aatggaaaag catgagctta gcgttgctcc aaaaaagtat tggatggtta ataccatttg 360
tctgttctct tctgactttg actcctcaaa aaaaaaaaat ctacaatcaa cagatcgctt 420
caattacgcc ctcacaaaaa ctttttttcct tcttcttcgc ccacgttaaa ttttatccct 480
catgttgtct aacggatttc tgcacttgat ttattataaa aagacaaaga cataatactt 540
ctctatcaat ttcagttatt gttcttcctt gcgttattct tctgttcttc tttttctttt 600
gtcatatata accataacca agtaatacat attcaaatct aga 643

<210> SEQ ID NO 137
<211> LENGTH: 1716
<212> TYPE: DNA
<213> ORGANISM: Bacillus subtilis

<400> SEQUENCE: 137
atgttgacaa aagcaacaaa agaacaaaaa tcccttgtga aaaacagagg ggcggagctt 60
gttgttgatt gcttagtgga gcaaggtgtc acacatgtat ttggcattcc aggtgcaaaa 120
attgatgcgg tatttgacgc tttacaagat aaaggacctg aaattatcgt tgcccggcac 180
gaacaaaacg cagcattcat ggcccaagca gtcggccgtt taactggaaa accgggagtc 240
gtgttagtca catcaggacc gggtgcctct aacttggcaa caggcctgct gacagcgaac 300
actgaaggag accctgtcgt tgcgcttgct ggaaacgtga tccgtgcaga tcgtttaaaa 360
cggacacatc aatctttgga taatgcggcg ctattccagc cgattacaaa atacagtgta 420
gaagttcaag atgtaaaaaa tataccggaa gctgttacaa atgcatttag gatagcgtca 480
gcagggcagg ctggggccgc ttttgtgagc tttccgcaag atgttgtgaa tgaagtcaca 540
aatacgaaaa acgtgcgtgc tgttgcagcg ccaaaactcg gtcctgcagc agatgatgca 600
atcagtgcgg ccatagcaaa aatccaaaca gcaaaacttc ctgtcgtttt ggtcggcatg 660
aaaggcggaa gaccggaagc aattaaagcg gttcgcaagc ttttgaaaaa ggttcagctt 720
ccatttgttg aaacatatca agctgccggt accctttcta gagatttaga ggatcaatat 780
tttggccgta tcggtttgtt ccgcaaccag cctggcgatt tactgctaga gcaggcagat 840
gttgttctga cgatcggcta tgacccgatt gaatatgatc cgaaattctg gaatatcaat 900
ggagaccgga caattatcca tttagacgag attatcgctg acattgatca tgcttaccag 960
cctgatcttg aattgatcgg tgacattccg tccacgatca atcatatcga acacgatgct 1020
gtgaaagtgg aatttgcaga gcgtgagcag aaaatccttt ctgatttaaa acaatatatg 1080
catgaaggtg agcaggtgcc tgcagattgg aaatcagaca gagcgcaccc tcttgaaatc 1140
gttaaagagt tgcgtaatgc agtcgatgat catgttacag taacttgcga tatcggttcg 1200

```
cacgccattt ggatgtcacg ttatttccgc agctacgagc cgttaacatt aatgatcagt   1260

aacggtatgc aaacactcgg cgttgcgctt ccttgggcaa tcggcgcttc attggtgaaa   1320

ccgggagaaa aagtggtttc tgtctctggt gacggcggtt tcttattctc agcaatggaa   1380

ttagagacag cagttcgact aaaagcacca attgtacaca ttgtatggaa cgacagcaca   1440

tatgacatgg ttgcattcca gcaattgaaa aaatataacc gtacatctgc ggtcgatttc   1500

ggaaatatcg atatcgtgaa atatgcggaa agcttcggag caactggctt gcgcgtagaa   1560

tcaccagacc agctggcaga tgttctgcgt caaggcatga acgctgaagg tcctgtcatc   1620

atcgatgtcc cggttgacta cagtgataac attaatttag caagtgacaa gcttccgaaa   1680

gaattcgggg aactcatgaa aacgaaagct ctctag                             1716


<210> SEQ ID NO 138
<211> LENGTH: 571
<212> TYPE: PRT
<213> ORGANISM: Bacillus subtilis

<400> SEQUENCE: 138

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285
```

```
Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 139
<211> LENGTH: 448
<212> TYPE: DNA
<213> ORGANISM: Saccharomyces cerevisiae

<400> SEQUENCE: 139

```
cccattaccg acatttgggc gctatacgtg catatgttca tgtatgtatc tgtatttaaa      60

acacttttgt attatttttc ctcatatatg tgtataggtt tatacggatg atttaattat     120

tacttcacca ccctttattt caggctgata tcttagcctt gttactagtt agaaaaagac     180

atttttgctg tcagtcactg tcaagagatt cttttgctgg catttcttct agaagcaaaa     240

agagcgatgc gtcttttccg ctgaaccgtt ccagcaaaaa agactaccaa cgcaatatgg     300

attgtcagaa tcatataaaa gagaagcaaa taactccttg tcttgtatca attgcattat     360

aatatcttct tgttagtgca atatcatata gaagtcatcg aaatagatat taagaaaaac     420

aaactgtaca atcaatcaat caatcatc                                        448
```

<210> SEQ ID NO 140

<211> LENGTH: 16387
<212> TYPE: DNA
<213> ORGANISM: Artificial Sequence
<220> FEATURE:
<223> OTHER INFORMATION: plasmid construct

<400> SEQUENCE: 140
tcccattacc gacatttggg cgctatacgt gcatatgttc atgtatgtat ctgtatttaa 60
aacacttttg tattattttt cctcatatat gtgtataggt ttatacggat gatttaatta 120
ttacttcacc accctttatt tcaggctgat atcttagcct tgttactagt tagaaaaaga 180
catttttgct gtcagtcact gtcaagagat tcttttgctg gcatttcttc tagaagcaaa 240
aagagcgatg cgtcttttcc gctgaaccgt tccagcaaaa aagactacca acgcaatatg 300
gattgtcaga atcatataaa agagaagcaa ataactcctt gtcttgtatc aattgcatta 360
taatatcttc ttgttagtgc aatatcatat agaagtcatc gaaatagata ttaagaaaaa 420
caaactgtac aatcaatcaa tcaatcatcg ctgaggatgt tgacaaaagc aacaaaagaa 480
caaaaatccc ttgtgaaaaa cagaggggcg gagcttgttg ttgattgctt agtggagcaa 540
ggtgtcacac atgtatttgg cattccaggt gcaaaaattg atgcggtatt tgacgcttta 600
caagataaag gacctgaaat tatcgttgcc cggcacgaac aaaacgcagc attcatggcc 660
caagcagtcg gccgtttaac tggaaaaccg ggagtcgtgt tagtcacatc aggaccgggt 720
gcctctaact tggcaacagg cctgctgaca gcgaacactg aaggagaccc tgtcgttgcg 780
cttgctggaa acgtgatccg tgcagatcgt ttaaaacgga cacatcaatc tttggataat 840
gcggcgctat tccagccgat tacaaaatac agtgtagaag ttcaagatgt aaaaaatata 900
ccggaagctg ttacaaatgc atttaggata gcgtcagcag ggcaggctgg ggccgctttt 960
gtgagctttc cgcaagatgt tgtgaatgaa gtcacaaata cgaaaaacgt gcgtgctgtt 1020
gcagcgccaa aactcggtcc tgcagcagat gatgcaatca gtgcggccat agcaaaaatc 1080
caaacagcaa aacttcctgt cgttttggtc ggcatgaaag gcggaagacc ggaagcaatt 1140
aaagcggttc gcaagctttt gaaaaaggtt cagcttccat ttgttgaaac atatcaagct 1200
gccggtaccc tttctagaga tttagaggat caatattttg gccgtatcgg tttgttccgc 1260
aaccagcctg gcgatttact gctagagcag gcagatgttg ttctgacgat cggctatgac 1320
ccgattgaat atgatccgaa attctggaat atcaatggag accggacaat tatccattta 1380
gacgagatta tcgctgacat tgatcatgct taccagcctg atcttgaatt gatcggtgac 1440
attccgtcca cgatcaatca tatcgaacac gatgctgtga aagtggaatt tgcagagcgt 1500
gagcagaaaa tcctttctga tttaaaacaa tatatgcatg aaggtgagca ggtgcctgca 1560
gattggaaat cagacagagc gcaccctctt gaaatcgtta aagagttgcg taatgcagtc 1620
gatgatcatg ttacagtaac ttgcgatatc ggttcgcacg ccatttggat gtcacgttat 1680
ttccgcagct acgagccgtt aacattaatg atcagtaacg gtatgcaaac actcggcgtt 1740
gcgcttcctt gggcaatcgg cgcttcattg gtgaaaccgg gagaaaaagt ggtttctgtc 1800
tctggtgacg gcggtttctt attctcagca atggaattag agacagcagt tcgactaaaa 1860
gcaccaattg tacacattgt atggaacgac agcacatatg acatggttgc attccagcaa 1920
ttgaaaaaat ataaccgtac atctgcggtc gatttcggaa atatcgatat cgtgaaatat 1980
gcggaaagct tcggagcaac tggcttgcgc gtagaatcac cagaccagct ggcagatgtt 2040
ctgcgtcaag gcatgaacgc tgaaggtcct gtcatcatcg atgtcccggt tgactacagt 2100
gataacatta atttagcaag tgacaagctt ccgaaagaat tcggggaact catgaaaacg 2160

```
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt ttttttataa cttatttaat aataaaaatc ataaatcata agaaattcgc   2760
ttactcttaa ttaatcaagc atctaaaaca caaccgttgg aagcgttgga aaccaactta   2820
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag gctttagcat ttcaggcata   3120
cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gtttttagag atcctgttaa aacctctagt ggagtagtag   4020
atgtaatcaa tgaagcggaa gccaaaagac cagagtagag gcctatagaa gaaactgcga   4080
taccttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaaagactt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
```

```
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaattttgta taaaagggat gacctaactt   5040
gactcaatgg cttttacacc cagtattttc cctttccttg tttgttacaa ttatagaagc   5100
aagacaaaaa catatagaca acctattcct aggagttata tttttttacc ctaccagcaa   5160
tataagtaaa aaactagtat gaaggtgttt tacgataaag actgcgatct gagcatcatc   5220
cagggaaaga aggttgctat tataggatat ggttcccaag gacacgcaca agccttgaac   5280
ttgaaagatt ctggggtcga cgtgacagta ggtctgtata aaggtgctgc tgatgcagca   5340
aaggctgaag cacatggctt taaagtcaca gatgttgcag cggctgttgc tggcgctgat   5400
ttagtcatga ttttaattcc agatgaattt caatcgcaat tgtacaaaaa tgaaatagaa   5460
ccaaacatta agaagggcgc taccttggcc ttcagtcatg gatttgccat tcattacaat   5520
caagtagtcc ccagggcaga tttggacgtt attatgattg cacctaaggc tccggggcat   5580
actgttagga gcgaatttgt taagggtggt ggtattccag atttgatcgc tatataccaa   5640
gacgttagcg gaaacgctaa gaatgtagct ttaagctacg cagcaggagt tggtggcggg   5700
agaacgggta taatagaaac cacttttaaa gacgagactg agacagattt atttggagaa   5760
caagcggttc tgtgcggagg aactgttgaa ttggttaaag caggctttga gacgcttgtc   5820
gaagcagggt acgctcccga aatggcatac ttcgaatgtc tacatgaatt gaagttgata   5880
gtagacttaa tgtatgaagg tggtatagct aatatgaact attccatttc aaataatgca   5940
gaatatggtg agtatgtcac cggacctgaa gtcattaacg cagaatcaag acaagccatg   6000
agaaatgcct tgaaacgtat ccaggacggt gaatacgcta agatgttcat aagtgaaggc   6060
gctacgggtt acccgagtat gactgctaaa agaagaaaca atgcagcaca tggtatcgaa   6120
attattggtg aacagttaag gtctatgatg ccctggatcg gtgctaataa gatcgtagac   6180
aaggcgaaaa attaaggccc tgcaggccta tcaagtgctg gaaacttttt ctcttggaat   6240
ttttgcaaca tcaagtcata gtcaattgaa ttgacccaat ttcacattta agattttttt   6300
tttttcatcc gacatacatc tgtacactag gaagccctgt ttttctgaag cagcttcaaa   6360
tatatatatt ttttacatat ttattatgat tcaatgaaca atctaattaa atcgaaaaca   6420
agaaccgaaa cgcgaataaa taatttattt agatggtgac aagtgtataa gtcctcatcg   6480
ggacagctac gatttctctt tcggttttgg ctgagctact ggttgctgtg acgcagcggc   6540
attagcgcgg cgttatgagc taccctcgtg gcctgaaaga tggcgggaat aaagcggaac   6600
taaaaattac tgactgagcc atattgaggt caatttgtca actcgtcaag tcacgtttgg   6660
tggacggccc ctttccaacg aatcgtatat actaacatgc gcgcgcttcc tatatacaca   6720
tatacatata tatatatata tatatgtgtg cgtgtatgtg tacacctgta tttaatttcc   6780
ttactcgcgg gtttttcttt ttttctcaatt cttggcttcc tctttctcga gtatataatt   6840
tttcaggtaa aatttagtac gatagtaaaa tacttctcga actcgtcaca tatacgtgta   6900
cataatgtct gaaccagctc aaaagaaaca aaaggttgct aacaactctc tagagcggcc   6960
```

```
gcccgcaaat taaagccttc gagcgtccca aaaccttctc aagcaaggtt ttcagtataa   7020
tgttacatgc gtacacgcgt ctgtacagaa aaaaaagaaa aatttgaaat ataaataacg   7080
ttcttaatac taacataact ataaaaaaat aaatagggac ctagacttca ggttgtctaa   7140
ctccttcctt ttcggttaga gcggatgtgg ggggagggcg tgaatgtaag cgtgacataa   7200
ctaattacat gattaattaa ttattggttt tctggtctca actttctgac ttccttacca   7260
accttccaga tttccatgtt tctgatggtg tctaattcct tttctagctt ttctctgtag   7320
tcaggttgag agttgaattc caaagatctc ttggtttcgg taccgttctt ggtagattcg   7380
tacaagtctt ggaaaacagg cttcaaagca ttcttgaaga ttgggtacca gtccaaagca   7440
cctcttctgg cggtggtgga acaagcatcg tacatgtaat ccataccgta cttaccgatc   7500
aatgggtata gagattgggt agcttcttcg acggtttcgt tgaaagcttc agatggggag   7560
tgaccgtttt ctctcaagac gtcgtattga gccaagaaca taccgtggat accacccatt   7620
aaacaacctc tttcaccgta caagtcagag ttgacttctc tttcgaaagt ggtttggtaa   7680
acgtaaccgg aaccaatggc aacggccaaa gcttgggcct tttcgtgagc cttaccggtg   7740
acatcgttcc agacggcgta agaagagtta ataccacgac cttccttgaa caaagatctg   7800
acagttctac cggaaccctt tggagcaacc aagataacat ctaagtcctt tggtggttca   7860
acgtgagtca agtccttgaa gactggggag aaaccgtggg agaagtacaa agtcttaccc   7920
ttggtcaaca atggcttgat agcaggccag gtttctgatt gagcggcatc ggacaacaag   7980
ttcataacgt aactacctct cttgatagca tcttcaacag tgaacaagtt cttgcctgga   8040
acccaaccgt cttcgatggc agccttccaa gaagcaccat ctttacggac accaatgata   8100
acgttcaaac cgttgtctct caagttcaaa ccttgaccgt aaccttggga accgtaaccg   8160
atcaaagcaa aagtgtcgtt cttgaagtag tccaacaact ttctcttgg ccagtcagct   8220
ctttcgtaga cggtttcaac agtaccaccg aagttgattt gcttcaacat cctcagctct   8280
agatttgaat atgtattact tggttatggt tatatatgac aaaagaaaaa gaagaacaga   8340
agaataacgc aaggaagaac aataactgaa attgatagag aagtattatg tctttgtctt   8400
tttataataa atcaagtgca gaaatccgtt agacaacatg agggataaaa tttaacgtgg   8460
gcgaagaaga aggaaaaaag tttttgtgag ggcgtaattg aagcgatctg ttgattgtag   8520
attttttttt tttgaggagt caaagtcaga agagaacaga caaatggtat taaccatcca   8580
atactttttt ggagcaacgc taagctcatg cttttccatt ggttacgtgc tcagttgtta   8640
gatatggaaa gagaggatgc tcacggcagc gtgactccaa ttgagcccga aagagaggat   8700
gccacgtttt cccgacggct gctagaatgg aaaaaggaaa aatagaagaa tcccattcct   8760
atcattattt acgtaatgac ccacacattt ttgagatttt caactattac gtattacgat   8820
aatcctgctg tcattatcat tattatctat atcgacgtat gcaacgtatg tgaagccaag   8880
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc gggggctccc tttagggttc cgatttagtg   9360
```

```
ctttacggca cctcgacccc aaaaaacttg atttgggtga tggttcacgt agtgggccat    9420
cgccctgata gacggttttt cgccctttga cgttggagtc cacgttcttt aatagtggac    9480
tcttgttcca aactggaaca acactcaact ctatctcggg ctattctttt gatttataag    9540
ggattttgcc gatttcggtc tattggttaa aaaatgagct gatttaacaa aaatttaacg    9600
cgaattttaa caaaatatta acgtttacaa ttttatggtg cactctcagt acaatctgct    9660
ctgatgccgc atagttaagc cagccccgac acccgccaac acccgctgac gcgccctgac    9720
gggcttgtct gctcccggca tccgcttaca gacaagctgt gaccgtctcc gggagctgca    9780
tgtgtcagag gttttcaccg tcatcaccga aacgcgcgag acgaaagggc ctcgtgatac    9840
gcctattttt ataggttaat gtcatgataa taatggtttc ttagacgtca ggtggcactt    9900
ttcggggaaa tgtgcgcgga acccctattt gtttattttt ctaaatacat tcaaatatgt    9960
atccgctcat gagacaataa ccctgataaa tgcttcaata atattgaaaa aggaagagta   10020
tgagtattca acatttccgt gtcgccctta ttcccttttt tgcggcattt tgccttcctg   10080
tttttgctca cccagaaacg ctggtgaaag taaaagatgc tgaagatcag ttgggtgcac   10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac accacgatgc   10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
cactgattaa gcattggtaa ctgtcagacc aagtttactc atatatactt tagattgatt   10920
taaaacttca tttttaattt aaaaggatct aggtgaagat cctttttgat aatctcatga   10980
ccaaaatccc ttaacgtgag ttttcgttcc actgagcgtc agaccccgta gaaaagatca   11040
aaggatcttc ttgagatcct ttttttctgc gcgtaatctg ctgcttgcaa acaaaaaaac   11100
caccgctacc agcggtggtt tgtttgccgg atcaagagct accaactctt tttccgaagg   11160
taactggctt cagcagagcg cagataccaa atactgttct tctagtgtag ccgtagttag   11220
gccaccactt caagaactct gtagcaccgc ctacatacct cgctctgcta atcctgttac   11280
cagtggctgc tgccagtggc gataagtcgt gtcttaccgg gttggactca agacgatagt   11340
taccggataa ggcgcagcgg tcgggctgaa cggggggttc gtgcacacag cccagcttgg   11400
agcgaacgac ctacaccgaa ctgagatacc tacagcgtga gctatgagaa agcgccacgc   11460
ttcccgaagg gagaaaggcg gacaggtatc cggtaagcgg cagggtcgga acaggagagc   11520
gcacgaggga gcttccaggg ggaaacgcct ggtatcttta tagtcctgtc gggtttcgcc   11580
acctctgact tgagcgtcga tttttgtgat gctcgtcagg ggggcggagc ctatggaaaa   11640
acgccagcaa cgcggccttt ttacggttcc tggccttttg ctggcctttt gctcacatgt   11700
tctttcctgc gttatcccct gattctgtgg ataaccgtat taccgccttt gagtgagctg   11760
```

-continued

```
ataccgctcg ccgcagccga acgaccgagc gcagcgagtc agtgagcgag gaagcggaag  11820
agcgcccaat acgcaaaccg cctctccccg cgcgttggcc gattcattaa tgcagctggc  11880
acgacaggtt tcccgactgg aaagcgggca gtgagcgcaa cgcaattaat gtgagttagc  11940
tcactcatta ggcaccccag gctttacact ttatgcttcc ggctcgtatg ttgtgtggaa  12000
ttgtgagcgg ataacaattt cacacaggaa acagctatga ccatgattac gccaagcttt  12060
ttctttccaa ttttttttt ttcgtcatta taaaaatcat tacgaccgag attcccgggt  12120
aataactgat ataattaaat tgaagctcta atttgtgagt ttagtataca tgcatttact  12180
tataatacag tttttagtt ttgctggccg catcttctca aatatgcttc ccagcctgct  12240
tttctgtaac gttcaccctc taccttagca tcccttccct ttgcaaatag tcctcttcca  12300
acaataataa tgtcagatcc tgtagagacc acatcatcca cggttctata ctgttgaccc  12360
aatgcgtctc ccttgtcatc taaacccaca ccgggtgtca taatcaacca atcgtaacct  12420
tcatctcttc cacccatgtc tctttgagca ataaagccga taacaaaatc tttgtcgctc  12480
ttcgcaatgt caacagtacc cttagtatat tctccagtag atagggagcc cttgcatgac  12540
aattctgcta acatcaaaag gcctctaggt tcctttgtta cttcttctgc cgcctgcttc  12600
aaaccgctaa caatacctgg gcccaccaca ccgtgtgcat tcgtaatgtc tgcccattct  12660
gctattctgt atacacccgc agagtactgc aatttgactg tattaccaat gtcagcaaat  12720
tttctgtctt cgaagagtaa aaaattgtac ttggcggata atgcctttag cggcttaact  12780
gtgccctcca tggaaaaatc agtcaagata tccacatgtg tttttagtaa acaaattttg  12840
ggacctaatg cttcaactaa ctccagtaat tccttggtgg tacgaacatc caatgaagca  12900
cacaagtttg tttgcttttc gtgcatgata ttaaatagct tggcagcaac aggactagga  12960
tgagtagcag cacgttcctt atatgtagct ttcgacatga tttatcttcg tttcctgcag  13020
gtttttgttc tgtgcagttg ggttaagaat actgggcaat ttcatgtttc ttcaacacta  13080
catatgcgta tatataccaa tctaagtctg tgctccttcc ttcgttcttc cttctgttcg  13140
gagattaccg aatcaaaaaa atttcaagga aaccgaaatc aaaaaaaaga ataaaaaaaa  13200
aatgatgaat tgaaaagctt gcatgcctgc aggtcgactc tagtatactc cgtctactgt  13260
acgatacact tccgctcagg tccttgtcct ttaacgaggc cttaccactc ttttgttact  13320
ctattgatcc agctcagcaa aggcagtgtg atctaagatt ctatcttcgc gatgtagtaa  13380
aactagctag accgagaaag agactagaaa tgcaaaaggc acttctacaa tggctgccat  13440
cattattatc cgatgtgacg ctgcattttt ttttttttt ttttttttt ttttttttt  13500
ttttttttt tttttttgta caaatatcat aaaaaaagag aatcttttta agcaaggatt  13560
ttcttaactt cttcggcgac agcatcaccg acttcggtgg tactgttgga accacctaaa  13620
tcaccagttc tgatacctgc atccaaaacc tttttaactg catcttcaat ggctttacct  13680
tcttcaggca agttcaatga caatttcaac atcattgcag cagacaagat agtggcgata  13740
gggttgacct tattctttgg caaatctgga gcggaaccat ggcatggttc gtacaaacca  13800
aatgcggtgt tcttgtctgg caaagaggcc aaggacgcag atggcaacaa acccaaggag  13860
cctgggataa cggaggcttc atcggagatg atatcaccaa acatgttgct ggtgattata  13920
ataccattta ggtgggttgg gttcttaact aggatcatgg cggcagaatc aatcaattga  13980
tgttgaactt tcaatgtagg gaattcgttc ttgatggttt cctccacagt tttctccat  14040
aatcttgaag aggccaaaac attagcttta tccaaggacc aaataggcaa tggtggctca  14100
tgttgtaggg ccatgaaagc ggccattctt gtgattcttt gcacttctgg aacggtgtat  14160
```

```
tgttcactat cccaagcgac accatcacca tcgtcttcct ttctcttacc aaagtaaata  14220
cctcccacta attctctaac aacaacgaag tcagtacctt tagcaaattg tggcttgatt  14280
ggagataagt ctaaaagaga gtcggatgca aagttacatg gtcttaagtt ggcgtacaat  14340
tgaagttctt tacggatttt tagtaaacct tgttcaggtc taacactacc ggtaccccat  14400
ttaggaccac ccacagcacc taacaaaacg gcatcagcct tcttggaggc ttccagcgcc  14460
tcatctggaa gtggaacacc tgtagcatcg atagcagcac caccaattaa atgattttcg  14520
aaatcgaact tgacattgga acgaacatca gaaatagctt taagaacctt aatggcttcg  14580
gctgtgattt cttgaccaac gtggtcacct ggcaaaacga cgatcttctt aggggcagac  14640
attacaatgg tatatccttg aaatatatat aaaaaaaaaa aaaaaaaaaa aaaaaaaaaa  14700
tgcagcttct caatgatatt cgaatacgct ttgaggagat acagcctaat atccgacaaa  14760
ctgttttaca gatttacgat cgtacttgtt acccatcatt gaattttgaa catccgaacc  14820
tgggagtttt ccctgaaaca gatagtatat ttgaacctgt ataataatat atagtctagc  14880
gctttacgga agacaatgta tgtatttcgg ttcctggaga aactattgca tctattgcat  14940
aggtaatctt gcacgtcgca tccccggttc attttctgcg tttccatctt gcacttcaat  15000
agcatatctt tgttaacgaa gcatctgtgc ttcattttgt agaacaaaaa tgcaacgcga  15060
gagcgctaat ttttcaaaca aagaatctga gctgcatttt tacagaacag aaatgcaacg  15120
cgaaagcgct attttaccaa cgaagaatct gtgcttcatt tttgtaaaac aaaaatgcaa  15180
cgcgagagcg ctaatttttc aaacaaagaa tctgagctgc atttttacag aacagaaatg  15240
caacgcgaga gcgctatttt accaacaaag aatctatact tctttttgt tctacaaaaa  15300
tgcatcccga gagcgctatt tttctaacaa agcatcttag attacttttt ttctcctttg  15360
tgcgctctat aatgcagtct cttgataact tttgcactg taggtccgtt aaggttagaa  15420
gaaggctact ttggtgtcta ttttctcttc cataaaaaaa gcctgactcc acttcccgcg  15480
tttactgatt actagcgaag ctgcgggtgc attttttcaa gataaaggca tccccgatta  15540
tattctatac cgatgtggat tgcgcatact ttgtgaacag aaagtgatag cgttgatgat  15600
tcttcattgg tcagaaaatt atgaacggtt tcttctattt tgtctctata tactacgtat  15660
aggaaatgtt tacattttcg tattgttttc gattcactct atgaatagtt cttactacaa  15720
tttttttgtc taaagagtaa tactagagat aaacataaaa aatgtagagg tcgagtttag  15780
atgcaagttc aaggagcgaa aggtggatgg gtaggttata tagggatata gcacagagat  15840
atatagcaaa gagatacttt tgagcaatgt ttgtggaagc ggtattcgca atattttagt  15900
agctcgttac agtccggtgc gtttttggtt ttttgaaagt gcgtcttcag agcgcttttg  15960
gttttcaaaa gcgctctgaa gttcctatac tttctagaga ataggaactt cggaatagga  16020
acttcaaagc gtttccgaaa acgagcgctt ccgaaaatgc aacgcgagct gcgcacatac  16080
agctcactgt tcacgtcgca cctatatctg cgtgttgcct gtatatatat atacatgaga  16140
agaacggcat agtgcgtgtt tatgcttaaa tgcgtactta tatgcgtcta tttatgtagg  16200
atgaaaggta gtctagtacc tcctgtgata ttatcccatt ccatgcgggg tatcgtatgc  16260
ttccttcagc actacccttt agctgttcta tatgctgcca ctcctcaatt ggattagtct  16320
catccttcaa tgctatcatt tcctttgata ttggatcata tgcatagtac cgagaaacta  16380
gaggatc                                                            16387
```

<210> SEQ ID NO 141
<211> LENGTH: 2237
<212> TYPE: DNA

<213> ORGANISM: Artificial Sequence
<220> FEATURE:
<223> OTHER INFORMATION: PDC1 Fragment A-ilvDSm

<400> SEQUENCE: 141

```
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt ttcttcataa    180
ttgcataata ttgtccgctg ccccttttc tgttagacgg tgtcttgatc tacttgctat    240
cgttcaacac caccttattt tctaactatt tttttttag ctcatttgaa tcagcttatg    300
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
tcggccattg gaaccacggc gatatgacca aagaagaagt taaagctttg gaatgtaatg   1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttccctttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
```

```
tttaatctct aattatt                                                  2237


<210> SEQ ID NO 142
<211> LENGTH: 4420
<212> TYPE: DNA
<213> ORGANISM: Artificial Sequence
<220> FEATURE:
<223> OTHER INFORMATION: PDC1 A-ilvDSm-BUC cassette

<400> SEQUENCE: 142

ttatgtatgc tcttctgact tttcgtgtga tgaggctcgt ggaaaaaatg aataatttat     60

gaatttgaga acaattttgt gttgttacgg tattttacta tggaataatc aatcaattga    120

ggattttatg caaatatcgt ttgaatattt ttccgaccct ttgagtactt ttcttcataa    180

ttgcataata ttgtccgctg ccccttttc tgttagacgg tgtcttgatc tacttgctat    240

cgttcaacac caccttattt tctaactatt tttttttag ctcatttgaa tcagcttatg    300

gtgatggcac atttttgcat aaacctagct gtcctcgttg aacataggaa aaaaaaatat    360

ataaacaagg ctctttcact ctccttgcaa tcagatttgg gtttgttccc tttattttca    420

tatttcttgt catattcctt tctcaattat tattttctac tcataacctc acgcaaaata    480

acacagtcaa atcaatcaaa atgactgaca aaaaaactct taaagactta agaaatcgta    540

gttctgttta cgattcaatg gttaaatcac ctaatcgtgc tatgttgcgt gcaactggta    600

tgcaagatga agactttgaa aaacctatcg tcggtgtcat ttcaacttgg gctgaaaaca    660

caccttgtaa tatccactta catgactttg gtaaactagc caaagtcggt gttaaggaag    720

ctggtgcttg gccagttcag ttcggaacaa tcacggtttc tgatggaatc gccatgggaa    780

cccaaggaat gcgtttctcc ttgacatctc gtgatattat tgcagattct attgaagcag    840

ccatgggagg tcataatgcg gatgcttttg tagccattgg cggttgtgat aaaaacatgc    900

ccggttctgt tatcgctatg gctaacatgg atatcccagc catttttgct tacggcggaa    960

caattgcacc tggtaattta gacggcaaag atatcgattt agtctctgtc tttgaaggtg   1020

tcggccattg gaaccacggc gatatgacca aagaagaagt taaagctttg gaatgtaatg   1080

cttgtcccgg tcctggaggc tgcggtggta tgtatactgc taacacaatg gcgacagcta   1140

ttgaagtttt gggacttagc cttccgggtt catcttctca cccggctgaa tccgcagaaa   1200

agaaagcaga tattgaagaa gctggtcgcg ctgttgtcaa aatgctcgaa atgggcttaa   1260

aaccttctga cattttaacg cgtgaagctt ttgaagatgc tattactgta actatggctc   1320

tgggaggttc aaccaactca acccttcacc tcttagctat tgcccatgct gctaatgtgg   1380

aattgacact tgatgatttc aatactttcc aagaaaaagt tcctcatttg gctgatttga   1440

aaccttctgg tcaatatgta ttccaagacc tttacaaggt cggaggggta ccagcagtta   1500

tgaaatatct ccttaaaaat ggcttccttc atggtgaccg tatcacttgt actggcaaaa   1560

cagtcgctga aaatttgaag gcttttgatg atttaacacc tggtcaaaag gttattatgc   1620

cgcttgaaaa tcctaaacgt gaagatggtc cgctcattat tctccatggt aacttggctc   1680

cagacggtgc cgttgccaaa gtttctggtg taaaagtgcg tcgtcatgtc ggtcctgcta   1740

aggtctttaa ttctgaagaa gaagccattg aagctgtctt gaatgatgat attgttgatg   1800

gtgatgttgt tgtcgtacgt tttgtaggac caaagggcgg tcctggtatg cctgaaatgc   1860

tttccctttc atcaatgatt gttggtaaag ggcaaggtga aaaagttgcc cttctgacag   1920

atggccgctt ctcaggtggt acttatggtc ttgtcgtggg tcatatcgct cctgaagcac   1980

aagatggcgg tccaatcgcc tacctgcaaa caggagacat agtcactatt gaccaagaca   2040
```

```
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattattagt taaagtttta taagcatttt tatgtaacga aaaataaatt   2280
ggttcatatt attactgcac tgtcacttac catggaaaga ccagacaaga agttgccgac   2340
agtctgttga attggcctgg ttaggcttaa gtctgggtcc gcttctttac aaatttggag   2400
aatttctctt aaacgatatg tatattcttt tcgttggaaa agatgtcttc caaaaaaaaa   2460
accgatgaat tagtggaacc aaggaaaaaa aaagaggtat ccttgattaa ggaacactgt   2520
ttaaacagtg tggtttccaa aaccctgaaa ctgcattagt gtaatagaag actagacacc   2580
tcgatacaaa taatggttac tcaattcaaa actgccagcg aattcgactc tgcaattgct   2640
caagacaagc tagttgtcgt agatttctac gccacttggt gcggtccatg taaaatgatt   2700
gctccaatga ttgaaaaatg tggctgtggt ttcagggtcc ataaagcttt tcaattcatc   2760
ttttttttt ttgttctttt ttttgattcc ggtttctttg aaattttttt gattcggtaa    2820
tctccgagca gaaggaagaa cgaaggaagg agcacagact tagattggta tatatacgca   2880
tatgtggtgt tgaagaaaca tgaaattgcc cagtattctt aacccaactg cacagaacaa   2940
aaacctgcag gaaacgaaga taaatcatgt cgaaagctac atataaggaa cgtgctgcta   3000
ctcatcctag tcctgttgct gccaagctat ttaatatcat gcacgaaaag caaacaaact   3060
tgtgtgcttc attggatgtt cgtaccacca aggaattact ggagttagtt gaagcattag   3120
gtcccaaaat ttgtttacta aaaacacatg tggatatctt gactgatttt tccatggagg   3180
gcacagttaa gccgctaaag gcattatccg ccaagtacaa tttttactc ttcgaagaca    3240
gaaaatttgc tgacattggt aatacagtca aattgcagta ctctgcgggt gtatacagaa   3300
tagcagaatg ggcagacatt acgaatgcac acggtgtggt gggcccaggt attgttagcg   3360
gtttgaagca ggcggcggaa gaagtaacaa aggaacctag aggccttttg atgttagcag   3420
aattgtcatg caagggctcc ctagctactg gagaatatac taagggtact gttgacattg   3480
cgaagagcga caaagatttt gttatcggct ttattgctca aagagacatg ggtggaagag   3540
atgaaggtta cgattggttg attatgacac ccggtgtggg tttagatgac aagggagacg   3600
cattgggtca acagtataga accgtggatg atgtggtctc tacaggatct gacattatta   3660
ttgttggaag aggactattt gcaaagggaa gggatgctaa ggtagagggt gaacgttaca   3720
gaaaagcagg ctgggaagca tatttgagaa gatgcggcca gcaaaactaa aaaactgtat   3780
tataagtaaa tgcatgtata ctaaactcac aaattagagc ttcaatttaa ttatatcagt   3840
tattacccgg gaatctcggt cgtaatgatt tctataatga cgaaaaaaaa aaaattggaa   3900
agaaaaagct tcatggcctt ccactttccc aaacaacacc tacggtatct ctcaagtctt   3960
atggggttcc attggtttca ccactggtgc taccttgggt gctgctttcg ctgctgaaga   4020
aattgatcca aagaagagag ttatcttatt cattggtgac ggttctttgc aattgactgt   4080
tcaagaaatc tccaccatga tcagatgggg cttgaagcca tacttgttcg tcttgaacaa   4140
cgatggttac accattgaaa agttgattca cggtccaaag gctcaataca acgaaattca   4200
aggttgggac cacctatcct tgttgccaac tttcggtgct aaggactatg aaacccacag   4260
agtcgctacc accggtgaat gggacaagtt gacccaagac aagtctttca acgacaactc   4320
taagatcaga atgattgaaa tcatgttgcc agtcttcgat gctccacaaa acttggttga   4380
acaagctaag ttgactgctg ctaccaacgc taagcaataa                         4420
```

<210> SEQ ID NO 143
<211> LENGTH: 2686
<212> TYPE: DNA
<213> ORGANISM: Artificial Sequence
<220> FEATURE:
<223> OTHER INFORMATION: pUC19

<400> SEQUENCE: 143
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggat 420
cctctagagt cgacctgcag gcatgcaagc ttggcgtaat catggtcata gctgtttcct 480
gtgtgaaatt gttatccgct cacaattcca cacaacatac gagccggaag cataaagtgt 540
aaagcctggg gtgcctaatg agtgagctaa ctcacattaa ttgcgttgcg ctcactgccc 600
gctttccagt cgggaaacct gtcgtgccag ctgcattaat gaatcggcca acgcgcgggg 660
agaggcggtt tgcgtattgg gcgctcttcc gcttcctcgc tcactgactc gctgcgctcg 720
gtcgttcggc tgcggcgagc ggtatcagct cactcaaagg cggtaatacg gttatccaca 780
gaatcagggg ataacgcagg aaagaacatg tgagcaaaag gccagcaaaa ggccaggaac 840
cgtaaaaagg ccgcgttgct ggcgtttttc cataggctcc gcccccctga cgagcatcac 900
aaaaatcgac gctcaagtca gaggtggcga aacccgacag gactataaag ataccaggcg 960
tttccccctg gaagctccct cgtgcgctct cctgttccga ccctgccgct taccggatac 1020
ctgtccgcct ttctcccttc gggaagcgtg gcgctttctc atagctcacg ctgtaggtat 1080
ctcagttcgg tgtaggtcgt tcgctccaag ctgggctgtg tgcacgaacc ccccgttcag 1140
cccgaccgct gcgccttatc cggtaactat cgtcttgagt ccaacccggt aagacacgac 1200
ttatcgccac tggcagcagc cactggtaac aggattagca gagcgaggta tgtaggcggt 1260
gctacagagt tcttgaagtg gtggcctaac tacggctaca ctagaaggac agtatttggt 1320
atctgcgctc tgctgaagcc agttaccttc ggaaaaagag ttggtagctc ttgatccggc 1380
aaacaaacca ccgctggtag cggtggtttt tttgtttgca agcagcagat tacgcgcaga 1440
aaaaaaggat ctcaagaaga tcctttgatc ttttctacgg ggtctgacgc tcagtggaac 1500
gaaaactcac gttaagggat tttggtcatg agattatcaa aaaggatctt cacctagatc 1560
cttttaaatt aaaaatgaag ttttaaatca atctaaagta tatatgagta aacttggtct 1620
gacagttacc aatgcttaat cagtgaggca cctatctcag cgatctgtct atttcgttca 1680
tccatagttg cctgactccc cgtcgtgtag ataactacga tacgggaggg cttaccatct 1740
ggccccagtg ctgcaatgat accgcgagac ccacgctcac cggctccaga tttatcagca 1800
ataaaccagc cagccggaag ggccgagcgc agaagtggtc ctgcaacttt atccgcctcc 1860
atccagtcta ttaattgttg ccgggaagct agagtaagta gttcgccagt taatagtttg 1920
cgcaacgttg ttgccattgc tacaggcatc gtggtgtcac gctcgtcgtt tggtatggct 1980
tcattcagct ccggttccca acgatcaagg cgagttacat gatcccccat gttgtgcaaa 2040
aaagcggtta gctccttcgg tcctccgatc gttgtcagaa gtaagttggc cgcagtgtta 2100

```
tcactcatgg ttatggcagc actgcataat tctcttactg tcatgccatc cgtaagatgc   2160

ttttctgtga ctggtgagta ctcaaccaag tcattctgag aatagtgtat gcggcgaccg   2220

agttgctctt gcccggcgtc aatacgggat aataccgcgc cacatagcag aactttaaaa   2280

gtgctcatca ttggaaaacg ttcttcgggg cgaaaactct caaggatctt accgctgttg   2340

agatccagtt cgatgtaacc cactcgtgca cccaactgat cttcagcatc ttttactttc   2400

accagcgttt ctgggtgagc aaaaacagga aggcaaaatg ccgcaaaaaa gggaataagg   2460

gcgacacgga aatgttgaat actcatactc ttcctttttc aatattattg aagcatttat   2520

cagggttatt gtctcatgag cggatacata tttgaatgta tttagaaaaa taaacaaata   2580

ggggttccgc gcacatttcc ccgaaaagtg ccacctgacg tctaagaaac cattattatc   2640

atgacattaa cctataaaaa taggcgtatc acgaggccct ttcgtc                  2686
```

<210> SEQ ID NO 144
<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 144

```
aaggaaataa agcaaataac aataacacca ttattttaat ttttttttcta ttactgtcgc     60

taacacctgt atggttgcaa ccaggtgaga atccttctga tgcatacttt atgcgtttat    120

gcgttttgcg ccccttggaa aaaaattgat tctcatcgta aatgcatact acatgcgttt    180

atgggaaaag cctccatatc caaaggtcgc gtttctttta gaaaaactaa tacgtaaacc    240

tgcattaagg taagattata tcagaaaatg tgttgcaaga aatgcattat gcaatttttt    300

gattatgaca atctctcgaa agaaatttca tatgatgaga cttgaataat gcagcggcgc    360

ttgctaaaag aacttgtata taagagctgc cattctcgat caatatactg tagtaagtcc    420

tttcctctct ttcttattac acttatttca cataatcaat ctcaaagaga acaacacaat    480

acaataacaa gaagaacaaa atgaaagctc tggtttatca cggtgaccac aagatctcgc    540

ttgaagacaa gcccaagccc acccttcaaa agcccacgga tgtagtagta cgggttttga    600

agaccacgat ctgcggcacg gatctcggca tctacaaagg caagaatcca gaggtcgccg    660

acgggcgcat cctgggccat gaaggggtag gcgtcatcga ggaagtgggc gagagtgtca    720

cgcagttcaa gaaaggcgac aaggtcctga tttcctgcgt cacttcttgc ggctcgtgcg    780

actactgcaa gaagcagctt tactcccatt gccgcgacgg cgggtggatc ctgggttaca    840

tgatcgatgg cgtgcaggcc gaatacgtcc gcatcccgca tgccgacaac agcctctaca    900

agatccccca gacaattgac gacgaaatcg ccgtcctgct gagcgacatc ctgcccaccg    960

gccacgaaat cggcgtccag tatgggaatg tccagccggg cgatgcggtg gctattgtcg   1020

gcgcgggccc cgtcggcatg tccgtactgt tgaccgccca gttctactcc ccctcgacca   1080

tcatcgtgat cgacatggac gagaatcgcc tccagctcgc caaggagctc ggggcaacgc   1140

acaccatcaa ctccggcacg gagaacgttg tcgaagccgt gcataggatt gcggcagagg   1200

gagtcgatgt tgcgatcgag gcggtgggca taccggcgac ttgggacatc tgccaggaga   1260

tcgtcaagcc cggcgcgcac atcgccaacg tcggcgtgca tggcgtcaag gttgacttcg   1320

agattcagaa gctctggatc aagaacctga cgatcaccac gggactggtg aacacgaaca   1380

cgacgcccat gctgatgaag gtcgcctcga ccgacaagct tccgttgaag aagatgatta   1440

cccatcgctt cgagctggcc gagatcgagc acgcctatca ggtattcctc aatggcgcca   1500
```

```
aggagaaggc gatgaagatc atcctctcga acgcaggcgc tgcctgagct aattaacata   1560
aaactcatga ttcaacgttt gtgtattttt ttacttttga aggttataga tgtttaggta   1620
aataattggc atagatatag ttttagtata ataaatttct gatttggttt aaaatatcaa   1680
ctattttttt tcacatatgt tcttgtaatt acttttctgt cctgtcttcc aggttaaaga   1740
ttagcttcta atattttagg tggtttatta tttaatttta tgctgattaa tttatttact   1800
tgtttaaacg gccggccaat gtggctgtgg tttcagggtc cataaagctt ttcaattcat   1860
cttttttttt tttgttcttt tttttgattc cggtttcttt gaaatttttt tgattcggta   1920
atctccgagc agaaggaaga acgaaggaag gagcacagac ttagattggt atatatacgc   1980
atatgtggtg ttgaagaaac atgaaattgc ccagtattct taacccaact gcacagaaca   2040
aaaacctgca ggaaacgaag ataaatcatg tcgaaagcta catataagga acgtgctgct   2100
actcatccta gtcctgttgc tgccaagcta tttaatatca tgcacgaaaa gcaaacaaac   2160
ttgtgtgctt cattggatgt tcgtaccacc aaggaattac tggagttagt tgaagcatta   2220
ggtcccaaaa tttgtttact aaaaacacat gtggatatct tgactgattt ttccatggag   2280
ggcacagtta agccgctaaa ggcattatcc gccaagtaca attttttact cttcgaagac   2340
agaaaatttg ctgacattgg taatacagtc aaattgcagt actctgcggg tgtatacaga   2400
atagcagaat gggcagacat tacgaatgca cacggtgtgg tgggcccagg tattgttagc   2460
ggtttgaagc aggcggcgga agaagtaaca aaggaaccta gaggcctttt gatgttagca   2520
gaattgtcat gcaagggctc cctagctact ggagaatata ctaagggtac tgttgacatt   2580
gcgaagagcg acaaagattt tgttatcggc tttattgctc aaagagacat gggtggaaga   2640
gatgaaggtt acgattggtt gattatgaca cccggtgtgg gtttagatga caagggagac   2700
gcattgggtc aacagtatag aaccgtggat gatgtggtct ctacaggatc tgacattatt   2760
attgttggaa gaggactatt tgcaaaggga agggatgcta aggtagaggg tgaacgttac   2820
agaaaagcag gctgggaagc atatttgaga agatgcggcc agcaaaacta aaaaactgta   2880
ttataagtaa atgcatgtat actaaactca caaattagag cttcaattta attatatcag   2940
ttattacccg ggaatctcgg tcgtaatgat ttctataatg acgaaaaaaa aaaaaattgga  3000
aagaaaaagc ttcatggcct tctactttcc caacagatgt atacgctatc gtccaagtct   3060
tgtggggttc cattggtttc acagtcggcg ctctattggg tgctactatg gccgctgaag   3120
aacttgatcc aaagaagaga gttattttat tcattggtga cggttctcta caattgactg   3180
ttcaagaaat ctctaccatg attagatggg gtttgaagcc atacattttt gtcttgaata   3240
acaacggtta caccattgaa aaattgattc acggtcctca tgccgaatat aatgaaattc   3300
aaggttggga ccacttggcc ttattgccaa cttttggtgc tagaaactac gaaacccaca   3360
gagttgctac cactggtgaa tgggaaaagt tgactcaaga caaggacttc caagacaact   3420
ctaagattag aatgattgaa gttatgttgc cagtctttga tgctccacaa aacttggtta   3480
aacaagctca attgactgcc gctactaacg ctaaacaata a                       3521
```

<210> SEQ ID NO 145
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 145

```
gtattttggt agattcaatt ctctttccct ttccttttcc ttcgctcccc ttccttatca     60
```

-continued

```
gcattgcgga ttacgtattc taatgttcag ataacttcgt atagcataca ttatacgaag    120

ttatgcagat tgtactgaga gtgcaccata ccacagcttt tcaattcaat tcatcatttt    180

tttttattc ttttttttga tttcggtttc tttgaaattt ttttgattcg gtaatctccg    240

aacagaagga agaacgaagg aaggagcaca gacttagatt ggtatatata cgcatatgta    300

gtgttgaaga aacatgaaat tgcccagtat tcttaaccca actgcacaga acaaaaacct    360

gcaggaaacg aagataaatc atgtcgaaag ctacatataa ggaacgtgct gctactcatc    420

ctagtcctgt tgctgccaag ctatttaata tcatgcacga aaagcaaaca aacttgtgtg    480

cttcattgga tgttcgtacc accaaggaat tactggagtt agttgaagca ttaggtccca    540

aaatttgttt actaaaaaca catgtggata tcttgactga tttttccatg gagggcacag    600

ttaagccgct aaaggcatta tccgccaagt acaatttttt actcttcgaa gacagaaaat    660

ttgctgacat tggtaataca gtcaaattgc agtactctgc gggtgtatac agaatagcag    720

aatgggcaga cattacgaat gcacacggtg tggtgggccc aggtattgtt agcggtttga    780

agcaggcggc agaagaagta acaaaggaac ctagaggcct tttgatgtta gcagaattgt    840

catgcaaggg ctccctatct actggagaat atactaaggg tactgttgac attgcgaaga    900

gcgacaaaga ttttgttatc ggctttattg ctcaaagaga catgggtgga agagatgaag    960

gttacgattg gttgattatg acacccggtg tgggtttaga tgacaaggga gacgcattgg   1020

gtcaacagta tagaaccgtg gatgatgtgg tctctacagg atctgacatt attattgttg   1080

gaagaggact atttgcaaag ggaagggatg ctaaggtaga gggtgaacgt tacagaaaag   1140

caggctggga agcatatttg agaagatgcg gccagcaaaa ctaaaaaact gtattataag   1200

taaatgcatg tatactaaac tcacaaatta gagcttcaat ttaattatat cagttattac   1260

cctatgcggt gtgaaatacc gcacagatgc gtaaggagaa aataccgcat caggaaattg   1320

taaacgttaa tattttgtta aaattcgcgt taaatttttg ttaaatcagc tcatttttta   1380

accaataggc cgaaatcggc aaaatccctt ataaatcaaa agaatagacc gagatagggt   1440

tgagtgttgt tccagtttgg aacaagagtc cactattaaa gaacgtggac tccaacgtca   1500

aagggcgaaa aaccgtctat cagggcgatg gcccactacg tgaaccatca ccctaatcaa   1560

gataacttcg tatagcatac attatacgaa gttatccagt gatgatacaa cgagttagcc   1620

aaggtgacac tctccccccc cctccccctc tgatctttcc tgttgcctct tttcccccca   1680

accaa                                                                1685
```